US009756871B2

(12) United States Patent
Rommens et al.

(10) Patent No.: US 9,756,871 B2
(45) Date of Patent: Sep. 12, 2017

(54) TAL-MEDIATED TRANSFER DNA INSERTION

(71) Applicant: J.R. SIMPLOT COMPANY, Boise, ID (US)

(72) Inventors: Caius M. Rommens, Boise, ID (US); Hui Duan, Boise, ID (US); J. Troy Weeks, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 675 days.

(21) Appl. No.: 14/084,406

(22) Filed: Nov. 19, 2013

(65) Prior Publication Data

US 2014/0154397 A1 Jun. 5, 2014

Related U.S. Application Data

(60) Provisional application No. 61/790,434, filed on Mar. 15, 2013, provisional application No. 61/728,466, filed on Nov. 20, 2012.

(51) Int. Cl.
*C12N 15/82* (2006.01)
*A23L 1/216* (2006.01)
*A23L 1/217* (2006.01)
*A23L 19/18* (2016.01)

(52) U.S. Cl.
CPC ............... *A23L 1/217* (2013.01); *A23L 19/18* (2016.08); *C12N 15/825* (2013.01); *C12N 15/8209* (2013.01); *C12N 15/8213* (2013.01); *C12N 15/8245* (2013.01); *C12N 15/8251* (2013.01); *C12N 15/8278* (2013.01); *C12N 15/8282* (2013.01)

(58) Field of Classification Search
None
See application file for complete search history.

(56) References Cited

U.S. PATENT DOCUMENTS

| 2007/0074304 | A1* | 3/2007 | Rommens | C12N 9/82 800/278 |
|---|---|---|---|---|
| 2010/0031401 | A1 | 2/2010 | Rommens et al. | |
| 2011/0021118 | A1 | 1/2011 | Wang | |
| 2011/0145940 | A1 | 6/2011 | Voytas et al. | |
| 2011/0301073 | A1 | 12/2011 | Gregory et al. | |
| 2014/0363561 | A1 | 12/2014 | Rommens | |

FOREIGN PATENT DOCUMENTS

| CN | 1842593 A | 10/2006 |
|---|---|---|
| WO | 2007111968 A2 | 10/2007 |
| WO | WO 2007/111968 A2 | 10/2007 |
| WO | 2009/131632 A1 | 10/2009 |
| WO | WO 2011/1541159 | 12/2011 |
| WO | WO 2014/081729 | 5/2014 |
| WO | WO 2014/144094 A1 | 9/2014 |

OTHER PUBLICATIONS

Rommens et al 2006 (J. Agric. Food Chem. 54: p. 9882-9887).*
Garbarino et al 1995 (Plant Physiology 109: p. 1371-1378).*
Foster et al 2009 (Molecular Plant Microbe Interactions 22: p. 589-600).*
Malzahn et al 2017 (Cell Bioscience 7:21).*
Garbarino, J E., et al: "Isolation of a polyubiquitin promoter and its expression in transgenic potato plants", Plant Physiology, Jan. 1, 1995, pp. 1371-1378, vol. 109.
Sandeep Kumar et al: "Gene Targeting: Development of Novel Systems for Genome Engineering in Plants" Retrieved from the Internet: URL:https://cals.ncsu.edu/hort_sci/people/faculty/pages/documents/allen-globalscience-vol4sample.pdf [retrieved on Mar. 9, 2016], Jan. 1, 2006 (Jan. 1, 2006). pp. 84-98.
European Search Report, European Patent Application No. 13856843.1, mailed Mar. 23, 2016, 10 pages.
Foster et al. Rpi-vnt1. 1, a Tm-22 Homolog from Solanum venturii, Confers Resistance to Potato Late Blight, Molecular Plant-Microbe Interactions 2009; vol. 22, No. 5. pp. 589-600.
International Search Report for related PCT/US2014/028360 mailed on Jul. 18, 2014.
Garbarino et al. "Isolation of polyubiquitin promoter and its expression in transgenic potato plants." Plant Physiol. (Dec. 1995) vol. 109, No. 4, pp. 1371-1378.
International Search Report for related PCT/US2013/070815.
Rommens, C.M., "Precise Breeding Through All-Native DNA Transformation", Genetic Modification of Plants (2009); vol. 64, chapter 4, pp. 61-77.
Zhu and Jacobsen, "Towards Durable Resistance by Stacking Broad Spectrum Cisgenic Resistance Genes" Information Systems for Biotechnology (2012); pp. 4-6, retrieved from: www.isb.vt.edu/news/2012/Jul12.pdf.
PCT/US2013/070815, Written Opinion mailed Feb. 26, 2014, 3 pages.
PCT/US2013/070815, International Preliminary Report on Patentability mailed May 26, 2015, 8 pages.
PCT/US2014/028360, Written Opinion mailed Jul. 18, 2014, 10 pages.
PCT/US2014/028360, International Preliminary Report on Patentability mailed Sep. 15, 2015, 11 pages.
Kohli, Ajay, et al., "Transgene integration, expression and stability in plants: strategies for improvements." Transgenic Crop Plants, Springer Berlin Heidelberg (2010); Chapter 7, pp. 201-237.
van Leeuwen, Wessel, et al. "Characterization of position-induced spatial and temporal regulation of transgene promoter activity in plants." Journal of Experimental Botany (2001); 52.358: 949-959.

* cited by examiner

*Primary Examiner* — Matthew Keogh
(74) *Attorney, Agent, or Firm* — Cooley LLP

(57) ABSTRACT

The invention relates to methods for stably integrating a desired polynucleotide into a plant genome, comprising transforming plant material with a first vector comprising nucleotide sequences encoding TAL proteins designed to recognize a target sequence; transforming the plant material with a second vector comprising (i) a marker gene that is not operably linked to a promoter ("promoter-free marker cassette") and which comprises a sequence homologous to the target sequence; and (ii) a desired polynucleotide; and identifying transformed plant material in which the desired polynucleotide is stably integrated.

19 Claims, 21 Drawing Sheets

FIGURE 5

5A:
```
[highlighted]MAPKKKRKVEPKSSDKTHLQSL[/highlighted]MDPIRSRTPSPARELLSGPQPDGVQPTADRGVSPPAGGPLDGLPARRTMSRTRLPSPP
APSPAFSADSFSDLLRQFDPSLFNTSLFDSLPPFGAHHTEAATGEWDEVQSGLRAADAPPPTMRVAVTAARPPRAKP
APRRRAAQPSDASPAAQVDLRTLGYSQQQQEKIKPKVRSTVAQHHEALVGHGFTHAHIVALSQHPAALGTVAVKYQD
MIAALPEATHEAIVGVGKQWSGARALEALLTVAGELRGPPLQLDTGQLLKIAKRGGVTAVEAVHAWRNALTGAPLN
LTPQQVVAIASNGGKQALETVQRLLPVLCQAHG
LTPQQVVAIASNGGKQALETVQRLLPVLCQAHG
LTPQQVVAIASNGGKQALETVQRLLPVLCQAHG
LTPQQVVAIASNGGKQALETVQRLLPVLCQAHG
LTPEQVVAIASNGGKQALETVQALLPVLCQAHG
LTPEQVVAIASHGGKQALETVQRLLPVLCQAHG
LTPQQVVAIASNGGKQALETVQRLLPVLCQAHG
LTPQQVVAIASNGGKQALETVQRLLPVLCQAHG
LTPQQVVAIASNGGKQALETVQRLLPVLCQAHG
LTPEQVVAIASNGGKQALETVQRLLPVLCQAHG
LTPEQVVAIASNGGKQALETVQRLLPVLCQAHG
LTPEQVVAIASNGGKQALETVQRLLPVLCQAHG
LTPEQVVAIASNGGKQALETVQRLLPVLCQAHG
LTPQQVVAIASNGGKQALETVQRLLPVLCQAQG
LTPEQVVAIASNGGKQALETVQRLLPVLCQAHG
LTPQQVVAIASHGG
RPALESIVAQLSRPDPALAALTNDHLVALACLGGRPALDAVKKGLPHAPALIKRTNRRIPERTSHRVA[highlighted]QLVKSELE
EKKSELRHKLKYVPHEYIELIEIARNSTQDRILEMKVMEFFMKVYGYRGKHLGGSRKPDGAIYTVGSPIDYGVLVDT
KAYSGGYNLPIGQADEMQRYVEENQTRNKHINPNEWWKVYPSSVTEFKFLFVSGHFKGNYKAQLTRLNHITNCNGAV
LSVEELLIGGEMIKAGTLTLEEVRRKFNNGEINF[/highlighted]
```

5B:
```
[highlighted]MAPKKKRKVEPKSSDKTHLQSL[/highlighted]MDPIRSRTPSPARELLSGPQPDGVQPTADRGVSPPAGGPLDGLPARRTMSRTRLPSPP
APSPAFSADSFSDLLRQFDPSLFNTSLFDSLPPFGAHHTEAATGEWDEVQSGLRAADAPPPTMRVAVTAARPPRAKP
APRRRAAQPSDASPAAQVDLRTLGYSQQQQEKIKPKVRSTVAQHHEALVGHGFTHAHIVALSQHPAALGTVAVKYQD
MIAALPEATHEAIVGVGKQWSGARALEALLTVAGELRGPPLQLDTGQLLKIAKRGGVTAVEAVHAWRNALTGAPLN
LTPQQVVAIASNGGKQALETVQRLLPVLCQAHG
LTPQQVVAIASNGGKQALETVQRLLPVLCQAHG
LTPQQVVAIASNGGKQALETVQRLLPVLCQAHG
LTPQQVVAIASNGGKQALETVQRLLPVLCQAHG
LTPEQVVAIASNGGKQALETVQALLPVLCQAHG
LTPEQVVAIASNGGKQALETVQRLLPVLCQAHG
LTPQQVVAIASHGGKQALETVQRLLPVLCQAHG
LTPQQVVAIASNGGKQALETVQRLLPVLCQAHG
LTPQQVVAIASNGGKQALETVQRLLPVLCQAHG
LTPQQVVAIASNGGKQALETVQRLLPVLCQAHG
LTPQQVVAIASNGGKQALETVQRLLPVLCQAHG
LTPEQVVAIASNGGKQALETVQRLLPVLCQAHG
LTPEQVVAIASHGGKQALETVQRLLPVLCQAHG
LTPEQVVAIASNGGKQALETVQRLLPVLCQAHG
LTPQQVVAIASNGGKQALETVQRLLPVLCQAQG
LTPEQVVAIASHGGKQALETVQRLLPVLCQAHG
LTPQQVVAIASNGG
RPALESIVAQLSRPDPALAALTNDHLVALACLGGRPALDAVKKGLPHAPALIKRTNRRIPERTSHRVA[highlighted]QLVKSEE
EKKSELRHKLKYVPHEYIELIEIARNSTQDRILEMKVMEFFMKVYGYRGKHLGGSRKPDGAIYTVGSPIDYGVLVDT
KAYSGGYNLPIGQADEMQRYVEENQTRNKHINPNEWWKVYPSSVTEFKFLFVSGHFKGNYKAQLTRLNHITNCNGAV
LSVEELLIGGEMIKAGTLTLEEVRRKFNNGEINF[/highlighted]
```

FIGURE 8

```
Target      TTTGGTT████████████████TCGAATTAGCTAATCAGG████████████████A
599         TTTGGTTTTTGTCTGTTTAGATTCTCGAATTAGCTAATCAGGTGCTGTTATAGCCCTTAA
116         TTTGGTTTTTGTCTGTTTAGATTCTCGAATTAG█TAATCAGGTGCTGTTATAGCCCTTAA
106         TTTGGTTTTTGTCTGTTTAGATTCTCGAAT------AATCAGGTGCTGTTATAGCCCTTAA
598         TTTGGTTTTTGTCTGTTTAGATTCTCGAA---------ATCAGGTGCTGTTATAGCCCTTAA
593         TTTGGTTTTTGTCTGTTTAGATTCTCGAA---------------CTGTTATAGCCCTTAA
108         TTTGGTTTTTGTCTGTTTAGATTCTCGAAT-----------CAGGTGCTGTTATAGCCCTTAA
604         TTTGGTTTTTGTCTGTTTAGATTCTCGAATTAATC------AGGTGCTGTTATAGCCCTTAA
590         TTTGGTTTTTGTCTGCTTAGATTCTCGAATTAG----------GTGCTGTTATAGCCCTTAA
121         TTTGGTTTTTGTCTGTTTAGATTCTCGAATT-----------CAGGTGCTGTTATAGCCCTTAA
588         TTTGGTTTTTGTCTGTTTAGATTCTCGAATTA------TCAGGTGCTGTTATAGCCCTTAA
602         TTTGGTTTTTGTCTGTTTAGATTCTCGAATTAA------TCAGGTGCTGTTATAGCCCTTAA
112         TTTGGTTTTTGTCTGTTTAGATTCTCGAATTA---TAATCAGGTGCTGTTATAGCCCTTAA
118         TTTGGTTTTTGTCTGTTTAGATTCTCGAATTAGC█TAATCAGGTGCTGTTATAGCCCTTAA
```

FIGURE 9

```
CTGATTTCTATTATAATTTCTATTAATTGCCTTCAAATTTCTCTTTCAAGGTTAGAAATCTTCTCTATTTTTTGGTTTTTGTCTGTTT
AGATTCTCGAATTAGCTAATCAGGTGCTGTTAAAGCCCTAAAATTTGAGTTTTTTTCCGTCGAATTGATGCTAAAGGCTTAAAA
TTAGAGTTTTTTCGTCGGTTTGACTCTGAAGGCCTAAAATTTGGGGTTTTCCGGGTGATTTGATGATAAAGCCCTAGAATTTGA
GTTTTTTTATTTGTCGGTTTGATGAAAAAGGCCTTAAATTTAATTTTTTTCCCGGTTGATTTGATGAAAAAGCCCTAGAATTTGTG
TTTTTTCGTCGGTTTGATTCTAAAGGCCTAAAATTTGAGTTTTTCCGGTTGTTTTGATGAAAAAGCCCTAAAATTTGAGTTTTTTC
CCCGTGTTTAGATTGTTTGGTTTTAATTCTTGAATCAGATAATCAGGGAGTGTGAAAAGCCCTAAAATTTGAGTTTTTTTCGTT
GTTCTGATTGTTGTTTTATGAATTTGATTCTCGAATTAGCTAATCAGGTGCTGTTATAGCCCTTAATTTTGAGTTTTTTTTCGGTT
GTCTTGATGGAAAAGGCCTAAAATTTGAGTTTTTTACGTTGGTTTGATGGAAAAGGCTACAATTGGAGTTTTCCCCGTTGTTT
TGATGAAAAAGCCCTAGTTTGAGATTTTTTCTGTCGATCGATTCTAAAGCTTTAAAATTAGAGTTTTACATTTGTTTGATG
AAAAAGGCCTTAAATTTGAGTTTTTCTCGGTTGATTTGATGAAAAAGCCCTAGAATTTGTGTTTTCGTCGGTTGATTCTAAAGG
TTGATTCTGAAGGCCTAAAATTTGAGTTTTCTCCGGTTGTTTTGATGAAAAAGCCCTAAATTTGAGTTTCTTTGGCTGTTTTGGT
GAAAAGGCCCTAAGTTTGAGTTTTTTCCCCGTGTTTAGATTGTTTGGTTTAATTCTTGAATCAGCTAATCAGGGAGTGTGAAA
AGCCCTAAATTTGAGTTTTTTCGTTGTCTGATTGTTGTTTTATGAATTTGCAGATGCAGATCTTTGTGAAAACTCTCACCGGA
AAGACTATCACCCTAGAGGTGGAAAGTTCTGATACAATCGACAACGTTAAGGCTAAGATCCAGGATAAGGAAGGAATTCCCCC
GGATCAGCAAAGGCTTATCTTCGCCGGAAAGCAGTTGGAGGACGGACGTACTCTAGCTGATTACAACATCCAGAAGGAGTCT
ACCCTCCATTTGGTGCTCCGTCTACGTGGAGGTATGGCGGCTGCTGCCTCACCATCTCCATGTTTCTCCAAAACCCTACCTCCAT
CTTCCTCCAAATCTTCGACCATTCTTCCTAGATCTACCTTCCCTTTCCACAATCACCCTCAAAAAGCCTCACCCCTTCATCTCACCC
```

FIGURE 9 (CONTINUED)

```
TALE2    TTTTCATCTTCTATCTGATTTCTATTATAATTTCTATTAATTGCCTTCAAATTTCTCTTT
TALE3    TTTTCATCTTCTATCTGATTTCTATTATAATTTCTATTAATTGCCTTCAAATTTCTCTTT
         ************************************************************

TALE2    CAAGGTTAGAAATCTTCTCTATTTTTTGGTTTTTGTCTGTTTAGATTCTCGAATTAGCTA
TALE3    CAAGGTTAGAAATCTTCTCTATTTTTTGGTTTTTGTCTGTTTAGATTCTCGAATTAGCTA
         ************************************************************

TALE2    ATCAGGTGCTGTTAAAGCCCTAAAATTTGAGTTTTTTTTCCGCCGAATTGATGCTAAAGG
TALE3    ATCAGGTGCTGTTAAAGCCCTAAAATTTGAGTTTTTTTTCCGCCGAATTGATGCTAAAGG
         ************************************************************

TALE2    CTTAAAATTAGGGTTTTTTCGTCGGTTTGACTCTGAAGGCCTAAAATTTGGGGTTTTCCG
TALE3    CTTAAAATTAGGGTTTTTTCGTCGGTTTGACTCTGAAGGCCTAAAATTTGGGGTTTTCCG
         ************************************************************

TALE2    GGTGATTTGATGATAAAGCCCTAGAATTTGAGTTTTTTTATTTGTCGGTTTGATGAAAAA
TALE3    GGTGATTTGATGATAAAGCCCTAGAATTTGAGTTTTTTATTTGTCGGTTTGATGAAAAA
         ************************************************************

TALE2    GGCCTTAAATTTAATTTTTTTCCCGGTTGATTGATGAAAAAGCCCTAGAATTTGTGTTT
TALE3    GGCCTTAAATTTAATTTTTTTCCCGGTTGATTTGATGAAAAAGCCCTAGAATTTGTGTTT
         ************************************************************

TALE2    TTTCGTCGGTTTGATTCTAAAGGCCTAAAATTTGAGTTTTTCCGGTTGTTTTGATGAAAA
TALE3    TTTCGTCGGTTTGATTCTAAAGGCCTAAAATTTGAGTTTTTCCGGTTGTTTTGATGAAAA
         ************************************************************

TALE2    AGCCCTAAAATTTGAGTTTTTTCGCCGTGTTTTAGATTCTTTGGTTTTAATTCTTGAATC
TALE3    AGCCCTAAAATTTGAGTTTTTTCGCCGTGTTTTAGATTGTTTGGTTTTAATTCTTGAATC
         ************************************************************

TALE2    AGATAATCAGGGAGTGTGAAAAGCCCTAAATTTGAGTTTTTTTCGTTGTTCTGATTGTTG
TALE3    AGATAATCAGGGAGTGTGAAAAGCCCTAAATTTGAGTTTTTTTCGTTGTTCTGATTGTTG
         ************************************************************

TALE2    TTTTTATGAATTTGCAGATGCAGATCTTTGTGAAAACTCTCACCGGAAAGACTATCACCC
TALE3    TTTTTATGAATTTCCAGATGCAGATCTTTGTGAAAACTCTCACCGGAAAGACTATCACCC
         ************************************************************

TALE2    TAGAGGTGGAAA--------CAATCGACAACGTTAAGGCTAAGATCCAGGATAAGGAAG
TALE3    TAGAGGTGGAAAGTTCTGATACAATCGACAACGTTAAGGCTAAGATCCAGGATAAGGAAG
         ************        ****************************************

TALE2    GAATTCCCCCGGATCAGCAAAGGCTTATCTTCGCCGGAAAGCAGTTGGAGGACGGACGTA
TALE3    GAATTCCCCCGGATCAGCAAAGGCTTATCTTCGCCGGAAAGCAGTTGGAGGACGGACGTA
         ************************************************************

TALE2    CTCTAGCTGATTACAACATCCAGAAGGAGTCTACCCTCCATTTGGTGCTCCGTCTACGTG
TALE3    CTCTAGCTGATTACAACATCCAGAAGGAGTCTACCCTCCATTTGGTGCTCCGTCTACGTG
         ************************************************************

TALE2    GAGGTATGGCGGCTGCTGCCTCACCATCTCCATGCTTCTCCAAAACCCTACCTCCATCTT
TALE3    GAGGTATGGCGGCTGCTGCCTCACCATCTCCATGCTTCTCCAAAACCCTACCTCCATCTT
         ************************************************************

TALE2    CCTCCAAATCTTCCACCATTCTTCCTAGATCTACCTTCCCTTTCCACAATCACCCTCAAA
TALE3    CCTCCAAATCTTCCACCATTCTTCCTAGATCTACCTTCCCTTTCCACAATCACCCTCAAA
         ************************************************************
```

FIGURE 11
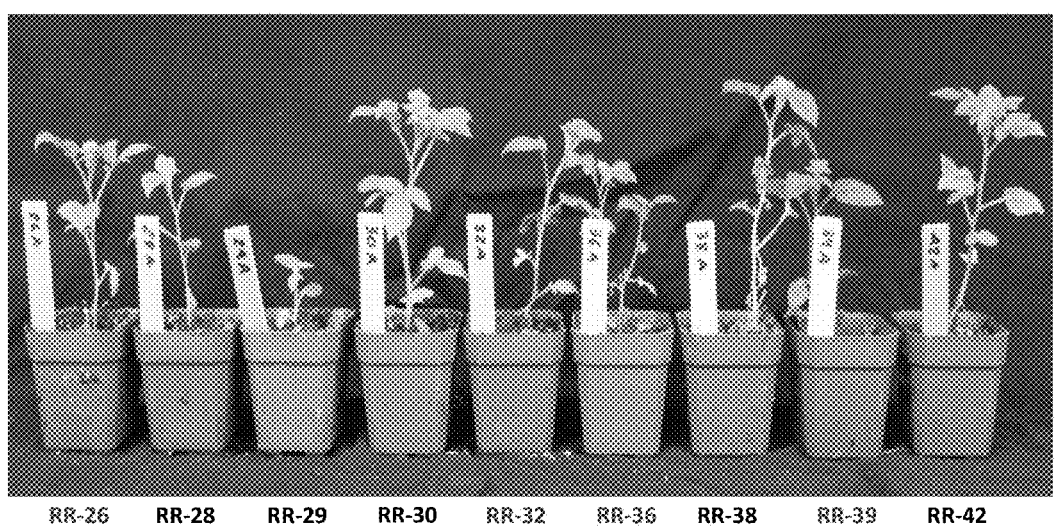

FIGURE 17
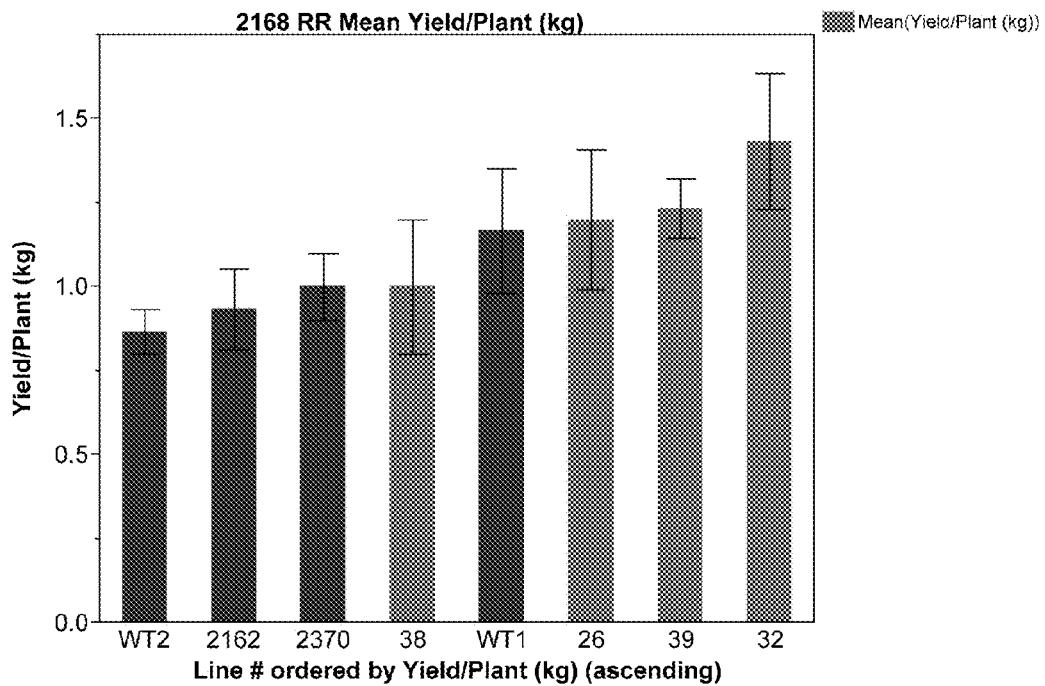
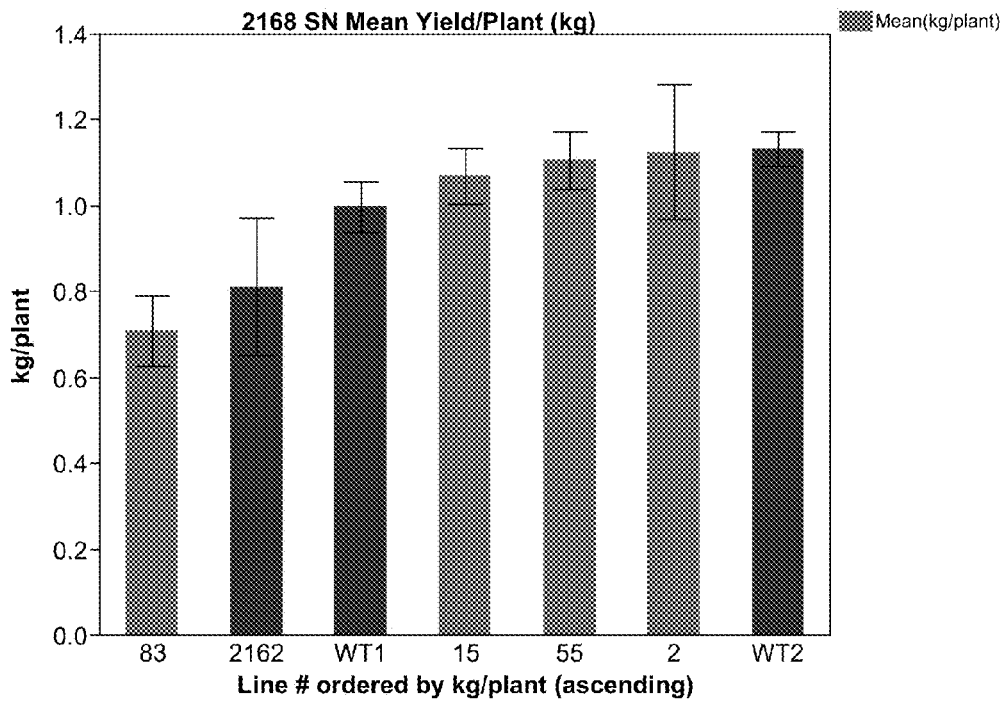

FIGURE 20

```
TTAAGGGCTATAACAGCACCT▓▓▓▓▓▓▓▓▓▓▓▓▓▓▓▓TAAACAGACAAAAACCAAA
TTAAGGGCTATAACAGCACCTGATT    AATTCGAGAATCTAAACAGACAAAAACCAAA
TTAAGGGCTATAACAGCACCTGAT     AATTCGAGAATCTAAACAGACAAAAACCAAA
TTAAGGGCTATAACAGCACCTGATT     TCGAGAATCTAAACAGACAAAAACCAAA
TTAAGGGGCACAACAGCACCTGATT      CGAGAATCTAAACAGACAAAAACCAAA
TTAAGGGCTATAACAGCACCTGATT      CGAGAATCTAAACAGACAAAAACCAAA
TTAAGGGCTATAACAGCA       TCGAGAATCTAAACAGACAAAAACCAAA
TTAAGGGCTATAACAGCACCTGATTAGTAATTCGAGAATCTAAACAGACAAAAACCAAA
TTAAGGGAAAGAACAGCACAGCACTAGATAATTCGAGAATCTAAACAGACAAAAACCAAA
```

TAL-MEDIATED TRANSFER DNA INSERTION

This application claims priority to U.S. provisional application No. 61/790,434, filed Mar. 15, 2013, and U.S. provisional application No. 61/728,466, filed Nov. 20, 2012, both of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 30, 2014, is named 058951-0450_SL.txt and is 100,363 bytes in size.

FIELD OF THE INVENTION

The present invention relates to the field of plant biotechnology and provides methods for targeted transfer DNA insertion for the production of plants and plant products with desirable traits.

BACKGROUND OF THE INVENTION

A plant can be modified through insertion of a DNA segment into its genome. The added DNA comprises genetic elements rearranged to produce RNA that either encodes a protein or triggers the degradation of specific native RNA. The prior art teaches a variety of sub-optimal methods that result in non-targeted (unpredictable and random) insertion.

There is a need in the art for an efficient and reproducible production of genetically engineered plants and plant products with desirable traits. The challenges associated with the employment of transgenic traits are disconcerting, especially because important quality issues have not effectively been addressed through conventional breeding.

SUMMARY OF THE INVENTION

One aspect of the present invention is a method for stably integrating a desired polynucleotide into a plant genome, comprising:
(A) transforming plant material with a first vector comprising nucleotide sequences encoding TAL proteins designed to recognize a target sequence;
(B) transforming the plant material with a second vector comprising (i) a marker gene that is not operably linked to a promoter ("promoter-free marker cassette") and which comprises a sequence homologous to the target sequence; and (ii) a desired polynucleotide; and
(C) identifying transformed plant material in which the desired polynucleotide is stably integrated.

In one embodiment, the transformed plant material is exposed to conditions that reflect the presence or absence of the marker gene in the transformed plant. In another embodiment, the marker gene is a herbicide resistance gene and the transformed plant material is exposed to herbicide. In one embodiment, the herbicide resistance gene is the ALS gene. In another embodiment, the promoter-free marker cassette is stably integrated into the plant genome.

In another embodiment, the invention provides a method for the targeted insertion of exogenous DNA into a plant comprising the steps of (i) transforming isolated plant cells with (A) a first binary vector comprising a promoter-less cassette comprising (a) a right border sequence linked to (b) a partial sequence of the Ubi7 intron 5'-untranslated region; (c) an Ubi7 monomer-encoding sequence fused to a mutated acetolactate synthase (ALS) gene; (d) a desired nucleotide sequence; and (e) a terminator sequence, wherein the desired nucleotide sequence is not operably linked to a promoter; and (B) a second binary vector comprising (a) a right border; (b) a forward expression cassette and a reverse expression cassette, each comprising a modified TAL effector operably linked to a strong constitutive promoter, and a terminator sequence; and (c) a sequence encoding an enzyme involved in cytokinin production, such as isopentenyl transferase (ipt), wherein the modified TAL effector is designed to bind the desired nucleotide sequence within an intron of potato'subiquitin-7 (Ubi7) gene; and (ii) culturing the isolated plant cells under conditions that promote growth of plants that express the desired nucleotide sequence; wherein no vector backbone DNA is permanently inserted into the plant genome.

In a preferred aspect of the invention, the modified TAL effector comprises (a) a truncated C-terminal activation domain comprising a Fok1 endonuclease catalytic domain; (b) a codon-optimized target sequence binding domain comprising 16.5 repeat variable diresidues corresponding to the Ubi7 5'-untranslated intron sequence; and (c) an N-terminal region comprising a SV40 nuclear localization sequence.

In an additional preferred aspect of the invention, the desired nucleotide sequence is a silencing cassette targeting one or more genes selected from the group consisting of asparagine synthase 1 (Asn1), polyphenol oxidase (Ppo), and vacuolar invertase (Inv) genes. In an even more preferred aspect of the invention, the first binary vector further comprises a late blight resistance gene Vnt1 operably linked to its native promoter and terminator sequences.

In a different embodiment, the invention provides a transformed plant comprising in its genome an endogenous Ubi7 promoter operably linked to a desired exogenous nucleotide sequence operably linked to an exogenous terminator sequence. In one aspect of the invention, the expression of one or more genes selected from the group consisting of asparagine synthase 1 (Asn1), polyphenol oxidase (Ppo), and vacuolar invertase (Inv) genes in the transformed plant is down-regulated. In a preferred aspect of the invention, the plant further expresses a late blight resistance gene Vnt1.

In one embodiment, the transformed plant is a tuber-bearing plant. In a preferred embodiment, the tuber-bearing plant is a potato plant. Preferably, the transformed plant has a phenotype characterized by one or more of late blight resistance, black spot bruise tolerance, reduced cold-induced sweetening and reduced asparagine levels in its tubers.

In yet another embodiment, the invention provides a heat-processed product of the transformed plant of the invention. Preferably, the heat-processed product is a French fry, chip, crisp, potato, dehydrated potato or baked potato. In a preferred aspect of the invention, the heat-processed product has a lower level of acrylamide than a heat-processed product of a non-transformed plant of the same species.

In a different embodiment, the invention provides a modified TAL effector designed to bind to a desired sequence comprising (a) a truncated C-terminal activation domain comprising a catalytic domain; (b) a codon-optimized target sequence binding domain; and (c) an N-terminal region comprising a nuclear localization sequence. In a preferred aspect of the invention, the modified TAL effector is designed to bind the desired sequence within an intron of potato's ubiquitin-7 (Ubi7) gene. As such, the modified TAL effector comprises (a) a catalytic domain in the C-terminal activation domain comprising a Fok1 endonuclease; (b) a target sequence binding domain comprising 16.5 repeat variable diresidues corresponding to the Ubi7 5'-untranslated intron sequence; and (c) a SV40 nuclear localization sequence in the N-terminal region.

In yet another embodiment, the invention provides a binary vector comprising (a) a right border; (b) a forward expression cassette and a reverse expression cassette, each comprising a modified TAL effector according to claim 16 operably linked to a strong constitutive promoter and a terminator sequence; and (c) a sequence encoding an enzyme involved in cytokinine production, such as isopentenyl transferase (ipt).

In yet another embodiment, the invention provides a DNA construct comprising a promoter-less cassette comprising (a) a right border sequence linked to (b) a partial Ubi7 5'-untranslated intron sequence; (c) an Ubi7 monomer-encoding sequence fused to a mutated acetolactate synthase (ALS) gene; (d) a desired nucleotide sequence; (e) a terminator sequence; and (f) a left border, wherein the desired nucleotide sequence is not operably linked to a promoter. In a preferred aspect of the invention, the desired nucleotide sequence in the DNA construct is a silencing cassette targeting one or more genes selected from the group consisting of asparagine synthase 1 (Asn1), polyphenol oxidase (Ppo), and vacuolar invertase (Inv) genes. In an even more preferred aspect, the DNA construct further comprises a late blight resistance gene Vnt1 operably linked to its native promoter and terminator sequences.

In a different embodiment, the invention provides a kit for targeted insertion of exogenous DNA into a plant comprising: (A) a first binary vector comprising a promoter-less cassette comprising (a) a right border sequence linked to (b) a partial sequence of the Ubi7 intron 5'-untranslated region; (c) an Ubi7 monomer-encoding sequence fused to a mutated acetolactate synthase (ALS) gene; (d) a desired nucleotide sequence; and (e) a terminator sequence, wherein the desired nucleotide sequence is not operably linked to a promoter; and (B) a second binary vector comprising (a) a right border; (b) a forward expression cassette and a reverse expression cassette, each comprising a modified TAL effector operably linked to a strong constitutive promoter, and a terminator sequence; and (c) a sequence encoding isopentenyl transferase (ipt).

In a preferred aspect of the invention, the modified TAL effector is designed to bind the desired nucleotide sequence within an intron of potato'subiquitin-7 (Ubi7) gene, and comprises (a) a truncated C-terminal activation domain comprising a Fok1 endonuclease catalytic domain; (b) a codon-optimized target sequence binding domain comprising 16.5 repeat variable diresidues corresponding to the Ubi7 5'-untranslated intron sequence; and (c) an N-terminal region comprising a SV40 nuclear localization sequence. In another preferred aspect of the invention, the desired nucleotide sequence is a silencing cassette targeting one or more genes selected from the group consisting of asparagine synthase 1 (Asn1), polyphenol oxidase (Ppo), and vacuolar invertase (Inv) genes. In an even more preferred aspect of the invention, the first binary vector further comprises a late blight resistance gene Vnt1 operably linked to its native promoter and terminator sequences.

The foregoing general description and the following detailed description are exemplary and explanatory and are intended to provide further explanation of the invention as claimed. Other objects, advantages and novel features will be readily apparent to those skilled in the art from the following detailed description of the invention.

BRIEF DESCRIPTION OF THE DRAWINGS

FIG. 1 discloses SEQ ID NO: 22.

FIG. 5 shows the organization of the forward (5A) and reverse (5B) effector proteins (SEQ ID NOS 7 and 9, respectively).

FIG. 6 discloses SEQ ID NO: 23.

FIG. 8 shows the sequence of PCR-amplified target region of the plasmid pSIM2167 after co-infiltration with the TAL effector vector pSIM2170. Effector recognition site is gray highlighted. Modifications on target sequence are small deletion (majority form) and substitutions (dark gray highlighted). FIG. 8 discloses SEQ ID NOS 24-37, respectively, in order of appearance.

FIG. 9 shows the sequences of fragments from targeted insertion-specific PCR. The first non-highlighted sequence and the first light gray highlighted sequence are potato genome sequences. non highlighted sequence: part of Uni7-like promoter; light gray highlighted sequence: Uni7-like intron. The remaining sequences are from the pSIM2168 vector. Dark gray sequence: part of Ubi7 intron; non-highlighted sequence: Ubi7 monomer; light gray highlighted sequence: part of the ALS coding sequence. FIG. 9 discloses SEQ ID NOS 38-40, respectively, in order of appearance.

FIG. 11 shows Ranger Russet control (RR-C) lines and herbicide-resistant Ranger Russet lines co-transformed with the pSIM2170 and pSIM2168 plasmids for targeted insertion, challenged with P. infestans late blight strain US8 BF6 for the development of disease symptoms, at seven days after infection.

FIG. 17 shows yields of transformed potato lines.

FIG. 18 discloses SEQ ID NOS 41-42, respectively, in order of appearance.

FIG. 20 shows sequence of PCR amplified target region of plasmid pSIM2167 after co-infiltrated with pSIM4187. Target specific sequence in gRNA is dark green highlighted. Modifications on target sequence are small deletion and substitutions. FIG. 20 discloses SEQ ID NOS 43-51, respectively, in order of appearance.

DETAILED DESCRIPTION OF THE INVENTION

Figure 1:
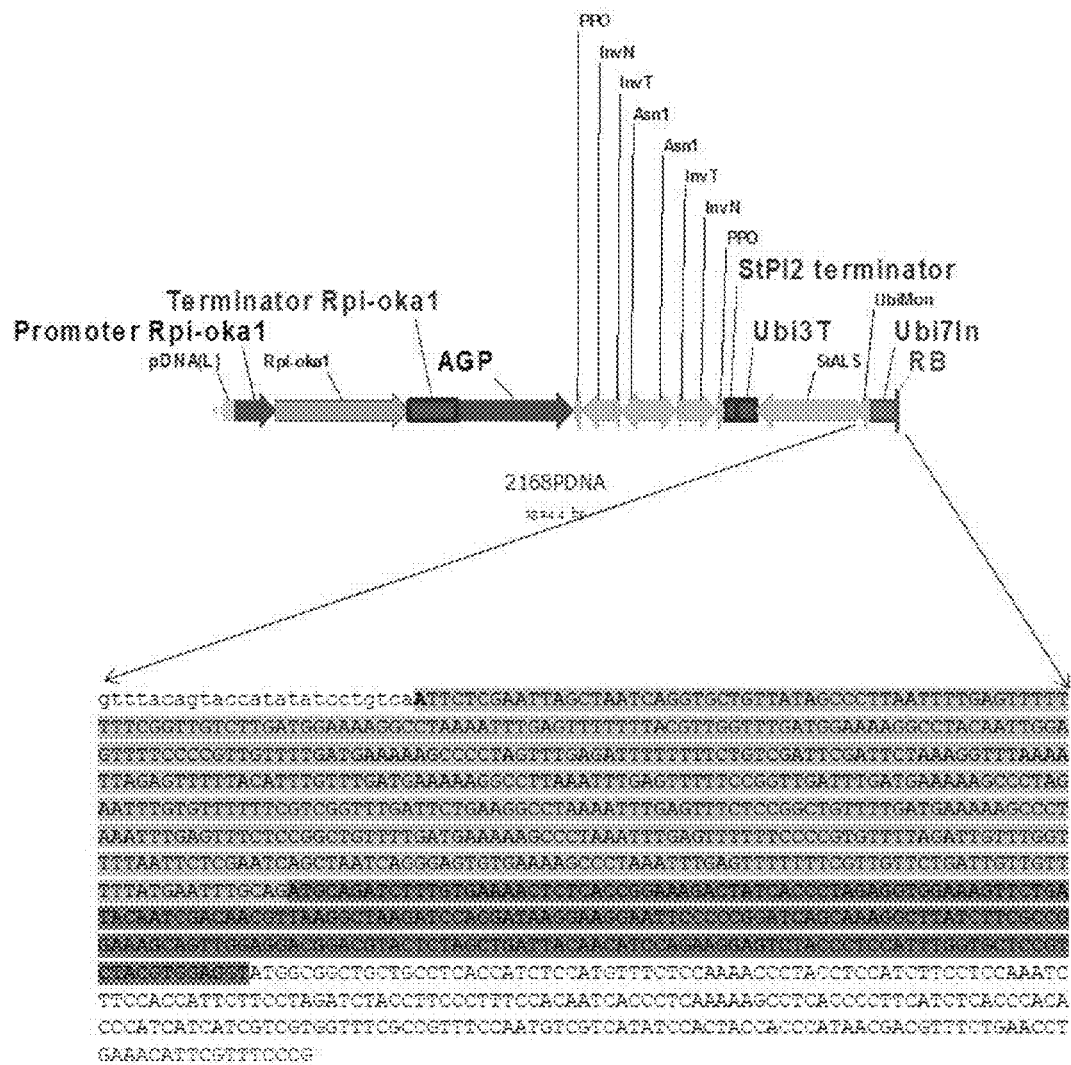
FIG. 1 illustrates the transfer DNA organization of the plasmid pSIM2168. Sequence shown in bottom panel starts from the 25 bp unhighlighted right border. The light gray highlighted sequence is part of the Ubi7 intron, the dark gray highlighted sequence is the Ubi7 monomer and the remaining unhighlighted sequence is part of the potato ALS gene coding. The Ubi7In segment of pSIM2168 comprises a homologous arm which is homologous to the endogenous intron sequence selectively cut by TAL.

One aspect of the present invention is the transient expression of transcription activator-like effector proteins designed to bind to, and consequently cut, a desired genomic target locus, thereby facilitating the insertion of a desired polynucleotide at that particular target locus. Accordingly, the present invention encompasses the transformation of plant material with a vector that contains an expression cassette encoding peptides or proteins that form appropriate TAL dimers that recognize and cleave a target locus, and a second vector that comprises one or more desired expression cassettes. Such desired expression cassettes may encode a particular protein or gene silencing transcript. In one embodiment, the second vector may comprise a cassette referred to herein as a "promoter-free" cassette, which comprises (i) a marker gene or gene that encodes a desired phenotype, and appropriate other regulatory elements that would facilitate appropriate expression of that marker gene if it was operably linked to a promoter; and (ii) a nucleotide region homologous to the endogenous target locus site destination. Said homologous nucleotide region can comprise, for example, 10-20, 20-50, or 20-100 nucleotides, that share 100%, or at least 99%, or at least 98%, or at least 97%, or at least 96%, or at least 95%, or at least 94%, or at least 93%, or at least 92%, or at least 91%, or at least 90%, or at least 89%, or at least 88%, or at least 87%, or at least 86%, or at least 85%, or at least 84%, or at least 83%, or at least 82%, or at least 81%, or at least 80%, or at least 79%, or at least 78%, or at least 77%, or at least 76%, or at least 75%, or at least 74%, or at least 73%, or at least 72%, or at least 71%, or at least 70%, or at least 69%, or at least 68%, or at least 67%, or at least 66%, or at least 65%, or at least 64%, or at least 63%, or at least 62%, or at least 61%, or at least 60%, or at least 59%, or at least 58%, or at least 57%, or at least 56%, or at least 55%, or at least 54%, or at least 53%, or at least 52%, or at least 51%, or at least 50% nucleotide sequence identity with the corresponding sequence of the endogenous target locus.

Thus, in one embodiment, the second vector comprises at least (i) an expression cassette encoding a desired polynucleotide (such as one that encodes a protein or untranslatable RNA transcript, which RNA transcript may comprise a sense, an antisense, and/or an inverted repeat of a sequence of a target gene to be downregulated), and (ii) a promoter-free marker cassette that comprises a marker gene operably linked to a regulatory element such as a terminator or 3-untranslated region, along with the homologous target site region.

The promoter-free marker cassette and the expression cassette(s) of the second vector ideally travel together so that both become integrated into the target locus as a consequence of TAL-mediated activity (brought about by the other, TAL-encoding, vector). Ideally, the promoter-free cassette and the expression cassette(s) are integrated into a desired site at the target locus suitably near, e.g., downstream or upstream as the case may be, of one or more functional endogenous promoters or endogenous regulatory elements, such that the endogenous promoter or regulatory element expresses the marker gene of the promoter-free marker cassette in the second vector. The appropriate design of the TAL sequences to recognize such a target sequence downstream or upstream of an endogenous gene promoter or regulatory element that initiates gene expression, such as an enhancer element, is therefore important in helping to ensure that the expression cassette(s) and promoter-free marker cassette are integrated at a particularly chosen genomic location time and again between different transformation events.

Therefore, the present invention permits site-specific insertion of a desired polynucleotide such as one of the cassettes disclosed herein and as described elsewhere, which ensures consistency in the expression or downregulation level of a particular target gene between different transformation events. For example, the site-specific insertion of the desired polynucleotide could function to express de novo or overexpress a target gene. In some embodiments, the levels of de novo expression or overexpression of the target gene might vary among different transformation events for no more than 200%, or no more than 100%, or no more than 50%, or no more than 30%. Alternatively, the site-specific insertion of the desired polynucleotide could function to produce an RNA transcript to downregulate a target gene. In some embodiments, the levels of downregulation of the target gene might vary among different transformation events for no more than 200%, or no more than 100%, or no more than 50%, or no more than 30%.

The marker gene is important because if the promoter-free marker cassette is appropriately integrated, the marker gene will be expressed by the endogenous regulatory element, and depending on the type of marker will (a) effectively identify successful transformants, and (b) give a preliminary indication of the successful insertion of the co-joined expression cassette(s) at the desired target location. Thus, if the marker gene is a herbicide resistant gene, the transformed plant cells may be cultured on the relevant herbicide and cells that survive reflect those that are transformed with the herbicide resistance gene at the desired target locus near a functional endogenous promoter.

Thus, the ability to routinely insert an expression cassette at the same genomic locus between different transformation events is highly desirable and advantageous and cost-effective because this reduces the magnitude of screens needed to identify integration events that would otherwise occur randomly in different genomic environments. See, e.g., Example 14. Those differences in random integration loci can often disrupt the local genomic environment detrimentally, knock-out essential genes, or place the desired expression cassettes in loci that fail to express the integrated DNA.

Accordingly, the homologous target site region present in the promoter-free marker cassette of the second vector is specifically designed to match up with the endogenous target site sequence that the TAL protein dimer of the first vector is also designed to recognize, bind to, and cut. The second vector may comprises one homologous target site region upstream or downstream of the polynucleotide sequences to be inserted, or two homologous target site regions flanking of the polynucleotide sequences to be inserted. Thus, both the promoter-free marker cassette and the TAL expression cassette contain sequences unique to the endogenous genomic target locus, such that the promoter-free marker cassette and its co-joined desired expression cassettes, is inserted into the precise target locus site cut by the TALs.

The present invention is not limited to the insertion of promoter-free marker cassettes and expression cassettes into a genomic locus or nearby an endogenous promoter or regulatory element. Rather, the present invention encompasses the use of the inventive method to stack cassettes in a modular fashion based upon the design of TAL sequences and homologous regions that recognize polynucleotide sequences from prior transformation events. That is, in one embodiment, a plant may have already been stably transformed with Expression Cassette A that, with or without the use of TAL, expresses Gene X at a particular or random site in the plant genome. The present TAL-mediated integration method allows for the design of TAL sequences that recognize a sequence perhaps downstream of Gene X in Expression Cassette A, such that the TAL dimer effectively cleaves the plant genome at that Gene X site. If the promoter-free marker cassette—or any expression cassette—comprises a homologous region to that Gene X site, then it is possible to introduce that cassette immediately downstream of Gene X. As mentioned, it is not necessary that in all cases the present invention must utilize a promoter-free marker system for it may be the case that the gene-of-interest integrated downstream of the pre-transformed Gene X plant produces a detectable and desired trait in and of itself. Furthermore, the additional expression cassette may contain its own promoter or may be promoter-free such that the gene-of-interest is expressed from the promoter or regulatory element of Expression Cassette A.

Accordingly, in one embodiment, the present invention encompasses the de novo insertion of a desired expression cassette into a target locus using the promoter-free marker design to identify successful and appropriate transformants. In another embodiment, the present invention encompasses the subsequent insertion of one or more additional expression cassettes, which may or may not include a promoter-free marker cassette, downstream or upstream of a prior integration event. Thus, in the latter approach, the present invention permits the ability to stack genes at precise and defined locations within a plant genome by effectively linking together different expression cassettes even though this is done via different transformations, using TAL-mediated site-specific insertion technology described herein.

In one embodiment, it is desirable to only transiently express the TAL proteins such that the only DNA that becomes stably integrated into the plant genome belongs to the desired expression cassette(s) and promoter-free marker cassette, if used.

Figure 2:
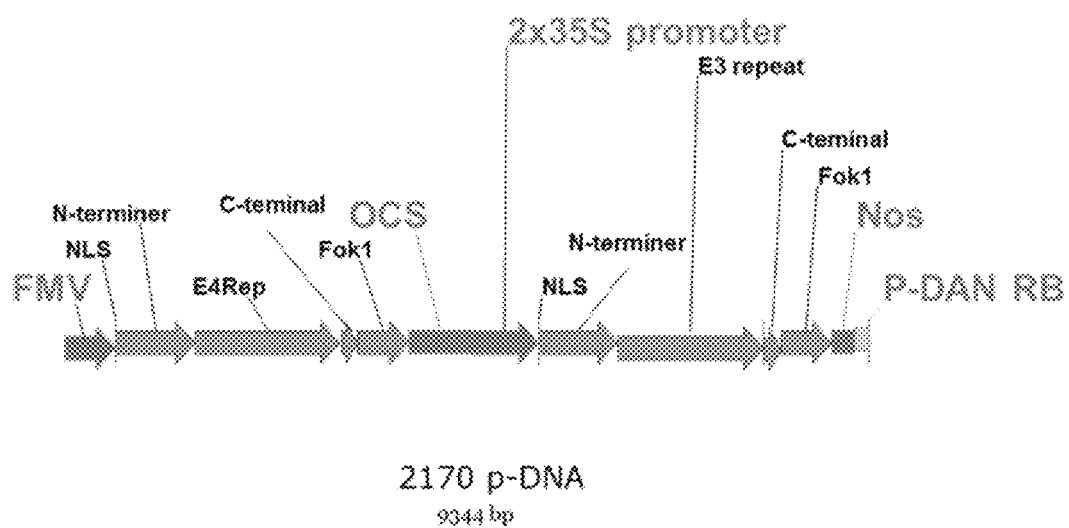
FIG. 2 illustrates the forward (E3) and reverse (E4) TAL effector cassettes in the vector pSIM2170.

Accordingly, one aspect of the present invention encompasses (1) identifying in the genome of a plant a desired target locus sequence; (2) designing corresponding TAL sequences that specifically recognize that target locus sequence; and, optionally, (3) assaying the designed TAL sequences in an infiltration assay, for instance, to test if the corresponding TAL dimer, when formed, cuts appropriately. TALs that work can then be subcloned into a transient expression transformation vector, such as shown in FIG. 2. Such steps are described in detail herein. See for instance Examples 10 and 11.

A second vector can then be designed comprising one or more desired expression cassettes along with the promoter-free marker cassette, and both the TAL vector and the second vector subsequently transformed into one or two strains of *Agrobacteria*.

Plant material, such as explants, calli, cells, leaves, or stems, can then be transformed using these *Agrobacteria*. In one embodiment, the transformed plant material can be grown into calli on media that does not contain any selection component. That is, for the ease of illustration, if the second vector comprises a herbicide resistance marker gene that is not operably linked to a promoter, then the transformed plant material would initially be cultured on media that does not contain herbicide for a certain period of time. After that period of time, the plant material may be placed on callus induction media that does contain herbicide. Those materials that survive can then be placed on shoot induction media that also contains the same herbicide until shoots develop and survive for a period of time. The shoots that grow on herbicide media are therefore likely to contain the stably integrated herbicide resistance gene in their genomes along with the actual desired expression cassettes. Those herbicide-resistant shoots or leaves that grow from those shoots can then be subjected to PCR and other molecular analyses to determine if they contain the marker and also the desired expression cassette(s) in the correct and expected genomic target location. This method is described herein in detail, see for instance Example 4. When the ALS gene was used as the marker gene in the promoter-free arrangement, as discussed herein, 80% of the analyzed transformed shoots/leaves contained the desired insert stably integrated in the desired genomic locus.

In one embodiment, the second vector comprises the gene expression cassette for late blight and a gene silencing cassette for silencing PPO, ASN1, and invertase, in addition to a promoter-free ALS herbicide marker gene, as shown in pSIM2168 (FIG. 1). In this case, the ALS gene is not operably linked to a promoter but it is operably linked to a terminator and includes, upstream, a sequence homologous to a region of the endogenous plant Ubi7 gene intron and part of the Ubi7 exon #1. FIG. 2 depicts the corresponding vector (pSIM2170) that expresses the E4Rep and E3 repeat TAL sequences that are also designed to recognize a naturally-occurring sequence within the Ubi7 gene intron. Both pSIM2168 and pSIM2170 are transformed into potato stem explants and subjected to the method described above and as described in methodological detail in the Examples provided herein. The results show that the inventive approach was successful in using TAL-mediated integration to stably integrate the cassettes of pSIM2168 into the precise target location desired in the endogenous Ubi7 gene intron.

The present inventive methods are not limited to the introduction of such vectors using transfer-DNAs or *Agrobacterium*. It is possible to use particle bombardment, for instance, without any *Agrobacterium* or T-DNA components. In one embodiment, for instance, it is possible to coat particle bombardment particles with DNA encoding the desired expression cassette(s) and promoter-free marker cassette, and also coat the same particles with TAL proteins or TAL protein dimers. In this fashion therefore a particle may comprise both encoding DNA and TAL proteins, or some particles may be coated with either the encoding DNA or the TAL proteins. In any event, plant material can be bombarded with such coated particles whereupon when the particles enter the plant cell, the TAL proteins function as intended to cut the genomic sequence at a desired site and integrate the co-delivered DNA. See for instance Martin-Ortigosa et al., Adv. Funct. Mater. 22, 3576-3582 (2012), which is incorporated herein by reference, for examples of how to use particle bombardment to co-deliver proteins and DNA into plants.

As used herein, a "desired polynucleotide" is essentially any polynucleotide or series of DNA sequences within an expression cassette or gene silencing cassette that the user desires to be integrated into the plant genome. Accordingly, "desired polynucleotide" may be used interchangeably with "cassette" "expression cassette" or "silencing cassette" herein. A desired polynucleotide in any expression cassette can be operably linked to any kind or strength of promoter and its expression is not necessarily therefore dependent on the expression of an endogenous plant genomic promoter.

While it is desirable to stably transform plant genomes according to the present TAL-mediated integration technology, another embodiment of the inventive methods encompasses the integration of a desired polynucleotide into any form or sample of nucleic acid, not TALs Transcription activator-like (TAL) effectors are plant pathogenic bacterial proteins that contain modular DNA binding domains that facilitate site-specific integration of DNAs into a particularly desired target site, such as in a plant genome. These domains comprise tandem, polymorphic amino acid repeats that individually specify contiguous nucleotides in DNA that are useful for directing the targeted site-specific integration approach.

A central repeat domain may comprise between 1.5 and 33.5 repeats typically 34 residues in length. An example of a repeat sequence is:

```
                                         (SEQ ID NO: 21)
    LTPEQVVAIASHDGGKQALETVQRLLPVLCQAHG.
```

The residues at the 12th and 13th positions can be hypervariable known as the "repeat variable diresidue" or RVD. There is a relationship between the identity of these two residues in sequential repeats and sequential DNA bases in the TAL effector's target site. The code between RVD sequence and target DNA base can be expressed as:

NI=A
HD=C
NG=T
NN=R (G or A), and
NS=N (A, C, G, or T).

RVD NK can target G, but TAL effector nucleases (TAL-ENs) that exclusively use NK instead of NN to target G can be less active.

Target sites of TAL effectors may include a T flanking the 5'-base targeted by the first repeat perhaps due to a contact between this T nucleotide and a conserved tryptophan in the region N-terminal of the central repeat domain.

See also the following publications which are all incorporated herein by reference in their entirety: Boch J, Bonas U (September 2010). "XanthomonasAvrBs3 Family-Type III Effectors: Discovery and Function". Annual Review of Phytopathology 48: 419-36; Voytas D F, Joung J K (December 2009). "Plant science. DNA binding made easy". Science 326 (5959): 1491-2. Bibcode 2009; Moscou M J, Bogdanove A J (December 2009). "A simple cipher governs DNA recognition by TAL effectors". Science 326 (5959): 1501; Boch J, Scholze H, Schornack S et al. (December 2009). "Breaking the code of DNA binding specificity of TAL-type III effectors". Science 326 (5959): 1509-12; Morbitzer, R.; Romer, P.; Boch, J.; Lahaye, T. (2010). "Regulation of selected genome loci using de novo-engineered transcription activator-like effector (TALE)-type transcription factors". Proceedings of the National Academy of Sciences 107 (50): 21617-21622; Miller, J. C.; Tan, S.; Qiao, G.; Barlow, K. A.; Wang, J.; Xia, D. F.; Meng, X.; Paschon, D. E. et al. (2010). "A TALE nuclease architecture for efficient genome editing". Nature Biotechnology 29 (2): 14; Huang, P.; Xiao, A.; Zhou, M.; Zhu, Z.; Lin, S.; Zhang, B. (2011). "Heritable gene targeting in zebrafish using customized TALENs". Nature Biotechnology 29 (8): 699; and Mak, A. N.-S.; Bradley, P.; Cernadas, R. A.; Bogdanove, A. J.; Stoddard, B. L. (2012). "The Crystal Structure of TAL Effector PthXo1 Bound to Its DNA Target". Science. doi: 10.1126/science.1216211.

Markers

Examples of the categories of marker genes that can be used as disclosed herein in the promoter-free marker gene cassette include, but are not limited to, herbicide tolerance, pesticide tolerance insect resistance, tolerance to stress, enhanced flavor or stability of the fruit or seed, or the ability to synthesize useful, non-plant proteins, e.g., medically valuable proteins or the ability to generate altered concentrations of plant proteins, and related impacts on the plant, e.g., altered levels of plant proteins catalyzing production of plant metabolites including secondary plant metabolites.

This invention provides methods and kits for the targeted insertion of desired nucleotide sequences into plants, by inserting promoter-less desired nucleotide sequences into the intron sequence of the ubiquitin-7 (Ubi7) gene, such that the expression of exogenous nucleotide sequences in the plants is driven by the endogenous Ubi7 promoter. In particular, the inventors were able to create binary vectors for the transient expression of transcription activator-like effector nucleases specifically designed to bind desired nucleotide sequences within the intron sequence of the Ubi7 gene, such that when these vectors are introduced into plant cells together with binary vectors carrying the targeted promoter-less nucleotide sequences, the desired nucleotide sequences are inserted into the intron sequence of the Ubi7 gene with proper orientation and spacing, and their expression is driven by the endogenous Ubi7 promoter. The transformed plants regenerating from the transformed explants thus obtained carry only the targeted sequences.

The invention further provides plants transformed by the methods of the invention, as well as the binary vectors for transient and permanent transformation.

The technology strategy of the present invention addresses the need to efficiently produce genetically engineered plants and plant products with desirable traits by targeted transformation, such that the nutritional value and agronomic characteristics of plant crops, and in particular tuber-bearing plants, such as potato plants, may be improved. Desirable traits include, but are not limited to, high tolerance to impact-induced black spot bruise, reduced formation of the acrylamide precursor asparagine, reduced accumulation of reducing sugars and reduced accumulation of toxic Maillard products, including acrylamide. Thus, the present invention allows the targeted insertion of these desirable traits into a plant genome by reducing the expression of enzymes, such as polyphenol oxidase (PPO), which is responsible for black spot bruise, and asparagine synthetase-1 (Asn-1), which is responsible for the accumulation of asparagine, a precursor in acrylamide formation, and by increasing the expression of the late blight resistance gene Vnt1.

The present invention uses terms and phrases that are well known to those practicing the art. Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described herein are those well known and commonly employed in the art. Standard techniques are used for recombinant nucleic acid methods, polynucleotide synthesis, microbial culture, cell culture, tissue culture, transformation, transfection, transduction, analytical chemistry, organic synthetic chemistry, chemical syntheses, chemical analysis, and pharmaceutical formulation and delivery. Generally, enzymatic reactions and purification and/or isolation steps are performed according to the manufacturers' specifications. The techniques and procedures are generally performed according to conventional methodology (Molecular Cloning, A Laboratory Manual, 3rd. edition, edited by Sambrook & Russel Cold Spring Harbor Laboratory Press, Cold Spring Harbor, N.Y., 2001).

*Agrobacterium* or bacterial transformation: as is well known in the field, *Agrobacteria* that are used for transforming plant cells are disarmed and virulent derivatives of, usually, *Agrobacterium tumefaciens* or *Agrobacterium rhizogenes*. Upon infection of plants, explants, cells, or protoplasts, a single *Agrobacterium* strain containing a binary vector comprising a TAL effector cassette and a binary vector comprising the gene of interest, or two separate *Agrobacterium* strains, one containing a binary vector comprising a TAL effector cassette, and the other containing a binary vector comprising the gene of interest, transfer a desired DNA segment from a plasmid vector to the plant cell nucleus. The vector typically contains a desired polynucleotide that is located between the borders of a T-DNA. However, any bacteria capable of transforming a plant cell may be used, such as, *Rhizobium trifolii, Rhizobium leguminosarum, Phyllobacterium myrsinacearum, SinoRhizobium meliloti*, and *MesoRhizobium loti*. The present invention is not limited to the use of bacterial transformation systems. Any organism however that contains the appropriate cellular machinery and proteins to accomplish plant cell transformation.

Angiosperm: vascular plants having seeds enclosed in an ovary. Angiosperms are seed plants that produce flowers that bear fruits. Angiosperms are divided into dicotyledonous and monocotyledonous plant.

Antibiotic Resistance: ability of a cell to survive in the presence of an antibiotic. Antibiotic resistance, as used herein, results from the expression of an antibiotic resistance gene in a host cell. A cell may have resistance to any antibiotic. Examples of commonly used antibiotics include kanamycin and hygromycin.

Dicotyledonous plant (dicot): a flowering plant whose embryos have two seed halves or cotyledons, branching leaf veins, and flower parts in multiples of four or five. Examples of dicots include but are not limited to, potato, sugar beet, broccoli, cassava, sweet potato, pepper, poinsettia, bean, alfalfa, soybean, and avocado.

Endogenous: nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species.

Expression cassette: polynucleotide that may comprise, from 5' to 3', (a) a first promoter, (b) a sequence comprising (i) at least one copy of a gene or gene fragment, or (ii) at least one copy of a fragment of the promoter of a gene, and (c) either a terminator or a second promoter that is positioned in the opposite orientation as the first promoter.

Foreign: "foreign," with respect to a nucleic acid, means that that nucleic acid is derived from non-plant organisms, or derived from a plant that is not the same species as the plant to be transformed or is not derived from a plant that is not interfertile with the plant to be transformed, does not belong to the species of the target plant. According to the present invention, foreign DNA or RNA represents nucleic acids that are naturally occurring in the genetic makeup of fungi, bacteria, viruses, mammals, fish or birds, but are not naturally occurring in the plant that is to be transformed. Thus, a foreign nucleic acid is one that encodes, for instance, a polypeptide that is not naturally produced by the transformed plant. A foreign nucleic acid does not have to encode a protein product.

Gene: A gene is a segment of a DNA molecule that contains all the information required for synthesis of a product, polypeptide chain or RNA molecule that includes both coding and non-coding sequences. A gene can also represent multiple sequences, each of which may be expressed independently, and may encode slightly different proteins that display the same functional activity. For instance, the asparagine synthetase 1 and 2 genes can, together, be referred to as a gene.

Genetic element: a "genetic element" is any discreet nucleotide sequence such as, but not limited to, a promoter, gene, terminator, intron, enhancer, spacer, 5'-untranslated region, 3'-untranslated region, or recombinase recognition site.

Genetic modification: stable introduction of DNA into the genome of certain organisms by applying methods in molecular and cell biology.

Gymnosperm: as used herein, refers to a seed plant that bears seed without ovaries. Examples of gymnosperms include conifers, cycads, ginkgos, and ephedras.

Introduction: as used herein, refers to the insertion of a nucleic acid sequence into a cell, by methods including infection, transfection, transformation or transduction.

Monocotyledonous plant (monocot): a flowering plant having embryos with one cotyledon or seed leaf, parallel leaf veins, and flower parts in multiples of three. Examples of monocots include, but are not limited to maize, rice, oat, wheat, barley, and sorghum.

Native: nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species.

Native DNA: any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. For instance, a native DNA may comprise a point mutation since such point mutations occur naturally. It is also possible to link two different native DNAs by employing restriction sites because such sites are ubiquitous in plant genomes.

Native Nucleic Acid Construct: a polynucleotide comprising at least one native DNA.

Operably linked: combining two or more molecules in such a fashion that in combination they function properly in a plant cell. For instance, a promoter is operably linked to a structural gene when the promoter controls transcription of the structural gene.

Overexpression: expression of a gene to levels that are higher than those in control plants.

P-DNA: a plant-derived transfer-DNA ("P-DNA") border sequence of the present invention is not identical in nucleotide sequence to any known bacterium-derived T-DNA border sequence, but it functions for essentially the same purpose. That is, the P-DNA can be used to transfer and integrate one polynucleotide into another. A P-DNA can be inserted into a tumor-inducing plasmid, such as a Ti-plasmid from *Agrobacterium* in place of a conventional T-DNA, and maintained in a bacterium strain, just like conventional transformation plasmids. The P-DNA can be manipulated so as to contain a desired polynucleotide, which is destined for integration into a plant genome via bacteria-mediated plant transformation. The P-DNA comprises at least one border sequence. See Rommens et al. 2005 *Plant Physiology* 139: 1338-1349, which is incorporated herein by reference. In certain embodiments of the invention, the T-DNA is replaced by the P-DNA.

Phenotype: phenotype is a distinguishing feature or characteristic of a plant, which may be altered according to the present invention by integrating one or more "desired polynucleotides" and/or screenable/selectable markers into the genome of at least one plant cell of a transformed plant. The "desired polynucleotide(s)" and/or markers may confer a change in the phenotype of a transformed plant, by modifying any one of a number of genetic, molecular, biochemical, physiological, morphological, or agronomic characteristics or properties of the transformed plant cell or plant as a whole.

Plant tissue: a "plant" is any of various photosynthetic, eukaryotic, multicellular organisms of the kingdom Plantae characteristically producing embryos, containing chloroplasts, and having cellulose cell walls. A part of a plant, i.e., a "plant tissue" may be treated according to the methods of the present invention to produce a transgenic plant. Many suitable plant tissues can be transformed according to the present invention and include, but are not limited to, somatic embryos, pollen, leaves, stems, calli, stolons, microtubers, and shoots. Thus, the present invention envisions the transformation of angiosperm and gymnosperm plants such as wheat, maize, rice, barley, oat, sugar beet, potato, tomato, alfalfa, cassava, sweet potato, and soybean. According to the present invention "plant tissue" also encompasses plant cells. Plant cells include suspension cultures, callus, embryos, meristematic regions, callus tissue, leaves, roots, shoots, gametophytes, sporophytes, pollen, seeds and microspores. Plant tissues may be at various stages of maturity and may be grown in liquid or solid culture, or in soil or suitable media in pots, greenhouses or fields. A plant tissue also refers to any clone of such a plant, seed, progeny, propagule whether generated sexually or asexually, and descendents of any of these, such as cuttings or seed. Of particular interest are potato, maize, and wheat.

Plant transformation and cell culture: broadly refers to the process by which plant cells are genetically modified and transferred to an appropriate plant culture medium for maintenance, further growth, and/or further development. Such methods are well known to the skilled artisan.

Processing: the process of producing a food from (1) the seed of, for instance, wheat, corn, coffee plant, or cocoa tree, (2) the tuber of, for instance, potato, or (3) the root of for instance, sweet potato and yam comprising heating to at least 120° C. Examples of processed foods include bread, breakfast cereal, pies, cakes, toast, biscuits, cookies, pizza, pretzels, tortilla, French fries, oven-baked fries, potato chips, hash browns, roasted coffee, and cocoa.

Progeny: a "progeny" of the present invention, such as the progeny of a transgenic plant, is one that is born of, begotten by, or derived from a plant or the transgenic plant. Thus, a "progeny" plant, i.e., an "F1" generation plant is an offspring or a descendant of the transgenic plant produced by the inventive methods. A progeny of a transgenic plant may contain in at least one, some, or all of its cell genomes, the desired polynucleotide that was integrated into a cell of the parent transgenic plant by the methods described herein. Thus, the desired polynucleotide is "transmitted" or "inherited" by the progeny plant. The desired polynucleotide that is so inherited in the progeny plant may reside within a T-DNA or P-DNA construct, which also is inherited by the progeny plant from its parent. The term "progeny" as used herein, also may be considered to be the offspring or descendants of a group of plants.

Promoter: promoter is intended to mean a nucleic acid, preferably DNA that binds RNA polymerase and/or other transcription regulatory elements. A promoter is a nucleic acid sequence that enables a gene with which it is associated to be transcribed. A regulatory region refers to nucleic acid sequences that influence and/or promote initiation of transcription. Promoters are typically considered to include regulatory regions, such as enhancer or inducer elements.

Eukaryotic promoters typically lie upstream of the gene to which they are most immediately associated. Promoters can have regulatory elements located several kilobases away from their transcriptional start site, although certain tertiary structural formations by the transcriptional complex can cause DNA to fold, which brings those regulatory elements closer to the actual site of transcription. Many eukaryotic promoters contain a "TATA box" sequence, typically denoted by the nucleotide sequence, TATAAA. This element binds a TATA binding protein, which aids formation of the RNA polymerase transcriptional complex. The TATA box typically lies within 50 bases of the transcriptional start site.

Eukaryotic promoters also are characterized by the presence of certain regulatory sequences that bind transcription factors involved in the formation of the transcriptional complex. An example is the E-box denoted by the sequence CACGTG, which binds transcription factors in the basic-helix-loop-helix family. There also are regions that are high in GC nucleotide content.

A polynucleotide may be linked in two different orientations to the promoter. In one orientation, e.g., "sense", at least the 5'-part of the resultant RNA transcript will share sequence identity with at least part of at least one target transcript. In the other orientation designated as "antisense", at least the 5'-part of the predicted transcript will be identical or homologous to at least part of the inverse complement of at least one target transcript.

A plant promoter is a promoter capable of initiating transcription in plant cells whether or not its origin is a plant cell. Exemplary plant promoters include, but are not limited to, those that are obtained from plants, plant viruses, and bacteria such as *Agrobacterium* or *Rhizobium* which comprise genes expressed in plant cells. Examples of promoters under developmental control include promoters that preferentially initiate transcription in certain tissues, such as xylem, leaves, roots, or seeds. Such promoters are referred to as tissue-preferred promoters. Promoters which initiate transcription only in certain tissues are referred to as tissue-specific promoters. A cell type-specific promoter primarily drives expression in certain cell types in one or more organs, for example, vascular cells in roots or leaves. An inducible or repressible promoter is a promoter which is under environmental control. Examples of environmental conditions that may effect transcription by inducible promoters include anaerobic conditions or the presence of light. Tissue specific, tissue preferred, cell type specific, and inducible promoters constitute the class of non-constitutive promoters. A constitutive promoter is a promoter which is active under most environmental conditions, and in most plant parts.

Polynucleotide is a nucleotide sequence, comprising a gene coding sequence or a fragment thereof, (comprising at least 15 consecutive nucleotides, preferably at least 30 consecutive nucleotides, and more preferably at least 50 consecutive nucleotides), a promoter, an intron, an enhancer region, a polyadenylation site, a translation initiation site, 5' or 3' untranslated regions, a reporter gene, a selectable marker or the like. The polynucleotide may comprise single stranded or double stranded DNA or RNA. The polynucleotide may comprise modified bases or a modified backbone. The polynucleotide may be genomic, an RNA transcript (such as an mRNA) or a processed nucleotide sequence (such as a cDNA). The polynucleotide may comprise a sequence in either sense or antisense orientations.

An isolated polynucleotide is a polynucleotide sequence that is not in its native state, e.g., the polynucleotide is comprised of a nucleotide sequence not found in nature or the polynucleotide is separated from nucleotide sequences with which it typically is in proximity or is next to nucleotide sequences with which it typically is not in proximity.

Seed: a "seed" may be regarded as a ripened plant ovule containing an embryo, and a propagative part of a plant, as a tuber or spore. Seed may be incubated prior to *Agrobacterium*-mediated transformation, in the dark, for instance, to facilitate germination. Seed also may be sterilized prior to incubation, such as by brief treatment with bleach. The resultant seedling can then be exposed to a desired strain of *Agrobacterium*.

Selectable/screenable marker: a gene that, if expressed in plants or plant tissues, makes it possible to distinguish them from other plants or plant tissues that do not express that gene. Screening procedures may require assays for expression of proteins encoded by the screenable marker gene. Examples of selectable markers include herbicide resistance genes, such as acetolactate synthase (ALS), the neomycin phosphotransferase (NptII) gene encoding kanamycin and geneticin resistance, the hygromycin phosphotransferase (HptII) gene encoding resistance to hygromycin, or other similar genes known in the art.

Sensory characteristics: panels of professionally trained individuals can rate food products for sensory characteristics such as appearance, flavor, aroma, and texture. Thus, the present invention contemplates improving the sensory characteristics of a plant product obtained from a plant that has been modified according to the present invention to manipulate its tuber yield production.

Sequence identity: as used herein, "sequence identity" or "identity" in the context of two nucleic acid or polypeptide sequences includes reference to the residues in the two sequences which are the same when aligned for maximum correspondence over a specified region. A homologous region or sequence as used herein therefore describes a sequence that shares some degree of sequence identity with a target genomic loci. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11 17 (1988) e.g., as implemented in the program PC/GENE (Intelligenetics, Mountain View, Calif., USA).

As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Sequence identity" has an art-recognized meaning and can be calculated using published techniques. See COMPUTATIONAL MOLECULAR BIOLOGY, Lesk, ed. (Oxford University Press, 1988), BIOCOMPUTING: INFORMATICS AND GENOME PROJECTS, Smith, ed. (Academic Press, 1993), COMPUTER ANALYSIS OF SEQUENCE DATA, PART I, Griffin & Griffin, eds., (Humana Press, 1994), SEQUENCE ANALYSIS 1N MOLECULAR BIOLOGY, Von Heinje ed., Academic Press (1987), SEQUENCE ANALYSIS PRIMER, Gribskov & Devereux, eds. (Macmillan Stockton Press, 1991), and Carillo & Lipton, SIAM J. Applied Math. 48: 1073 (1988). Methods commonly employed to determine identity or similarity between two sequences include but are not limited to those disclosed in GUIDE TO HUGE COMPUTERS, Bishop, ed., (Academic Press, 1994) and Carillo & Lipton, supra. Methods to determine identity and similarity are codified in computer programs. Preferred computer program methods to determine identity and similarity between two sequences include but are not limited to the GCG program package (Devereux et al., Nucleic Acids Research 12: 387 (1984)), BLASTP, BLASTN, FASTA (Atschul et al., J. Mol. Biol. 215: 403 (1990)), and FASTDB (Brutlag et al., Comp. App. Biosci. 6: 237 (1990)).

Silencing: The unidirectional and unperturbed transcription of either genes or gene fragments from promoter to terminator can trigger post-transcriptional silencing of target genes. Initial expression cassettes for post-transcriptional gene silencing in plants comprised a single gene fragment positioned in either the antisense (McCormick et al., U.S. Pat. No. 6,617,496; Shewmaker et al., U.S. Pat. No. 5,107,065) or sense (van der Krol et al., Plant Cell 2:291-299, 1990) orientation between regulatory sequences for transcript initiation and termination. In *Arabidopsis*, recognition of the resulting transcripts by RNA-dependent RNA polymerase leads to the production of double-stranded (ds) RNA. Cleavage of this dsRNA by Dicer-like (Dcl) proteins such as Dcl4 yields 21-nucleotide (nt) small interfering RNAs (siRNAs). These siRNAs complex with proteins including members of the Argonaute (Ago) family to produce RNA-induced silencing complexes (RISCs). The RISCs then target homologous RNAs for endonucleolytic cleavage.

More effective silencing constructs contain both a sense and antisense component, producing RNA molecules that fold back into hairpin structures (Waterhouse et al., Proc Natl Acad Sci USA 95: 13959-13964, 1998). The high dsRNA levels produced by expression of inverted repeat transgenes were hypothesized to promote the activity of multiple Dcls. Analyses of combinatorial Dcl knockouts in *Arabidopsis* supported this idea, and also identified Dcl4 as one of the proteins involved in RNA cleavage.

One component of conventional sense, antisense, and double-strand (ds) RNA-based gene silencing constructs is the transcriptional terminator. WO 2006/036739, which is incorporated in its entirety by reference, shows that this regulatory element becomes obsolete when gene fragments are positioned between two oppositely oriented and functionally active promoters. The resulting convergent transcription triggers gene silencing that is at least as effective as unidirectional 'promoter-to-terminator' transcription. In addition to short variably-sized and non-polyadenylated RNAs, terminator-free cassette produced rare longer transcripts that reach into the flanking promoter. Replacement of gene fragments by promoter-derived sequences further increased the extent of gene silencing.

TAL effectors (TALE) are proteins secreted by *Xanthomonas* bacteria characterized by the presence of a DNA binding domain that contains a repeated highly conserved 33-34 amino acid sequence, except for the highly variable 12th and 13th amino acids, which show a strong correlation with specific nucleotide recognition. These proteins can bind promoter sequences in the host plant and activate the expression of plant genes. This application makes use of engineered TAL effectors that are fused to the cleavage domain of Fok1 endonucleases for the targeted insertion of desirable genes into plants.

Tissue: any part of a plant that is used to produce a food. A tissue can be a tuber of a potato, a root of a sweet potato, or a seed of a maize plant.

Transcriptional terminators: The expression DNA constructs of the present invention typically have a transcriptional termination region at the opposite end from the transcription initiation regulatory region. The transcriptional termination region may be selected, for stability of the mRNA to enhance expression and/or for the addition of polyadenylation tails added to the gene transcription product. Translation of a nascent polypeptide undergoes termination when any of the three chain-termination codons enters the A site on the ribosome. Translation termination codons are UAA, UAG, and UGA. In the instant invention, transcription terminators are derived from either a gene or, more preferably, from a sequence that does not represent a gene but intergenic DNA. For example, the terminator sequence from the potato ubiquitin gene may be used.

Transfer DNA (T-DNA): a transfer DNA is a DNA segment delineated by either T-DNA borders or P-DNA borders to create a T-DNA or P-DNA, respectively. A T-DNA is a genetic element that is well-known as an element capable of integrating a nucleotide sequence contained within its borders into another genome. In this respect, a T-DNA is flanked, typically, by two "border" sequences. A desired polynucleotide of the present invention and a selectable marker may be positioned between the left border-like sequence and the right border-like sequence of a T-DNA. The desired polynucleotide and selectable marker contained within the T-DNA may be operably linked to a variety of different, plant-specific (i.e., native), or foreign nucleic acids, like promoter and terminator regulatory elements that facilitate its expression, i.e., transcription and/or translation of the DNA sequence encoded by the desired polynucleotide or selectable marker.

Transformation of plant cells: A process by which a nucleic acid is stably inserted into the genome of a plant cell. Transformation may occur under natural or artificial conditions using various methods well known in the art. Transformation may rely on any known method for the insertion of nucleic acid sequences into a prokaryotic or eukaryotic host cell, including *Agrobacterium*-mediated transformation protocols such as 'refined transformation' or 'precise breeding', viral infection, whiskers, electroporation, microinjection, polyethylene glycol-treatment, heat shock, lipofection and particle bombardment.

Transgenic plant: a transgenic plant of the present invention is one that comprises at least one cell genome in which an exogenous nucleic acid has been stably integrated. According to the present invention, a transgenic plant is a plant that comprises only one genetically modified cell and cell genome, or is a plant that comprises some genetically modified cells, or is a plant in which all of the cells are genetically modified. A transgenic plant of the present invention may be one that comprises expression of the desired polynucleotide, i.e., the exogenous nucleic acid, in only certain parts of the plant. Thus, a transgenic plant may contain only genetically modified cells in certain parts of its structure.

Variant: a "variant," as used herein, is understood to mean a nucleotide or amino acid sequence that deviates from the standard, or given, nucleotide or amino acid sequence of a particular gene or protein. The terms, "isoform," "isotype," and "analog" also refer to "variant" forms of a nucleotide or an amino acid sequence. An amino acid sequence that is altered by the addition, removal or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "non-conservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. "Variant" may also refer to a "shuffled gene" such as those described in Maxygen-assigned patents.

Although the present application primarily uses TAL to illustrate the targeted transfer DNA insertion technology, it is understood that other endonuclease based genome editing enzymes can also be used, including meganuclease (Epinat et al., *Nucleic Acids Res.* 31(11):2952-2962 (2003)), Zinc finger nuclease (ZFN) (Porteus et al., *Science* 300(5620):763 (2003); Bogdanove et al., *Science* 333(6051):1843-6 (2011)), and CRISPR-associated (Cas) endonuclease (Jinek et al., *Science* 337(6096):816-21 (2012); Mussolino et al., *Nat. Methods* 8(9):725-6 (2013)). In this regard, Example 15 illustrates the successful use of Cas9 for the targeted transfer DNA insertion technology described herein.

It is understood that the present invention is not limited to the particular methodology, protocols, vectors, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a gene" is a reference to one or more genes and includes equivalents thereof known to those skilled in the art and so forth. Indeed, one skilled in the art can use the methods described herein to express any native gene (known presently or subsequently) in plant host systems.

The following examples are set forth as representative of specific and preferred embodiments of the present invention. These examples are not to be construed as limiting the scope of the invention in any manner. It should be understood that many variations and modifications can be made while remaining within the spirit and scope of the invention.

Additional Embodiments

Embodiment 1—A method for stably integrating a desired polynucleotide into a plant genome, comprising:
(A) transforming plant material with a first vector comprising nucleotide sequences encoding TAL or CRISPR proteins designed to recognize a target sequence;
(B) transforming the plant material with a second vector comprising (i) a marker gene that is not operably linked to a promoter ("promoter-free marker cassette") and which comprises a sequence homologous to the target sequence; and (ii) a desired polynucleotide; and
(C) identifying transformed plant material in which the desired polynucleotide is stably integrated.
Embodiment 2—The method of Embodiment 1, wherein the transformed plant material is exposed to conditions that reflect the presence or absence of the marker gene in the transformed plant.
Embodiment 3—The method of any of Embodiments 1-2, wherein the marker gene is a herbicide resistance gene and the transformed plant material is exposed to herbicide.
Embodiment 4—The method of any of Embodiments 1-3, wherein the herbicide resistance gene is the ALS gene.
Embodiment 5—The method of any of Embodiments 1-4, wherein the promoter-free marker cassette is stably integrated into the plant genome.
Embodiment 6—A method for the targeted insertion of exogenous DNA into a plant comprising the steps of
(i) transforming isolated plant cells with
(A) a first binary vector comprising a promoter-less cassette comprising (a) a right border sequence linked to (b) a partial sequence of the Ubi7 intron 5'-untranslated region; (c) an Ubi7 monomer-encoding sequence fused to a mutated acetolactate synthase (ALS) gene; (d) a desired nucleotide sequence; and (e) a terminator sequence, wherein the desired nucleotide sequence is not operably linked to a promoter; and
(B) a second binary vector comprising (a) a right border; (b) a forward expression cassette and a reverse expression cassette, each comprising a modified TAL effector or Cas9 operably linked to a strong constitutive promoter, and a terminator sequence; and (c) a sequence encoding isopentenyl transferase (ipt), wherein the modified TAL effector or Cas9 is designed to bind the desired nucleotide sequence within an intron of potato'subiquitin-7 (Ubi7) gene; and
(ii) culturing the isolated plant cells under conditions that promote growth of plants that express the desired nucleotide sequence; wherein no vector backbone DNA is permanently inserted into the plant genome.
Embodiment 7—The method of Embodiment 6, wherein the modified TAL effector comprises (a) a truncated C-terminal activation domain comprising a Fok1 endonuclease catalytic domain; (b) a codon-optimized target sequence binding domain comprising 16.5 repeat variable diresidues corresponding to the Ubi7 5'-untranslated intron sequence; and (c) an N-terminal region comprising a SV40 nuclear localization sequence.
Embodiment 8—The method of any of Embodiments 6-7, wherein the desired nucleotide sequence is a silencing cassette targeting one or more genes selected from the group consisting of asparagine synthase 1 (Asn1), polyphenol oxidase (Ppo), and vacuolar invertase (Inv) genes.
Embodiment 9—The method of any of Embodiments 6-8, wherein the first binary vector further comprises a late blight resistance gene Vnt1 operably linked to its native promoter and terminator sequences.
Embodiment 10—A transformed plant comprising in its genome an endogenous Ubi7 promoter operably linked to a desired exogenous nucleotide sequence operably linked to an exogenous terminator sequence.
Embodiment 11—The transformed plant of Embodiment 10, wherein the expression of one or more genes selected from the group consisting of asparagine synthase 1 (Asn1), polyphenol oxidase (Ppo), and vacuolar invertase (Inv) genes is down-regulated.
Embodiment 12—The transformed plant of any of Embodiments 10-11, wherein the plant further expresses a late blight resistance gene Vnt1.
Embodiment 13—The transformed plant of any of Embodiments 10-12, wherein the plant is a tuber-bearing plant.
Embodiment 14—The transformed plant of any of Embodiments 10-13, wherein the tuber-bearing plant is a potato plant.
Embodiment 15—The transformed plant of any of Embodiments 10-14, wherein the plant has a phenotype characterized by one or more of late blight resistance, black spot bruise tolerance, reduced cold-induced sweetening and reduced asparagine levels in its tubers.
Embodiment 16—A heat-processed product of the transformed plant of any of Embodiments 10-15.

Embodiment 17—The heat-processed product of Embodiment 16, wherein the product is a French fry, chip, crisp, potato, dehydrated potato or baked potato.

Embodiment 18—The heat-processed product of Embodiments 16 or 17, wherein the heat-processed product has a lower level of acrylamide than a heat-processed product of a non-transformed plant of the same species.

Embodiment 19—A modified TAL effector designed to bind to a desired sequence comprising (a) a truncated C-terminal activation domain comprising a catalytic domain; (b) a codon-optimized target sequence binding domain designed to bind a 5'-untranslated intron sequence; and (c) an N-terminal region comprising a nuclear localization sequence.

Embodiment 20—The modified TAL effector of Embodiment 19, wherein the modified TAL effector is designed to bind the desired sequence within an intron of potato'subiquitin-7 (Ubi7) gene.

Embodiment 21—The modified TAL effector of Embodiment 19 or 20, wherein (a) the catalytic domain in the C-terminal activation domain comprises a Fok1 endonuclease; (b) the target sequence binding domain comprises 16.5 repeat variable diresidues corresponding to the Ubi7 5'-untranslated intron sequence; and (c) the nuclear localization sequence in the N-terminal region is a SV40 nuclear localization sequence.

Embodiment 22—A binary vector comprising (a) a right border; (b) a forward expression cassette and a reverse expression cassette, each encoding a modified TAL effector according to any of Embodiments 19-21 operably linked to a strong constitutive promoter and a terminator sequence; and (c) a sequence encoding isopentenyl transferase (ipt).

Embodiment 23—A DNA construct comprising a promoterless cassette comprising (a) a right border sequence linked to (b) a partial Ubi7 5'-untranslated intron sequence; (c) an Ubi7 monomer-encoding sequence fused to a mutated acetolactate synthase (ALS) gene; (d) a desired nucleotide sequence; (e) a terminator sequence; and (f) a left border, wherein the desired nucleotide sequence is not operably linked to a promoter.

Embodiment 24—The DNA construct of Embodiment 23, wherein the desired nucleotide sequence is a silencing cassette targeting one or more genes selected from the group consisting of asparagine synthase 1 (Asn1), polyphenol oxidase (Ppo), and vacuolar invertase (Inv) genes.

Embodiment 25—The DNA construct of Embodiment 23 or 24, wherein the DNA construct further comprises a late blight resistance gene Vnt1 operably linked to its native promoter and terminator sequences.

Embodiment 26—A kit for targeted insertion of exogenous DNA into a plant comprising:

(A) a first binary vector comprising a promoter-less cassette comprising (a) a right border sequence linked to (b) a partial sequence of the Ubi7 intron 5'-untranslated region; (c) an Ubi7 monomer-encoding sequence fused to a mutated acetolactate synthase (ALS) gene; (d) a desired nucleotide sequence; and (e) a terminator sequence, wherein the desired nucleotide sequence is not operably linked to a promoter; and (B) a second binary vector comprising (a) a right border; (b) a forward expression cassette and a reverse expression cassette, each comprising a modified TAL effector or Cas9 operably linked to a strong constitutive promoter, and a terminator sequence; and (c) a sequence encoding isopentenyl transferase (ipt), wherein the modified TAL effector or Cas9 is designed to bind the desired nucleotide sequence within an intron of potato'subiquitin-7 (Ubi7) gene.

Embodiment 27—The kit of Embodiment 26, wherein the modified TAL effector comprises (a) a truncated C-terminal activation domain comprising a Fok1 endonuclease catalytic domain; (b) a codon-optimized target sequence binding domain comprising 16.5 repeat variable diresidues corresponding to the Ubi7 5'-untranslated intron sequence; and (c) an N-terminal region comprising a SV40 nuclear localization sequence.

Embodiment 28—The kit of Embodiment 26 or 27, wherein the desired nucleotide sequence is a silencing cassette targeting one or more genes selected from the group consisting of asparagine synthase 1 (Asn1), polyphenol oxidase (Ppo), and vacuolar invertase (Inv) genes.

Embodiment 29—The kit of any of Embodiments 26-28, wherein the first binary vector further comprises a late blight resistance gene Vnt1 operably linked to its native promoter and terminator sequences.

Embodiment 30—A method for targeted insertion of a transfer DNA into a plant genome, comprising: transforming plant material with one or more vectors, which comprise:

a first genetic cassette encoding an endonuclease-based enzyme that selectively introduces a double-stranded DNA break within a 5' untranslated intron sequence of a targeted gene locus of the plant genome, and a second genetic cassette which (a) does not comprise a promoter, (b) comprises a desired gene sequence, and (c) comprises a homologous sequence that mediates homologous recombination-based repair of the double-stranded DNA break introduced by the endonuclease-based enzyme, and wherein the transformed plant material comprises the desired gene sequence selectively inserted in the targeted gene locus and operably linked to a promoter associated with the 5' untranslated intron sequence.

Embodiment 31—The method of Embodiment 30, wherein the endonuclease-based enzyme is TAL effector.

Embodiment 32—The method of Embodiment 30, wherein the endonuclease-based enzyme is Cas9.

Embodiment 33—The method of any of Embodiments 30-32, wherein the targeted gene locus is potato'subiquitin-7 (Ubi7) gene.

Embodiment 34—The method of any of Embodiments 30-33, further comprising selecting the transformed plant based on a phenotype conferred by the expression of the desired gene sequence inserted in targeted gene locus.

Embodiment 35—A transformed plant obtained by the method of any of Embodiments 30-34, comprising a modified plant genome which comprises, form 5' to 3', an endogenous promoter operably linked to an exogenous gene sequence operably linked to an exogenous terminator.

Embodiment 36—A vector suitable for the method of any of Embodiments 30-34, encoding a transfer DNA comprising a right border sequence linked to a promoter-less genetic cassette, wherein the promoter-less genetic cassette expresses a protein or an RNA transcript when inserted in the targeted gene locus and operably linked to a promoter associated with the 5' untranslated intron sequence.

EXAMPLES

Example 1

Method for Targeted Insertion

A preferred target site for gene insertion is within an intron positioned in the untranslated 5'-leader region of the potato'subiquitin-7 (Ubi7) gene. Potato is tetraploid and contains four copies of this gene; the copies are identical or near-identical. The Ubi7 genes are expressed at high levels in a near-constitutive manner, which suggests that they are located in regions that promote transcriptional activity. Sequences positioned within a transfer DNA are therefore expected to be effectively expressed. Furthermore, insertional inactivation of one of the Ubi7 genes is not expected to cause any quality or agronomic issues because potato still contains three functionally-active copies of the gene.

DNA segments were inserted into the intron sequence of the ubiquitin-7 gene according to the following steps:

(1) TAL effectors were designed to bind to sequences within the intron, which is (a) more than about 25-bp upstream from the region comprising branch site (consensus =CU(A/G)A(C/U)), pyrimidine-rich (=AT-rich) sequence, and intron/exon junction (consensus=CAGG), and (b) more than about 50-bp downstream from the splice donor site at the exon/intron junction (consensus=AGGT).

(2) A binary vector was created for transient expression of the TAL effectors in plant cells. This vector contains (a) a single right border but no left border; (b) two TAL effector genes operably linked to strong constitutive promoters; and (c) an expression cassette for the isopentenyl transferase (ipt) gene involved in cytokinin production. Stable transformation can be selected against because it would result in integration of the entire vector and, consequently, produce stunted shoots that overexpress cytokinins and are unable to produce roots.

(3) A second binary vector was created for stable transformation with a transfer DNA comprising genetic elements from potato delineated by borders: (a) right border; (b) part of the intron of the Ubi7 promoter, starting from the sequence between targeted TAL binding sites; (c) Ubi7 monomer-encoding sequence; (d) modified acetolactate synthase (ALS) gene that is insensitive to at least one ALS inhibitor selected from the group including sulfonylureas, imidazolinones, triazolopyrimidines, pyrimidinyl oxybenzoates, and sulfonylamino carbonyl triazolinones; (e) terminator of the ubiquitin-3 gene; (f) silencing cassette targeting the asparagine synthase 1 (Asn1), polyphenol oxidase (Ppo), and vacuolar invertase (Inv) genes; (g) late blight resistance gene Vnt1, operably linked to its native promoter and terminator sequences; and (h) left border. The vector backbone contains, apart from sequences required for maintenance and selection in *E. coli* and *A. tumefaciens*, an expression cassette for the ipt gene.

(4) The two binary vectors were separately introduced into the *A. tumefaciens* AGL-1 strain.

(5) Potato stem explants were co-infected with the two strains from step (4) and then co-cultivated for two days.

(6) Explants were transferred to media containing selection agents that kill *Agrobacterium*.

(7) Two weeks after transformation, the explants were again transferred to media also containing an ALS inhibitor.

(8) Herbicide resistant shoots arising from the explants within the next three months were transferred to root-inducing media and analyzed by PCR for the presence of a junction between the Ubi7 promoter and the modified ALS gene. At least 80% of regenerated plants contained such a junction.

(9) PCR-positive plants were regenerated, propagated, and evaluated for late blight resistance, reduced asparagine levels in tubers, black spot bruise tolerance, and reduced cold-induced sweetening.

The next examples describe aspects of the method.

Example 2

Imazamox Kill-Curve Essay

To determine the concentration of imazamox needed to kill untransformed potato cells, Ranger Russet internode stem explants were transformed with the binary vector pSIM1331. This vector contains (a) an expression cassette for the selectable marker gene nptII inserted between borders and (b) an expression cassette for the ipt gene in the backbone. The strain used to mediate transformation was *Agrobacterium* strain LBA4404, grown to an OD600 of 0.2. Following a 10 minute inoculation period, the explants were transferred to co-culture medium and placed in a Percival growth chamber at 24° C. under filtered light for 48 hours. Inter-node explants were transferred to hormone-free medium (HFM) containing the antibiotic timentin but lacking imazamox. Petri plates were place in Percival growth chamber at 24° C. and a 16 h photoperiod.

After two weeks, the inter-node explants were transferred to HFM containing timentin and five treatment concentrations (0, 0.5, 1.0, 1.5 & 2.0 mg/l) of the plant selection herbicide imazamox. Each treatment consisted of 3 replicates with each replicate containing ~20 inter-node explants per Petri plate. Petri plates were placed in Percival growth chamber at 24° C. and a 16 h photoperiod. Inter-node explants were subcultured every 2 weeks to fresh HFM containing the respective treatment concentration of imazamox to encourage any regeneration of shoots and reduce any *Agrobacterium* over-growth.

Results indicated that a small number of inter-node explants in all imazamox treatment concentrations exhibited some Ipt meristamatic callus growth and primary shoot formation. However, no fully developed normal shoots arose in any of the imazamox treatment concentrations. Based upon these results, it was determined that 2.0 mg/l imazamox is the optimal concentration for in vitro selection. Optimal concentration is defined as the concentration of a selective agent that allows cell growth to some degree but does not allow regeneration of fully developed shoots.

The co-culture medium included 0.444 g/l Murashige & Skoog modified basal medium with Gamborg vitamins (M404; PhytoTechnology Laboratories), 30 g/l sucrose (S24060; Research Products International Corp.) and 6.0 g/l agar (S20400; Research Products International Corp.), and had pH 5.7

The hormone-free medium (HFM) included 4.44 g/l Murashige & Skoog modified basal medium with Gamborg vitamins (M404; PhytoTechnology Laboratories), 30 g/l sucrose (S24060; Research Products International Corp.), 300 mg/l timentin and 2.0 g/l Gelzan (G024; Caisson), and had pH 5.7

Example 3

Transformation and Regeneration of Potato Plants from Stem Explants Single Strain Approach (1) 3-4-week old in vitro Ranger Russet potato plants growing on stock medium comprising 2.22 g/l Murashige & Skoog modified basal medium with Gamborg vitamins (M404; PhytoTechnology Laboratories), 15 g/l sucrose (S24060; Research Products International Corp.) and 2.0 g/l Gelzan (G024; Caisson) at pH 5.7, were used.

(2) The leaves and node sections were removed and inter-node stem portions were isolated. The inter-node stem portions were cut into 3-5 mm explants sections and placed in 15 ml of MS liquid medium containing 4.44 g/l Murashige & Skoog modified basal medium with Gamborg vitamins (M404; PhytoTechnology Laboratories), and 30 g/l sucrose (S24060; Research Products International Corp.) at pH 5.7.

(3) *Agrobacterium* (LBA4404) derived from a single colony containing a binary vector TAL effector cassette and a binary vector gene-of-interest cassette was grown overnight in Luria Broth at 28° C. in a shaking incubator. The next day the bacterial solution was pelleted and resuspended to 0.2 OD600 in MS liquid medium.

(4) Stem explants were incubated in the bacterial solution for 10 minutes at room temperature and blotted dry on sterile filter paper to remove excess of bacteria.

(5) The inoculated stem explants were placed on co-culture medium without selection in a Percival growth chamber for 48 h under filtered light. The co-culture medium contained 0.444 g/l Murashige & Skoog modified basal medium with Gamborg vitamins (M404; PhytoTechnology Laboratories), 30 g/l sucrose (S24060; Research Products International Corp.) and 6.0 g/l agar (S20400; Research Products International Corp.) at pH 5.7

(6) The stem explants were transferred to either callus induction hormone medium (CIHM) or hormone-free medium (HFM) containing antibiotics (timentin) and without plant selection. Petri plates were placed in a Percival growth chamber at 24° C. with a 16 h photoperiod. The CIHM contained 4.44 g/l Murashige & Skoog modified basal medium with Gamborg vitamins (M404; PhytoTechnology Laboratories), 30 g/l sucrose (S24060; Research Products International Corp.), 2.5 mg/l zeatin riboside, 0.1 mg/l NAA, 300 mg/l timentin and 6.0 g/l agar (S20400; Research Products International Corp.) at pH 5.7. The HFM contained 4.44 g/l Murashige & Skoog modified basal medium with Gamborg vitamins (M404; PhytoTechnology Laboratories), 30 g/l sucrose (S24060; Research Products International Corp.), 300 mg/l timentin and 2.0 g/l Gelzan (G024; Caisson) at pH 5.7

(7) After two weeks, the stem explants were transferred to either callus induction hormone medium (CIHM) or hormone-free medium (HFM) containing antibiotics (timentin) and plant selection. Petri plates were placed in a Percival growth chamber at 24° C. with a 16 h photoperiod. The CIHM contained 4.44 g/l Murashige & Skoog modified basal medium with Gamborg vitamins (M404; PhytoTechnology Laboratories), 30 g/l sucrose (S24060; Research Products International Corp.), 2.5 mg/l zeatin riboside, 0.1 mg/l NAA, 300 mg/l timentin, 2.0 mg/l imazamox and 6.0 g/l agar (S20400; Research Products International Corp.) at pH 5.7. The HFM contained 4.44 g/l Murashige & Skoog modified basal medium with Gamborg vitamins (M404; PhytoTechnology Laboratories), 30 g/l sucrose (S24060; Research Products International Corp.), 300 mg/l timentin, 2.0 mg/l imazamox and 2.0 g/l Gelzan (G024; Caisson) at pH 5.7.

(8) Four weeks post-transformation, the stem explants were transferred to either Shoot induction hormone medium (SIHM) or hormone-free medium (HFM) containing antibiotics (timentin) and plant selection. Petri plates were placed in a Percival growth chamber at 24° C. with a 16 h photoperiod. Stem explants were sub-cultured every 2-4 weeks to fresh SIHM or HFM to encourage full regeneration of shoots. The SIHM contained 4.44 g/l Murashige & Skoog modified basal medium with Gamborg vitamins (M404; PhytoTechnology Laboratories), 30 g/l sucrose (S24060; Research Products International Corp.), 2.5 mg/l zeatin riboside, 0.3 mg/l GA3, 300 mg/l timentin, 2.0 mg/l imazamox and 6.0 g/l agar (S20400; Research Products International Corp.) at pH 5.7. The HFM contained 4.44 g/l Murashige & Skoog modified basal medium with Gamborg vitamins (M404; PhytoTechnology Laboratories), 30 g/l sucrose (S24060; Research Products International Corp.), 300 mg/l timentin, 2.0 mg/l imazamox and 2.0 g/l Gelzan (G024; Caisson) at pH 5.7.

(9) Fully developed shoots were propagated for future testing and analysis.

Example 4

Transformation and Regeneration of Potato Plants from Stem Explants Double Strain Approach (1) 3-4 week-old in vitro Ranger Russet potato plants growing on stock medium containing 2.22 g/l Murashige & Skoog modified basal medium with Gamborg vitamins (M404; PhytoTechnology Laboratories), 15 g/l sucrose (S24060; Research Products International Corp.) and 2.0 g/l Gelzan (G024; Caisson) at pH 5.7 were used.

(2) The leaves and node sections were removed and inter-node stem portions were isolated. The inter-node stem portions were cut into 3-5 mm explants sections and placed in 15 ml of MS liquid medium containing 4.44 g/l Murashige & Skoog modified basal medium with Gamborg vitamins (M404; PhytoTechnology Laboratories), and 30 g/l sucrose (S24060; Research Products International Corp.) at pH 5.7.

(3) Two separate *Agrobacterium* strains (LBA4404), each derived from a single colony, one containing a binary vector comprising a TAL effector cassette and the other containing a binary vector comprising a gene-of-interest cassette, were grown overnight in Luria Broth at 28° C. in a shaking incubator. The next day, each separate bacterial solution was pelleted and re-suspended to 0.2 OD600 in MS liquid medium.

(4) Stem explants were incubated in a single combined bacterial solution that consisted of equal volumes from each individual bacterial solution (co-transformation) for 10 minutes at room temperature and blotted dry on sterile filter paper to remove excess of bacteria.

(5) The inoculated stem explants were placed on co-culture medium without selection in a Percival growth chamber for 48 h under filtered light. The co-culture medium contained 0.444 g/l Murashige & Skoog modified basal medium with Gamborg vitamins (M404; PhytoTechnology Laboratories), 30 g/l sucrose (S24060; Research Products International Corp.) and 6.0 g/l agar (S20400; Research Products International Corp.) at pH 5.7.

(6) The stem explants were transferred to either callus induction hormone medium (CIHM) or hormone-free medium (HFM) containing antibiotics (Timentin) and without plant selection. The Petri plates were placed in a Percival growth chamber at 24° C. with a 16 h photoperiod. The CIHM contained 4.44 g/l Murashige & Skoog modified basal medium with Gamborg vitamins (M404; PhytoTechnology Laboratories), 30 g/l sucrose (S24060; Research Products International Corp.), 2.5 mg/l Zeatin Riboside, 0.1 mg/l NAA, 300 mg/l Timentin and 6.0 g/l agar (S20400; Research Products International Corp.) at pH 5.7. The HFM contained 4.44 g/l Murashige & Skoog modified basal medium with Gamborg vitamins (M404; PhytoTechnology Laboratories), 30 g/l sucrose (S24060; Research Products International Corp.), 300 mg/l Timentin and 2.0 g/l Gelzan (G024; Caisson) at pH 5.7.

(7) After two weeks, the stem explants were transferred to either callus induction hormone medium (CIHM) or hormone-free medium (HFM) containing antibiotics (Timentin) and plant selection. The Petri plates were placed in a Percival growth chamber at 24° C. with a 16 h photoperiod.

The CIHM contained 4.44 g/l Murashige & Skoog modified basal medium with Gamborg vitamins (M404; PhytoTechnology Laboratories), 30 g/l sucrose (S24060; Research Products International Corp.), 2.5 mg/l Zeatin Riboside, 0.1 mg/l NAA, 300 mg/l Timentin, 2.0 mg/l imazamox and 6.0 g/l agar (S20400; Research Products International Corp.) at pH 5.7. The HFM contained 4.44 g/l Murashige & Skoog modified basal medium with Gamborg vitamins (M404; PhytoTechnology Laboratories), 30 g/l sucrose (S24060; Research Products International Corp.), 300 mg/l Timentin, 2.0 mg/l imazamox and 2.0 g/l Gelzan (G024; Caisson) at pH 5.7.

(8) Four weeks post-transformation, the stem explants were transferred to either Shoot induction hormone medium (SIHM) or hormone-free medium (HFM) containing antibiotics (Timentin) and plant selection. The Petri plates were placed in a Percival growth chamber at 24° C. with a 16 h photoperiod. Stem explants were subcultured every 2-4 weeks to fresh SIHM or HFM to encourage full regeneration of shoots. The SIHM contained 4.44 g/l Murashige & Skoog modified basal medium with Gamborg vitamins (M404; PhytoTechnology Laboratories), 30 g/l sucrose (S24060; Research Products International Corp.), 2.5 mg/l Zeatin Riboside, 0.3 mg/l GA3, 300 mg/l Timentin, 2.0 mg/l imazamox and 6.0 g/l agar (S20400; Research Products International Corp.) at pH 5.7. The HFM contained 4.44 g/l Murashige & Skoog modified basal medium with Gamborg vitamins (M404; PhytoTechnology Laboratories), 30 g/l sucrose (S24060; Research Products International Corp.), 300 mg/l Timentin, 2.0 mg/l imazamox and 2.0 g/l Gelzan (G024; Caisson) at pH 5.7

(9) Fully developed shoots were propagated for future testing and analysis.

Example 5

Target Site Sequence in Potato Ranger, Burbank and Atlantic Cultivars

To determine if the target region (5' region of the Ubi7 promoter intron) is conserved across different potato cultivars, primer pair HD175F1 and HD175R1 (SEQ ID NO: 1 and SEQ ID NO: 2) were designed and used to amplify target region from the potato varieties Ranger, Burbank and Atlantic. The amplified fragments were cloned into pGEMT-easy vector and sequenced. Sequence results showed that the target region is identical for all varieties tested. The ubi7 promoter intron sequence is represented by SEQ ID NO: 3.

Example 6

Design of TAL Effectors

A pair of TAL effectors was designed to target the selected region. Forward and reverse TALE recognition sites are listed as SEQ ID NO: 4 and SEQ ID NO: 5, respectively. The TALE scaffold was Hax3, a member of the AvrBs3 family that was identified in *Brassicaceae* pathogen *X. campestris* pv. *Armoraciae* strain 5. The modification made on this scaffold included: (a) the C-terminal activation domain of original Hax3 was truncated; (b) a nuclear localization sequence from SV40 virus was added at the N terminal of truncated Hax3 protein; (c) a codon optimization was performed on original Hax3 DNA sequence; (d) original 11.5 repeat variable diresidues (RVD) were replaced by 16.5 RVDs corresponding to the targeting sites; (e) a catalytic domain of Fok1 nuclease was added at the C-terminal of modified Hax3 scaffold.

The organization of effector proteins is shown in FIG. 5. The DNA and protein sequences of final forward and reverse TALEs are listed as SEQ ID NOS: 6, 7, 8 and 9.

Example 7

Vector for DNA Transfer

The transfer DNA consisted of potato-derived genetic elements and was delineated by T-DNA-like borders. It included three cassettes from left border to right border: (a) a late blight resistant cassette; (b) a tuber-specific silencing cassette targeting three genes: the ASN1 gene involved in asparagine formation; the acidic invertase (INV) gene associated with hydrolysis of sucrose; and the polyphenol oxidase (PPO) gene that encodes the enzyme oxidizing polyphenols upon impact bruise; and (c) a promoter-less mutated potato acetolactate synthase (ALS) gene (with W563L AND 5642I substitutions) that was hypothesized to confer resistance to ALS inhibiting herbicides when over-expressed.

The transfer DNA was designed to be inserted into the intron region positioned within the leader of one of potato's four Ubi7 genes, so that the associated Ubi7 promoter would drive expression of the ALS gene and confer resistance against ALS inhibitor-type herbicides.

Since the Ubi7 monomer plays an important role in protein stabilization, the coding sequence, preceded by part of the intron, was fused in frame to the ALS gene. Insertion of the transfer DNA into a binary vector created the plasmid pSIM2168. The organization of the transfer DNA is illustrated in FIG. 1. The DNA and protein sequences of wild type and mutated ALS gene are represented by SEQ ID NOS: 10, 11, 12 and 13. The whole transfer DNA sequence in pSIM2168 is represented by SEQ ID NO: 14.

Example 8

Vector for TAL Effectors

Each TAL effector, forward or reverse, was driven by a constitutive (35s or FMV) promoter and followed by a terminator (Nos or Ocs), to form two separate plant expression cassettes. The two cassettes were cloned into a binary vector to form the pSIM2170 as shown in FIG. 2. This binary vector had only one border and contained an ipt gene expression cassette so that it was possible to select against stable integration of the effector genes.

Example 9

The Right Border Upstream the Ubi7 Intron 5' Region Supports DNA Transfer

Figure 3:
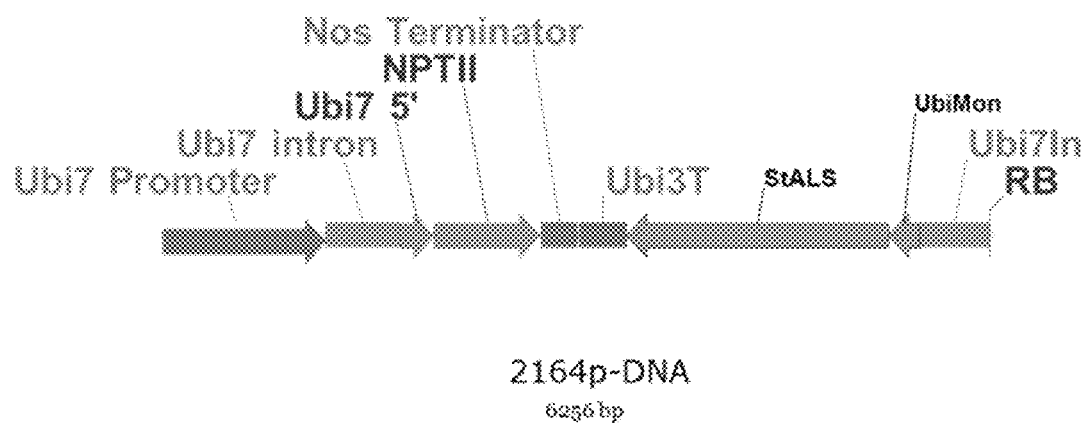
FIG. 3 shows the right border testing cassette described in Example 9.

Because efficacy of the border as primary cleavage site is dependent, in part, on flanking DNA sequences, a right border upstream the Ubi7 intron 5' region was tested for its ability to support DNA transfer. For this purpose, a DNA fragment comprising the right border/intron sequence upstream from the Ubi7 monomer and modified ALS gene was cloned into the binary vector pSIM123-F to form pSIM2164. Vector pSIM123-F contained an expression cassette for the selectable marker gene nptII, but lacked the borders needed to transfer this cassette into plant cells (see FIG. 3). Nevertheless, infection of explants with an *Agro-* bacterium strain carrying the pSIM2164 generated the same number of kanamycin resistant shoots per explant as a positive control (infection with a strain carrying the nptII gene positioned within T-DNA borders).

Figure 4:
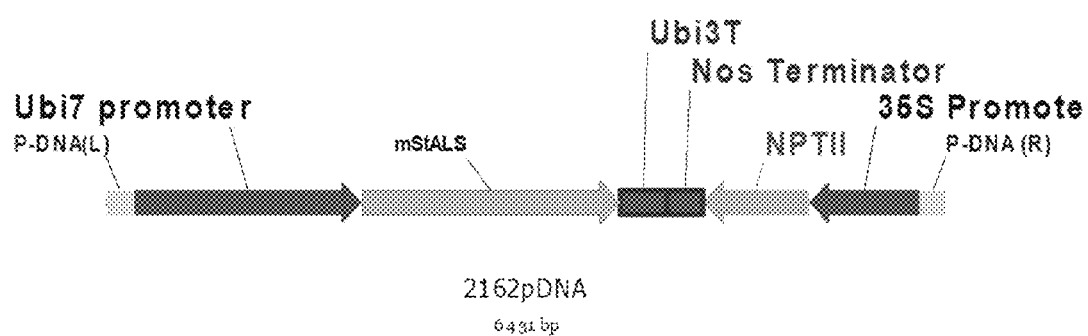
FIG. 4 illustrates the DNA organization of the plasmid pSIM2162 carrying the Ubi7::ALS cassette.

To test the efficiency of the mutated ALS gene in conferring imazamox resistance to potato, a vector carrying a Ubi7:: ALS cassette (pSIM2162, see FIG. 4) was created. Transformation with this vector yielded herbicide resistant plants that were confirmed by PCR to contain the Ubi7::ALS cassette.

Example 10

Vector Design for Transient Transformation in N. Benthamiana

Figure 6:
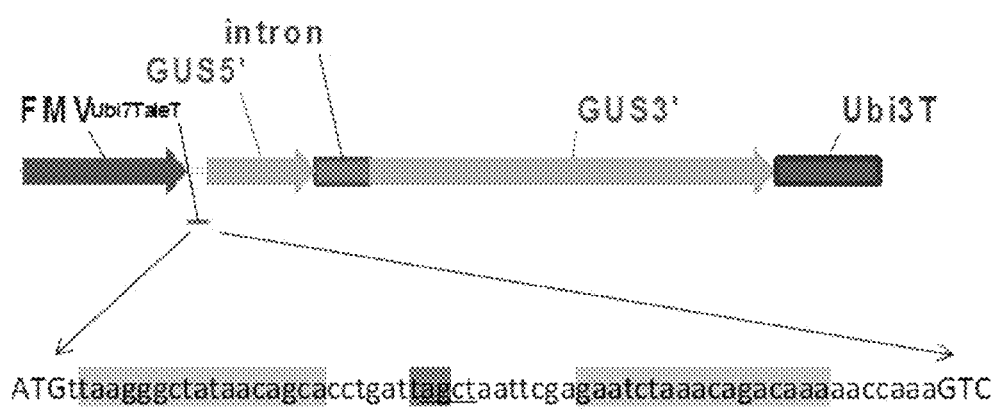
FIG. 6 illustrates the organization of the plasmid pSIM216 carrying the target sequence containing the forward and reverse recognition sites positioned immediately downstream from the start codon of the GUS reporter gene.

To test the efficiency of the specifically designed TALEs in vivo, a vector with the target sequence (part of the Ubi7 intron) was designed. This vector, pSIM2167, was co-transformed with the vector carrying the effectors into N. benthamiana. As shown in FIG. 6, the target sequence contained the forward and reverse recognition sites positioned immediately downstream from the start codon of the GUS reporter gene. A stop codon between the two recognition sequences and in frame with the GUS coding sequence rendered the GUS coding sequence inactive. If the TALEs bind their designed recognition sites and cleave in the intermediary sequence, subsequent repair would be expected to occasionally eliminate the stop codon without altering the reading frame, thus restoring GUS function. Such events could be visualized by histochemically staining the N. benthamiana leaves, about 4 days after infiltration.

The target sequence region can also be PCR amplified and sequenced to identify TALE mediated mutations. However, direct PCR and cloning of the target sequence would yield an un-modified target sequence because of the possible low efficiency of transformation. Therefore, the isolated DNA was first digested with the AluI enzyme, which cleaves the AGCT restriction site located between the two TALE recognition sites. After amplification, the PCR products were again digested with AluI to further enrich the mutated target sequence for downstream cloning and sequencing analyses. The entire sequence of FMV-target-GUS-Nos cassette is represented by SEQ ID N: 15. The PCR primers used for amplifying the target sequence are represented by SEQ ID NO: 16 and SEQ ID NO: 17.

Example 11

Agrobacterium Transformation and N. benthamiana Infiltration

Figure 7:
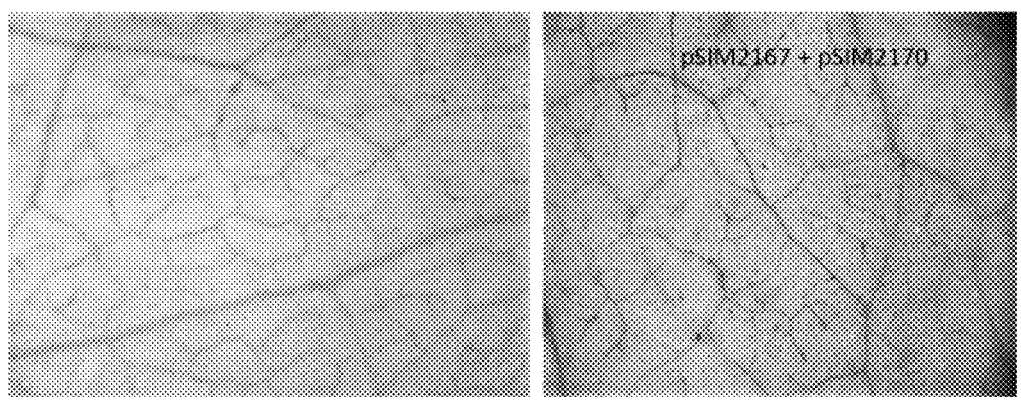
FIG. 7 shows GUS staining of Nicothiana benthamiana leaves following Agrobacterium infiltration. Left panel: infiltration with target vector pSIM2167 alone. Right panel; infiltration with target vector pSIM2167 and TAL effector vector pSIM2170.
Figure 10:
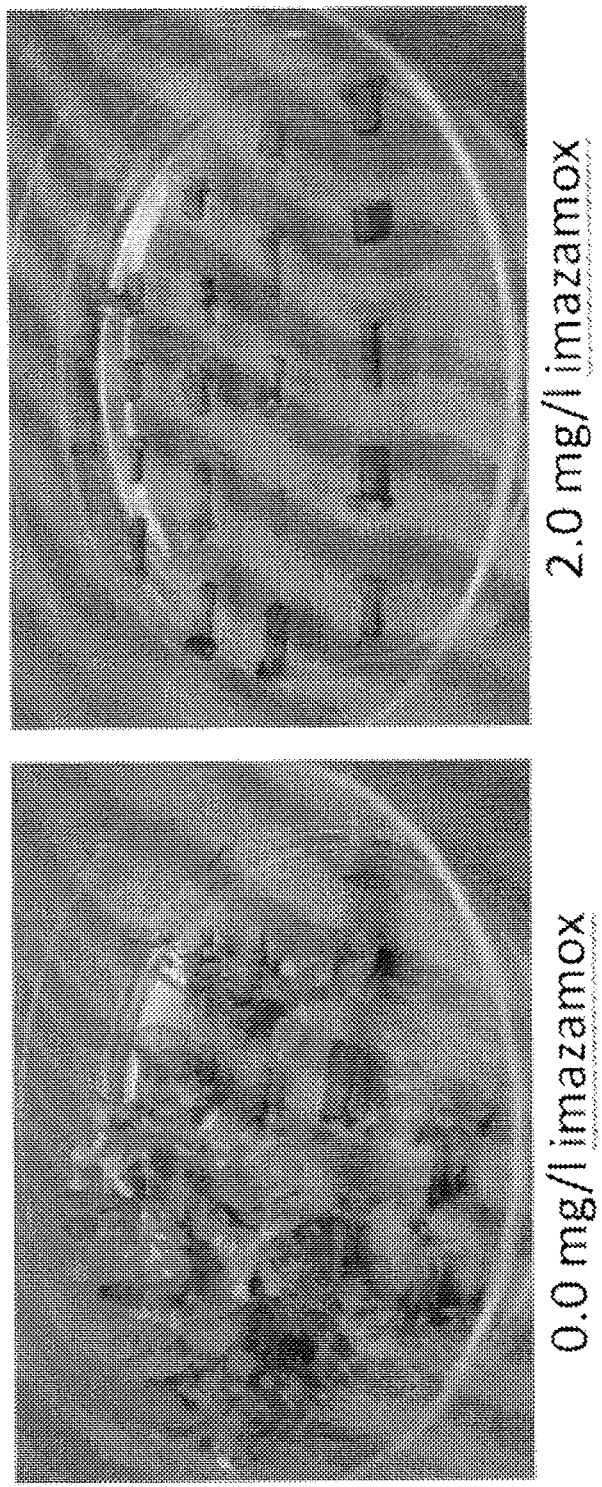
FIG. 10 shows inter-node explants grown in hormone-free medium containing timentin and 0.0 mg/l imazamox (left panel) or 2.0 mg/l imazamox (right panel). No fully developed normal shoots were visible when the inter-node explants were grown in a medium containing imazamox.

The designed vectors were transformed into *Agrobacterium* strain AGL1 and tested for vector stability. Four to six days after infiltration, leaf discs from infiltrated tissue were collected for GUS staining assay and DNA isolation. Isolated DNA was digested with the AluI enzyme and used as template for target region amplification and further cloning and sequencing. As shown in FIG. 7, GUS staining was observed in co-infiltrated tissue (right panel) but not in the tissue infiltrated by target vector alone (left panel). Further sequence analyses showed in FIG. 8 also confirmed that the target sequence was modified by TALEs.

Example 12

Genotyping of Stable Transformants

Primer pairs HD208 F1 and R1 were designed to genotype herbicide resistant transformants. The forward primer is located in the promoter region of Ubi7 gene, and the reverse primer is located in ALS coding region. The primer pair is targeted-insertion specific primer because only if the transfer DNA is inserted into the designed position, the primer pair will amplify a fragment. PCR analysis of the independent herbicide resistant lines from the co-transformation of pSIM2170 and pSIM2168 did amplify fragments. These fragments were cloned and sequenced. As shown in FIG. 9, in one line, TALE1, the fragment contained part of the transfer DNA cassette, including the partial Ubi7 intron, the Ubi7 monomer and part of the ALS coding region, flanked by potato genome sequence. Sequence blast showed that the flanked potato genome is the promoter region of an Ubi7 like gene located on chromosome 7 which also contains very similar recognition sites of the designed TALE. In another two lines, TALE2 and TALE3, the transfer DNA cassettes were inserted into the same genomic loci as in TALE1, except that intron portions of the transfer DNA cassette were largely deleted. The TALE2 and TALE3 lines were very similar, except that in TALE2 there was a 9 bp deletion in the Ubi7 monomer.

Example 13

Characterization of Stable Transformed Lines for Targeted Insertion

Figure 12:
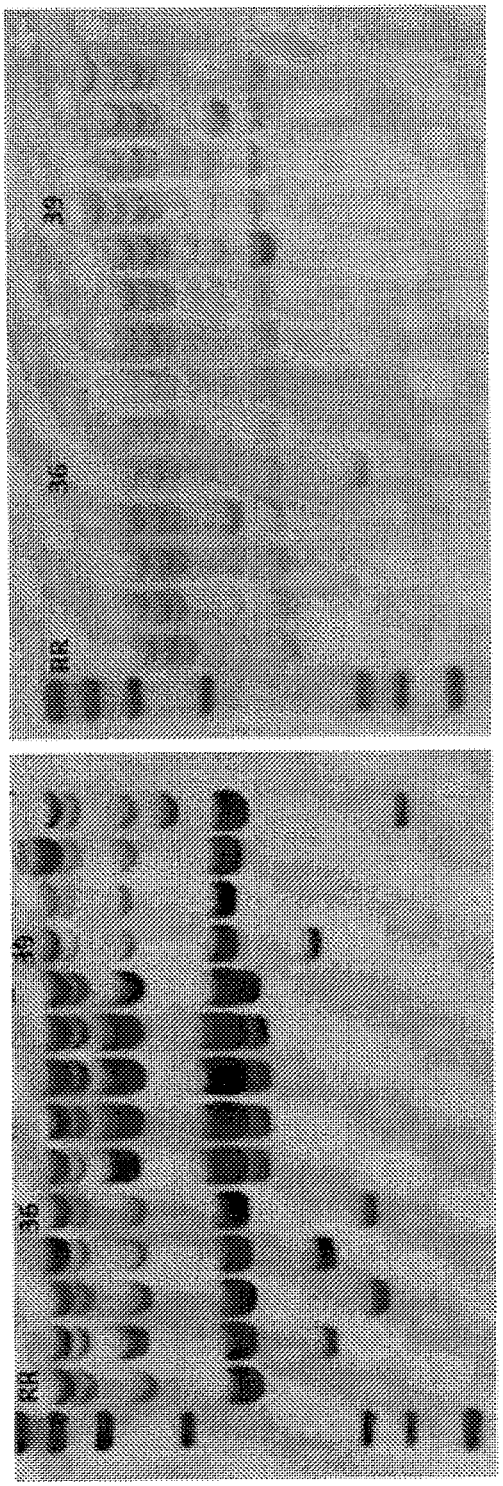
FIG. 12 depicts the southern blot gels for selected herbicide-resistant Ranger Russet lines co-transformed with the pSIM2170 and pSIM2168 plasmids for targeted insertion. Left panel: invertase probe; right panel: Vnt1 promoter probe. Each additional band in the transformed lines, as compared to the Ranger Russet control (RR) lines, indicates a single copy transgene for lines RR-36 (36) and RR-39 (39). Transformed lines RR-26 and RR-32 are not shown.

The data and results described above indicated that the targeted insertion of an intended DNA segment was successful. Herbicide resistant Ranger Russet (RR) lines from the co-transformation of pSIM2170 and pSIM2168 were propagated and transferred to soil for following tests/analyses. Specifically, the transformed lines were tested for resistance to Late blight diseases challenge, by determining the activity of the enzyme polyphenol oxidase, and running southern analyses for copy number of both silencing and Vnt1 cassettes. For diseases assay, plantlets in soil for three weeks were inoculated with *P. infestans* late blight strain US8 BF6 for the development of disease symptom. For Southern blot analyses, 3μg DNA isolated from leaf tissues were digested by HindIII restriction enzyme, run on 0.7% agarose gel, transferred to positive charged nylon membrane and hybridized with Dig labeled probes either for invertase fragment in silencing cassette or for Vnt1 promoter in Vnt1 expression cassette. Four lines were identified and summarized in Table 1 below. These lines were late blight resistant (see FIG. 11) and had a single copy for both cassettes (see FIG. 12). Each extra band in lines RR-36 and RR-39, as compared to RR control lines, indicated the presence of a single copy of the transgene. (Data for line RR-26 and RR-32 are not shown).

TABLE 1

Line Characterization for Targeted Insertion.

| Line Number | Late Blight | Invertase Copy No. | Vnt1 Copy No. |
|---|---|---|---|
| Ranger control | susceptible | 0 | 0 |
| RR-26 | resistant | 1 | 1 |
| RR-32 | resistant | 1 | 1 |
| RR-36 | resistant | 1 | 1 |
| RR-38 | resistant | 1 | 1 |

Example 14

Field Trial Evaluation of Transformed Lines for Targeted Insertion

Figure 13:
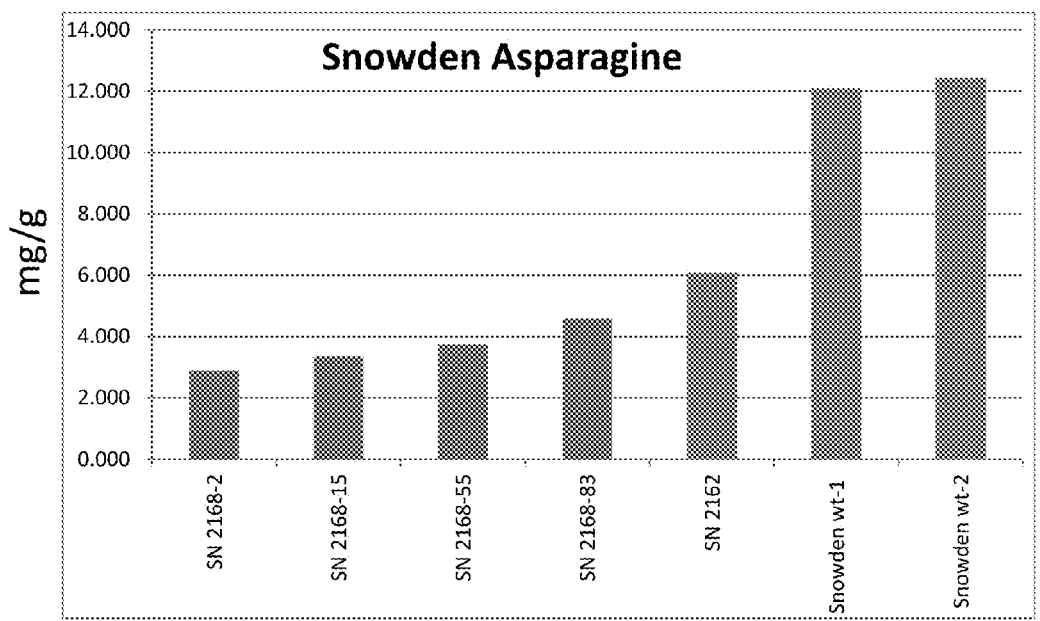
FIG. 13 shows uniform silencing of asparagine in potato tubers. Snowden lines 2, 15, 55 and 83 were transformed with pSIM2168 and pSIM2170.
Figure 14:
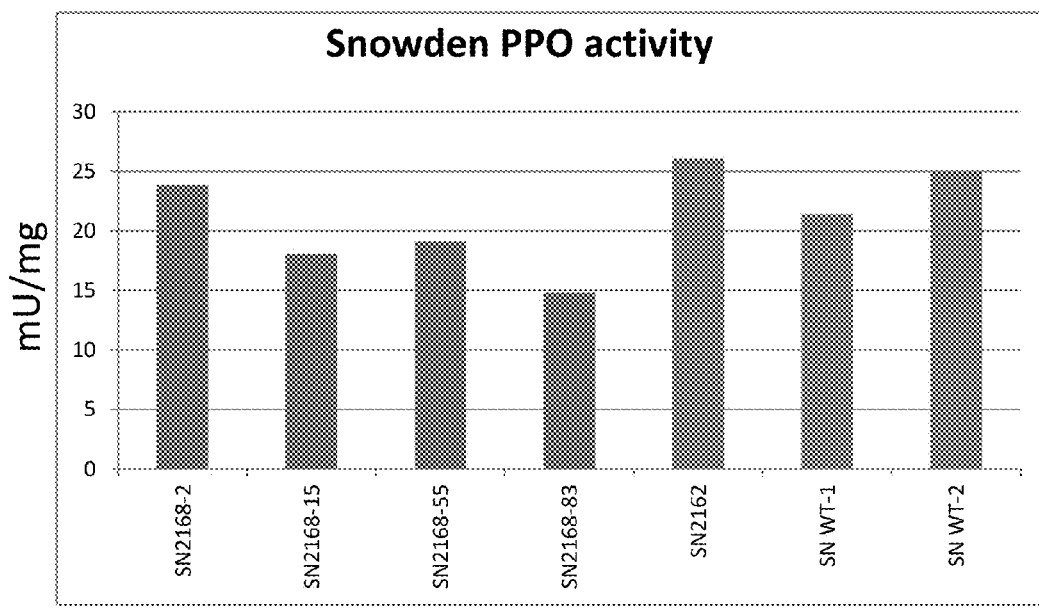
FIG. 14 shows uniform silencing of polyphenol oxidase in potato tubers. Snowden lines 2, 15, 55 and 83 were transformed with pSIM2168 and pSIM2170.
Figure 15:
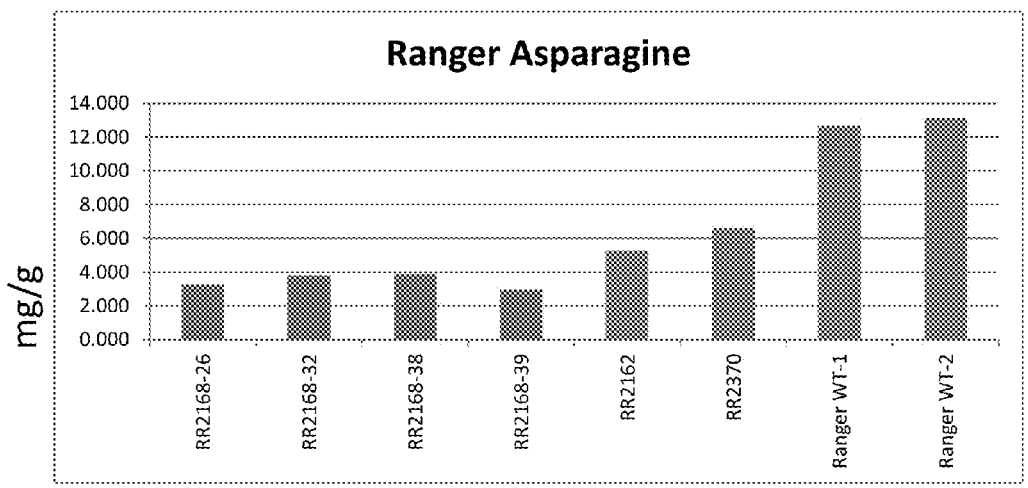
FIG. 15 shows uniform silencing of asparagine in potato tubers. Ranger lines 26, 32, 38 and 39 were transformed with pSIM2168 and pSIM2170.
Figure 16:
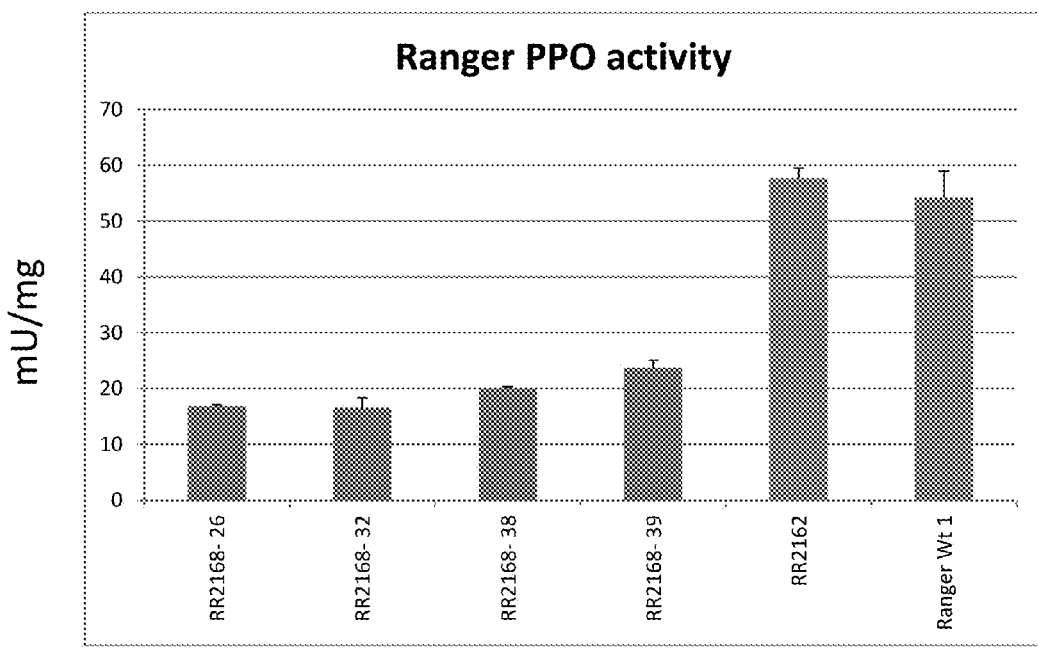
FIG. 16 shows uniform silencing of polyphenol oxidase in potato tubers. Ranger lines 26, 32, 38 and 39 were transformed with pSIM2168 and pSIM2170.

Plantlets of Ranger Russet (RR) and Snowden (SN) that were co-transformed with pSIM2170 and pSIM2168 were planted in a replicated field trial. Plant lines were evaluated for trait efficacy and yield. Snowden lines 2, 15, 55 & 83 (see FIG. 13) as well as Ranger lines 26, 32, 38 & 39 (see FIG. 15) were very uniform for the silencing of asparagine in potato tubers. In addition, the same SN lines (see FIG. 14) and RR lines (see FIG. 16) also had very uniform silencing of polyphenol oxidase (PPO). These results indicate that the target site allows for uniform and high expression of the silencing cassette. Yield from the above mention SN and RR lines (see FIG. 17) were not significantly different when compared to the wild type (WT) and empty vector controls (2162, 2370). This result suggest that the targeted insertion site does not have a negative impact on yield potential.

Example 15

CAS9-Mediated Targeted Transfer DNA Insertion

Besides Transcription activator-like effector nucleases (TALEN), there are other endonuclease based genome editing enzymes such as meganuclease (Epinat et al., 2003), Zinc finger nuclease (ZFN) (Porteus and Baltimore, 2003), (Bogdanove and Voytas, 2011) and CRISPR-associated (Cas) endonuclease (Jinek et al., 2012; Mussolino, C. & Cathomen 2013) that could introduce DSB in the target DNA sequence. Once DSB was generated, plant DNA repair machinery will either repair the break through a non-homologous end joining (NHEJ) pathway, which is imprecise and creates mutations to achieve gene knock out, or through a homologous recombination (HR) pathway to achieve gene targeting (gene replacement or insertion) (Symington and Gautier 2011). Therefore, the similar strategy used in our TALEN based DNA integration is transferrable into other nuclease based genome editing tools. As an example, here we show an engineered CAS9 endonuclease can modify on our Ubi7 intron DNA target.

Figure 18:
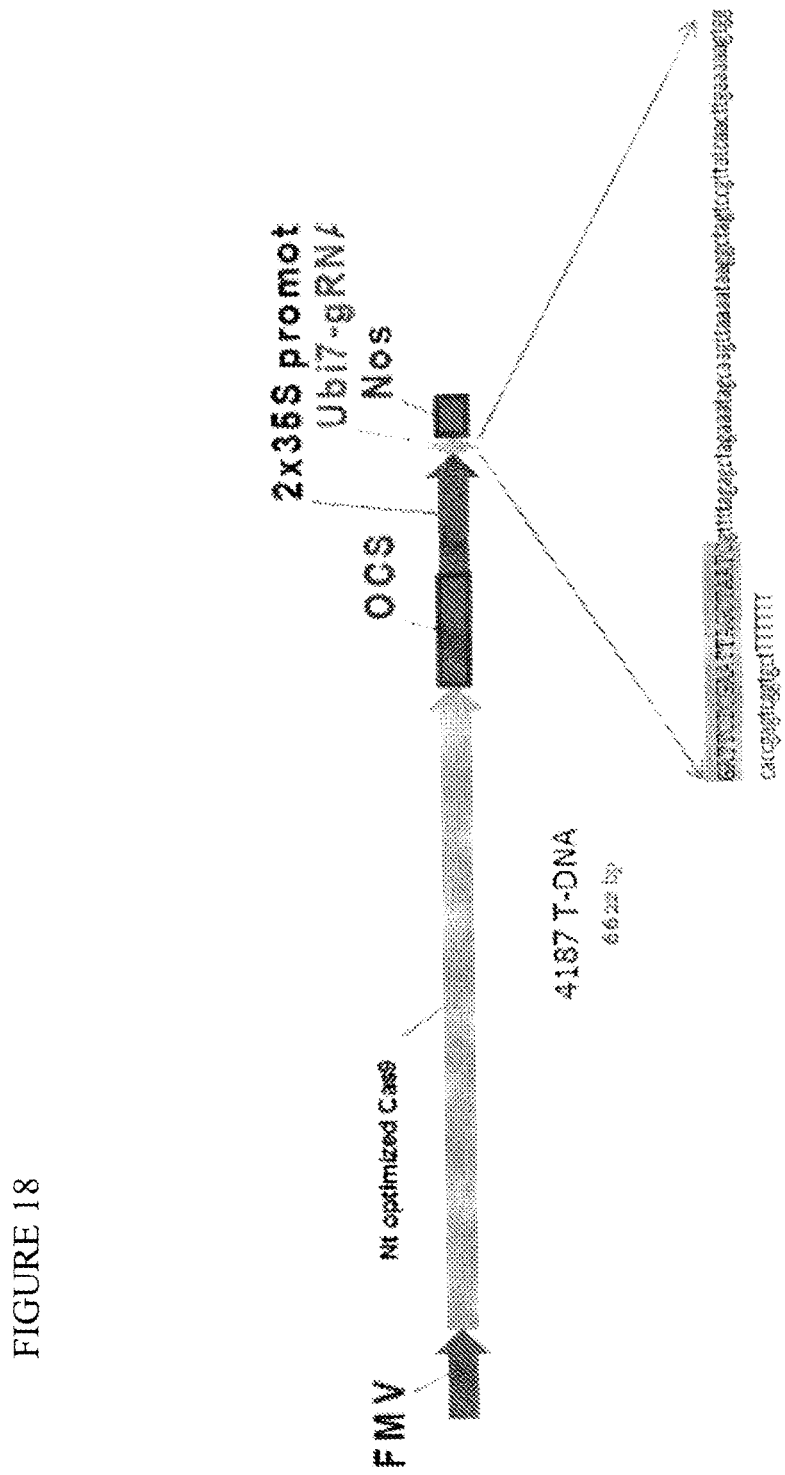
FIG. 18 shows FMV-CAS9-OCS and 35S-gRNA-Nos cassettes in pSIM4187. The sequence of gRNA is shown and the 20 bp target specific sequence is highlighted.
Figure 19:
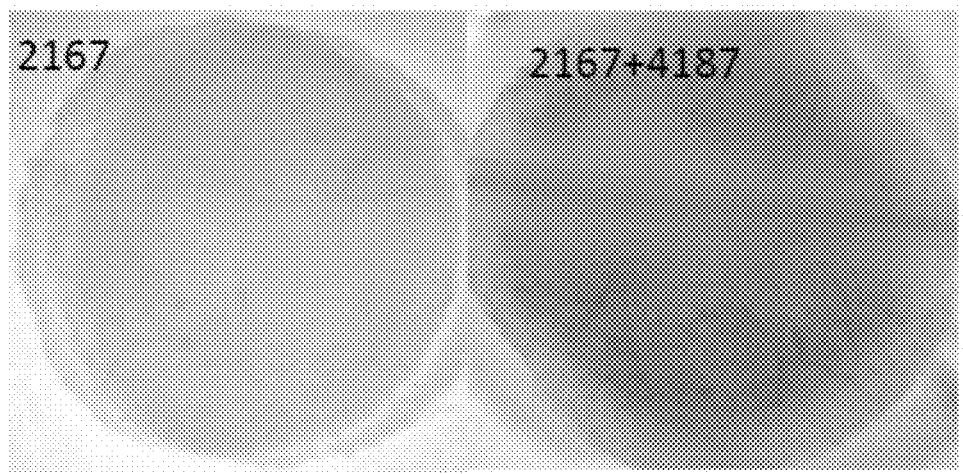
FIG. 19 shows GUS staining of *N. benthamiana* leaf after *Agrobacterium* infiltration. pSIM2167: Target-GUS vector; pSIM4187: Cas9 and gRNA vector.

Cas9 genome editing technology uses a small chimeric RNA which contains a 20 bp target specific sequence and a small RNA scaffold to guide Cas9 nucleases to cleave the target. Construct pSIM4187 was designed to contain two expression cassettes (FIG. 18). The first is a CAS9 nuclease expression cassette. Plant codon-optimized Cas9 was driven by a constitutive FMV promoter and a nuclear localization sequence from SV40 virus was added at the N terminal of protein. The DNA and amino acid sequences of engineered Cas9 are listed as SEQ ID No:18 and SEQ ID No:19, respectively. The second cassette produces guide RNA upon transcription in the plant cell under the control of a constitutive 35S promoter. The sequence of guide RNA is listed as SEQ ID NO:20. The designed vectors pSIM4187 was transformed into *Agrobacterium* strain AGL1 and checked for vector stability. Then *agrobacteria* containing pSIM4187 were used to co-infiltrate *N. Benthamina* with *agrobacteria* containing plasmid pSIM2167, which is the construct containing the Ubi7 intron target described in previous examples. Two to four days after infiltration, leaf discs from the infiltrated tissues were collected for GUS staining assay and DNA isolation. Isolated DNA was digested with AluI enzyme and used as template for target region amplification and further cloning and sequencing. As shown in FIG. 19, GUS staining was observed in co-infiltrated tissue (right panel) but not in the tissue infiltrated by target vector alone (left panel). Further sequence analyses showed in FIG. 20 confirmed the target sequence was modified by Cas9. The modification is very similar to that induced by designed TALEN.

The invention claimed is:

1. A transformed potato plant comprising in its genome a sequence exogenous to the untransformed plant, said sequence comprising:
   (i) a promoter-free marker cassette; and
   (ii) a desired polynucleotide;
wherein the promoter-free marker cassette and the desired polynucleotide are positioned downstream of one of the plant's genomic endogenous Ubi7 gene promoters, and wherein the promoter-free marker cassette is expressed by said genomic endogenous Ubi7 gene promoter.

2. The transformed potato plant of claim 1, wherein the desired polynucleotide comprises a silencing cassette targeting one or more genes selected from the group consisting of asparagine synthase 1 (Asn1), polyphenol oxidase (Ppo), and vacuolar invertase (Inv) genes.

3. The transformed potato plant of claim 2, wherein the desired polynucleotide further expresses a late blight resistance gene Vnt1.

4. The transformed potato plant of claim 3, wherein said transformed potato plant is capable of producing tubers wherein the plant has a phenotype characterized by one or more of black spot bruise tolerance, reduced cold-induced sweetening and reduced asparagine levels in its tubers as a result of the expression of the desired polynucleotide.

5. A heat-processed product, wherein said heat processed product comprises cells from the transformed potato plant of claim 4.

6. The heat-processed product of claim 5, wherein the product is a French fry, chip, crisp, potato, dehydrated potato or baked potato.

7. The heat-processed product of claim 5, wherein the heat-processed product has a lower level of acrylamide than a heat-processed product of an otherwise identical plant lacking the desired polynucleotide.

8. The transformed potato plant of claim 1, wherein the promoter-free marker cassette encodes a mutated acetolactate synthase (ALS) gene, and wherein said mutated ALS gene confers the plant with resistance to at least one ALS inhibitor selected from the group consisting of sulfonylureas, imidazolinones, triazolopyrimidines, pyrimidinyl oxybenzoates, and sulfonylamino carbonyl triazolinones.

9. The transformed potato plant of claim 8, wherein the mutated ALS gene encodes for a peptide selected from the group consisting of SEQ ID Nos: 11 and 13.

10. A heat-processed product, wherein said heat processed product comprises cells from the tuber grown from the transformed potato plant of claim 4.

11. A method for stably integrating a desired polynucleotide downstream of a potato plant's endogenous Ubi7 gene promoter, said method comprising:
   (A) transforming potato plant material with a first vector comprising nucleotide sequences encoding Transcription Activator-Like Effector Nuclease (TAL) proteins designed to recognize a target sequence, wherein the target sequence is located within an intron of the potato plant's endogenous Ubi7 gene 5'-untranslated region;
   (B) transforming the potato plant material with a second vector comprising (i) a marker gene that is not operably linked to a promoter, referred to as a promoter-free marker cassette, and which comprises a sequence homologous to the target sequence, and (ii) a desired polynucleotide; and
   (C) identifying transformed potato plant material in which the desired polynucleotide is stably integrated downstream of the potato plant's endogenous Ubi7 gene promoter.

12. The method of claim 11, wherein the transformed plant material is exposed to conditions that reflect the presence or absence of the marker gene in the transformed plant.

13. The method of claim 12, wherein the marker gene is an herbicide resistance gene and the transformed plant material is exposed to herbicide.

14. The method of claims 13, wherein the herbicide resistance gene is a mutated ALS gene, and wherein said mutated ALS gene confers the potato plant with resistance to at least one ALS inhibitor selected from the group consisting of sulfonylureas, imidazolinones, triazolopyrimidines, pyrimidinyl oxybenzoates, and sulfonylamino carbonyl triazolinones.

15. The method of claim 11, wherein the promoter-free marker cassette is stably integrated into the potato plant's genome.

16. A method for the targeted insertion of exogenous DNA downstream of a potato plant's endogenous Ubi7 gene promoter, said method comprising the steps of
   (i) transforming isolated potato plant cells with
      (A) a first binary vector comprising a promoter-less cassette comprising (a) a right border sequence linked to (b) a partial sequence of the endogenous Ubi7 gene's intron 5'-untranslated region; (c) a Ubi7 monomer-encoding sequence fused to a mutated ALS gene; (d) a desired nucleotide sequence, wherein the desired nucleotide sequence is not operably linked to a promoter; and (e) a terminator sequence; and
      (B) a second binary vector comprising (a) a right border; (b) a forward expression cassette and a reverse expression cassette, wherein each expression cassette comprises a nucleotide sequence encoding a modified TAL operably linked to a strong constitutive promoter, and a terminator sequence; and (c) a sequence encoding isopentenyl transferase (ipt), wherein the modified TAL is designed to bind the endogenous Ubi7 gene's intron 5' untranslated region; and (ii) culturing the transformed potato plant cells under conditions that promote growth of edited potato plants that express the desired nucleotide sequence; wherein no vector backbone DNA is permanently inserted into the edited potato plant's genome.

17. The method of claim 16, wherein the modified TAL comprises (a) a truncated C-terminal activation domain comprising a FokI endonuclease catalytic domain; (b) a codon-optimized target sequence binding domain comprising 16.5 repeat variable diresidues corresponding to the endogenous Ubi7 5'-untranslated intron sequence; and (c) an N-terminal region comprising a SV40 nuclear localization sequence.

18. The method of claim 16, wherein the desired nucleotide sequence is a silencing cassette targeting one or more genes selected from the group consisting of Asn1, Ppo, and Inv genes.

19. The method of claim 16, wherein the first binary vector further comprises a late blight resistance gene Vnt1 operably linked to its native promoter and terminator sequences.

* * * * *

SEQUENCE LISTING

<160> NUMBER OF SEQ ID NOS: 51

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcctaatttt ccccaccaca                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aacagccgga gaaactcaaa                                              20

<210> SEQ ID NO 3
<211> LENGTH: 568
<212> TYPE: DNA
<213> ORGANISM: Solanum tuberosum

<400> SEQUENCE: 3
gttagaaatc ttctctattt ttggttttg tctgtttaga ttctcgaatt agctaatcag        60
gtgctgttat agcccttaat tttgagtttt ttttcggttg tcttgatgga aaaggcctaa     120

```
aatttgagtt tttttacgtt ggtttgatgg aaaaggccta caattggagt tttccccgtt    180
gttttgatga aaaagcccct agtttgagat ttttttttctg tcgattcgat tctaaaggtt   240
taaaattaga gttttttacat ttgtttgatg aaaaaggcct taaatttgag ttttttccggt  300 tgatttgatg aaaaagccct agaatttgtg ttttttcgtc ggtttgattc tgaaggccta   360
aaatttgagt ttctccggct gttttgatga aaaagcccta aatttgagtt tctccggctg   420
ttttgatgaa aaagccctaa atttgagttt ttccccgtg ttttagattg tttggttta    480 attctcgaat cagctaatca gggagtgtga aaagccctaa atttgagttt ttttcgttgt   540
tctgattgtt gttttttatga atttgcag                                     568
```

```
<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttttgtctgt ttagattc                                                  18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttaagggcta taacagca                                                  18

<210> SEQ ID NO 6
<211> LENGTH: 3396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atggctccca aaagaagag aaaggtagaa ccaggatcac ctggtggaca atcacttatg     60
gacccaatac gaagcagaac gccatcacca gctagggaac ttctctctgg accacagcct   120
gatggagttc agccaactgc agatcgaggt gtttctccgc cagccggtgg cccttagat    180 ggactcccag caagaagaac aatgtccgt accagactcc caagtccccc tgccccgtcg   240
ccagcctttt cagctgactc cttctctgat cttcttaggc aatttgaccc ttctctttc    300 aatacatccc ttttcgattc acttcctcct tcggcgcac atcatactga ggcagccacc    360
ggcgaatggg acgaagtcca agtggttta agggcagctg atgctccacc accgacgatg    420
agagtcgctg ttaccgccgc acgtcctcct agagccaagc cagcccctag aagacgagct   480
gcgcaaccct ccgatgcaag ccctgcagct caagtagacc ttcgaacact aggttactcc   540
cagcaacaac aagaaaaaat aaagccaaag gttagatcaa cagttgcaca acatcacgaa   600
gccctagtcg acacggatt tacacatgct catatcgtgg ctcttcaca acatcctgca     660 gctcttggaa cagtcgctgt caaatatcag gatatgattg ctgcattgcc agaagctact   720
cacgaagcta tcgtcggagt tgggaaacaa tggtcaggcg caagagcatt agaggcgctt   780
```

```
ctcaccgtag ctggtgaatt acgaggtcct ccactccaat tggatactgg gcaattatta        840
aaaatcgcta aacgaggtgg agtcactgct gtcgaagccg ttcatgcatg gcgtaacgct        900 ctcacgggggg ccccactaaa ccttacccca caacaagttg tggcaatagc ttctaatggt       960
ggtggtaaac aagcccttga gacggttcaa agacttctac cagttctttg tcaggcacat       1020
ggattgaccc cacaacaggt cgtagcaatc gcatctaacg gaggtggtaa gcaagctctt       1080
gaaacggtac aaagattact tcccgtgctt tgtcaagctc atggactcac tcctcaacaa       1140
gtggtcgcta ttgcaagtaa cggtggtgga aagcaagcac tagaaaccgt ccaacgactc       1200
cttcctgttc tctgtcaagc acatggtttg actcctcagc aggtcgtcgc aattgcatca       1260
aacaatggag gcaaacaagc tttagaaaca gtacaaagac tattgcccgt tctttgccaa       1320
gcgcatgggt taactcccga caagtcgtt gccattgcaa gtaacggagg aggtaaacaa        1380
gctctcgaaa cggttcaagc acttttaccc gttctctgtc aagcacatgg actcacacct       1440
gaacaagtag ttgctatcgc atcgcatgat ggtggaaaac aagcactgga aactgtacaa       1500
agacttttgc cagtttatg tcaagcgcac ggtcttactc ctcaacaagt tgtcgccatt        1560
gcctctaatg gaggtggaaa caagctcttg aaactgtcc agagacttct gcccgttcta       1620
tgtcaggctc atgggctaac ccctcaacag gttgttgcaa tcgcatctaa taatggagga       1680
aaacaagctt tagaaactgt ccaacgacta ctgcccgttc tctgccaagc acacggactt       1740
acaccacaac aggttgtagc tatagctagc aatggtggcg gtaaacaggc tttggaaaca       1800
gtacagcggc ttctaccagt cttatgccaa gcccacgggc ttactcctca acaagttgtc       1860
gccattgcct ctaatggagg tggaaaacaa gctcttgaaa ctgtccagag acttctgccc       1920
gttctatgtc aggctcatgg gcttactcct gaacaggttg tcgcaatagc ttcaaacggt       1980
ggcggaaaac aagctcttga aacagtgcaa cgtctccttc ccgtcctctg tcaggctcac       2040
ggacttacgc ccgaacaagt tgttgctata gcttcgaata ttggtggaaa acaagctctc       2100
gaaaccgtcc aaaggctcct cccagtactt tgccaagcac atggattaac ccctgagcaa       2160
gtagttgcaa ttgcctcgaa caatggagga aagcaagcat tagaaactgt tcagagactt       2220
ttgcctgtcc tgtgtcaagc ccacggtctt acaccagagc aggttgtcgc tatagcttct       2280
aacattggtg gaaagcaagc tcttgagact gtgcaacgtt tgcttccagt cctctgtcaa       2340
gcacacggac tcactccaca acaggtggtt gcaattgctt caaatggcgg tgcaaacaa       2400 gcattagaga ctgtacagag actacttcct gttctttgtc aagcacaagg gctcacccct       2460
gagcaggtag tcgctatcgc ctcaaatggt ggcgggaagc aggccctgga gactgttcag       2520
agactactgc ccgtcctatg tcaggctcac ggtctaacac cacaacaagt cgtcgcaatc       2580
gctagtcatg acggaggtcg acctgctcta gagtcgatag tcgcacaact atcacggacct      2640 gatcccgctc ttgcagcatt gacaaacgat catttagtcg cacttgcatg tttaggagga       2700
cgaccagcac ttgatgccgt taagaaagga ctaccgcacg cccctgcatt gattaaaaga       2760
acaaacagac gaatcccgga gagaacttca catcgtgtag ccaagcaact tgtcaaaagt       2820
gaactggagg agaagaaatc tgaacttcgt cataaattga aatatgtgcc tcatgaatat       2880
attgaattaa ttgaaattgc cagaaattcc actcaggata gaattcttga aatgaaggta       2940
atggaatttt ttatgaaagt ttatggatat agaggtaaac atttgggtgg atcaaggaaa       3000
ccggacggag caatttatac tgtcggatct cctattgatt acggtgtgat cgtggatact       3060
aaagcttata gcggaggtta taatctgcca attggccaag cagatgaaat gcaacgtatt       3120
gtcgaagaaa atcaaacacg aaacaaacat atcaacccta atgaatggtg gaaagtctat       3180
```

-continued

```
ccatcttctg taacggaatt taagttttta tttgtgagtg gtcactttaa aggaaactac    3240
aaagctcagc ttacacgatt aaatcatatc actaattgta atggagctgt tcttagtgta    3300
gaagagcttt taattggtgg agaaatgatt aaagccggca cattaacctt agaggaagtg    3360
agacggaaat ttaataacgg cgagataaac ttttga                              3396
```

<210> SEQ ID NO 7
<211> LENGTH: 1131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Ala Pro Lys Lys Arg Lys Val Glu Pro Gly Ser Pro Gly Gly
1               5                   10                  15

Gln Ser Leu Met Asp Pro Ile Arg Ser Arg Thr Pro Ser Pro Ala Arg
            20                  25                  30

Glu Leu Leu Ser Gly Pro Gln Pro Asp Gly Val Gln Pro Thr Ala Asp
        35                  40                  45

Arg Gly Val Ser Pro Pro Ala Gly Gly Pro Leu Asp Gly Leu Pro Ala
    50                  55                  60

Arg Arg Thr Met Ser Arg Thr Arg Leu Pro Ser Pro Pro Ala Pro Ser
65                  70                  75                  80

Pro Ala Phe Ser Ala Asp Ser Phe Ser Asp Leu Leu Arg Gln Phe Asp
                85                  90                  95

Pro Ser Leu Phe Asn Thr Ser Leu Phe Asp Ser Leu Pro Pro Phe Gly
            100                 105                 110

Ala His His Thr Glu Ala Ala Thr Gly Glu Trp Asp Glu Val Gln Ser
        115                 120                 125

Gly Leu Arg Ala Ala Asp Ala Pro Pro Thr Met Arg Val Ala Val
    130                 135                 140

Thr Ala Ala Arg Pro Pro Arg Ala Lys Pro Ala Pro Arg Arg Arg Ala
145                 150                 155                 160

Ala Gln Pro Ser Asp Ala Ser Pro Ala Ala Gln Val Asp Leu Arg Thr
                165                 170                 175

Leu Gly Tyr Ser Gln Gln Gln Gln Glu Lys Ile Lys Pro Lys Val Arg
            180                 185                 190

Ser Thr Val Ala Gln His His Glu Ala Leu Val Gly His Gly Phe Thr
        195                 200                 205

His Ala His Ile Val Ala Leu Ser Gln His Pro Ala Ala Leu Gly Thr
    210                 215                 220

Val Ala Val Lys Tyr Gln Asp Met Ile Ala Ala Leu Pro Glu Ala Thr
225                 230                 235                 240

His Glu Ala Ile Val Gly Val Gly Lys Gln Trp Ser Gly Ala Arg Ala
                245                 250                 255

Leu Glu Ala Leu Leu Thr Val Ala Gly Glu Leu Arg Gly Pro Pro Leu
            260                 265                 270

Gln Leu Asp Thr Gly Gln Leu Leu Lys Ile Ala Lys Arg Gly Gly Val
        275                 280                 285

Thr Ala Val Glu Ala Val His Ala Trp Arg Asn Ala Leu Thr Gly Ala
    290                 295                 300

Pro Leu Asn Leu Thr Pro Gln Gln Val Val Ala Ile Ala Ser Asn Gly
305                 310                 315                 320
```

-continued

```
Gly Gly Lys Gln Ala Leu Glu Thr Val Gln Arg Leu Leu Pro Val Leu
            325                 330                 335

Cys Gln Ala His Gly Leu Thr Pro Gln Gln Val Val Ala Ile Ala Ser
        340                 345                 350

Asn Gly Gly Lys Gln Ala Leu Glu Thr Val Gln Arg Leu Leu Pro
    355                 360                 365

Val Leu Cys Gln Ala His Gly Leu Thr Pro Gln Gln Val Val Ala Ile
370                 375                 380

Ala Ser Asn Gly Gly Lys Gln Ala Leu Glu Thr Val Gln Arg Leu
385                 390                 395                 400

Leu Pro Val Leu Cys Gln Ala His Gly Leu Thr Pro Gln Gln Val Val
                405                 410                 415

Ala Ile Ala Ser Asn Asn Gly Gly Lys Gln Ala Leu Glu Thr Val Gln
            420                 425                 430

Arg Leu Leu Pro Val Leu Cys Gln Ala His Gly Leu Thr Pro Glu Gln
        435                 440                 445

Val Val Ala Ile Ala Ser Asn Gly Gly Gly Lys Gln Ala Leu Glu Thr
    450                 455                 460

Val Gln Ala Leu Leu Pro Val Leu Cys Gln Ala His Gly Leu Thr Pro
465                 470                 475                 480

Glu Gln Val Val Ala Ile Ala Ser His Asp Gly Gly Lys Gln Ala Leu
                485                 490                 495

Glu Thr Val Gln Arg Leu Leu Pro Val Leu Cys Gln Ala His Gly Leu
            500                 505                 510

Thr Pro Gln Gln Val Val Ala Ile Ala Ser Asn Gly Gly Gly Lys Gln
        515                 520                 525

Ala Leu Glu Thr Val Gln Arg Leu Leu Pro Val Leu Cys Gln Ala His
    530                 535                 540

Gly Leu Thr Pro Gln Gln Val Val Ala Ile Ala Ser Asn Asn Gly Gly
545                 550                 555                 560

Lys Gln Ala Leu Glu Thr Val Gln Arg Leu Leu Pro Val Leu Cys Gln
                565                 570                 575

Ala His Gly Leu Thr Pro Gln Gln Val Val Ala Ile Ala Ser Asn Gly
            580                 585                 590

Gly Gly Lys Gln Ala Leu Glu Thr Val Gln Arg Leu Leu Pro Val Leu
        595                 600                 605

Cys Gln Ala His Gly Leu Thr Pro Gln Gln Val Val Ala Ile Ala Ser
    610                 615                 620

Asn Gly Gly Gly Lys Gln Ala Leu Glu Thr Val Gln Arg Leu Leu Pro
625                 630                 635                 640

Val Leu Cys Gln Ala His Gly Leu Thr Pro Glu Gln Val Val Ala Ile
                645                 650                 655

Ala Ser Asn Gly Gly Gly Lys Gln Ala Leu Glu Thr Val Gln Arg Leu
            660                 665                 670

Leu Pro Val Leu Cys Gln Ala His Gly Leu Thr Pro Glu Gln Val Val
        675                 680                 685

Ala Ile Ala Ser Asn Ile Gly Gly Lys Gln Ala Leu Glu Thr Val Gln
    690                 695                 700

Arg Leu Leu Pro Val Leu Cys Gln Ala His Gly Leu Thr Pro Glu Gln
705                 710                 715                 720

Val Val Ala Ile Ala Ser Asn Asn Gly Gly Lys Gln Ala Leu Glu Thr
                725                 730                 735

Val Gln Arg Leu Leu Pro Val Leu Cys Gln Ala His Gly Leu Thr Pro
```

```
                    740                 745                 750
Glu Gln Val Val Ala Ile Ala Ser Asn Ile Gly Gly Lys Gln Ala Leu
            755                 760                 765
Glu Thr Val Gln Arg Leu Leu Pro Val Leu Cys Gln Ala His Gly Leu
        770                 775                 780
Thr Pro Gln Gln Val Val Ala Ile Ala Ser Asn Gly Gly Gly Lys Gln
785                 790                 795                 800
Ala Leu Glu Thr Val Gln Arg Leu Leu Pro Val Leu Cys Gln Ala Gln
                805                 810                 815
Gly Leu Thr Pro Glu Gln Val Val Ala Ile Ala Ser Asn Gly Gly Gly
            820                 825                 830
Lys Gln Ala Leu Glu Thr Val Gln Arg Leu Leu Pro Val Leu Cys Gln
        835                 840                 845
Ala His Gly Leu Thr Pro Gln Gln Val Val Ala Ile Ala Ser His Asp
    850                 855                 860
Gly Gly Arg Pro Ala Leu Glu Ser Ile Val Ala Gln Leu Ser Arg Pro
865                 870                 875                 880
Asp Pro Ala Leu Ala Ala Leu Thr Asn Asp His Leu Val Ala Leu Ala
                885                 890                 895
Cys Leu Gly Gly Arg Pro Ala Leu Asp Ala Val Lys Lys Gly Leu Pro
            900                 905                 910
His Ala Pro Ala Leu Ile Lys Arg Thr Asn Arg Arg Ile Pro Glu Arg
        915                 920                 925
Thr Ser His Arg Val Ala Lys Gln Leu Val Lys Ser Glu Leu Glu Glu
    930                 935                 940
Lys Lys Ser Glu Leu Arg His Lys Leu Lys Tyr Val Pro His Glu Tyr
945                 950                 955                 960
Ile Glu Leu Ile Glu Ile Ala Arg Asn Ser Thr Gln Asp Arg Ile Leu
                965                 970                 975
Glu Met Lys Val Met Glu Phe Phe Met Lys Val Tyr Gly Tyr Arg Gly
            980                 985                 990
Lys His Leu Gly Gly Ser Arg Lys  Pro Asp Gly Ala Ile  Tyr Thr Val
        995                1000                1005
Gly Ser  Pro Ile Asp Tyr Gly  Val Ile Val Asp Thr  Lys Ala Tyr
        1010                1015                1020
Ser Gly  Gly Tyr Asn Leu Pro  Ile Gly Gln Ala Asp  Glu Met Gln
        1025                1030                1035
Arg Tyr  Val Glu Glu Asn Gln  Thr Arg Asn Lys His  Ile Asn Pro
        1040                1045                1050
Asn Glu  Trp Trp Lys Val Tyr  Pro Ser Ser Val Thr  Glu Phe Lys
        1055                1060                1065
Phe Leu  Phe Val Ser Gly His  Phe Lys Gly Asn Tyr  Lys Ala Gln
        1070                1075                1080
Leu Thr  Arg Leu Asn His Ile  Thr Asn Cys Asn Gly  Ala Val Leu
        1085                1090                1095
Ser Val  Glu Glu Leu Leu Ile  Gly Gly Glu Met Ile  Lys Ala Gly
        1100                1105                1110
Thr Leu  Thr Leu Glu Glu Val  Arg Arg Lys Phe Asn  Asn Gly Glu
        1115                1120                1125
Ile Asn  Phe
        1130

<210> SEQ ID NO 8
```

<211> LENGTH: 3396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

| | | | | | |
|---|---|---|---|---|---|
| atggctccca | aaagaagag | aaaggtagaa | ccaggatcac | ctggtggaca | atcacttatg | 60 |
| gacccaatac | gaagcagaac | gccatcacca | gctagggaac | ttctctctgg | accacagcct | 120 |
| gatggagttc | agccaactgc | agatcgaggt | gtttctccgc | cagccggtgg | ccctttagat | 180 |
| ggactcccag | caagaagaac | aatgtcccgt | accagactcc | caagtccccc | tgccccgtcg | 240 |
| ccagccttt | cagctgactc | cttctctgat | cttcttaggc | aatttgaccc | ttctcttttc | 300 |
| aatacatccc | ttttcgattc | acttcctcct | ttcggcgcac | atcatactga | ggcagccacc | 360 |
| ggcgaatggg | acgaagtcca | agtggttta | agggcagctg | atgctccacc | accgacgatg | 420 |
| agagtcgctg | ttaccgccgc | acgtcctcct | agagccaagc | cagcccctag | aagacgagct | 480 |
| gcgcaaccct | ccgatgcaag | ccctgcagct | caagtagacc | ttcgaacact | aggttactcc | 540 |
| cagcaacaac | aagaaaaaat | aaagccaaag | gttagatcaa | cagttgcaca | acatcacgaa | 600 |
| gccctagtcg | acacggatt | tacacatgct | catatcgtgg | ctctttcaca | acatcctgca | 660 |
| gctcttggaa | cagtcgctgt | caaatatcag | gatatgattg | ctgcattgcc | agaagctact | 720 |
| cacgaagcta | tcgtcggagt | tgggaaacaa | tggtcaggcg | caagagcatt | agaggcgctt | 780 |
| ctcaccgtag | ctggtgaatt | acgaggtcct | ccactccaat | ggatactggg | caattatta | 840 |
| aaaatcgcta | acgaggtgg | agtcactgct | gtcgaagccg | ttcatgcatg | gcgtaacgct | 900 |
| ctcacgggg | ccccactaaa | ccttacccca | caacaagttg | tggcaatagc | ttctaatgga | 960 |
| ggtggtaaac | aagcccttga | gacggttcaa | agacttctac | cagttctttg | tcaggcacat | 1020 |
| ggattgaccc | cacaacaggt | cgtagcaatc | gcatctaaca | ttggtggtaa | gcaagctctt | 1080 |
| gaaacggtac | aaagattact | tcccgtgctt | tgtcaagctc | atggactcac | tcctcaacaa | 1140 |
| gtggtcgcta | ttgcaagtaa | tattggtgga | aagcaagcac | tagaaaccgt | ccaacgactc | 1200 |
| cttcctgttc | tctgtcaagc | acatggtttg | actcctcagc | aggtcgtcgc | aattgcatca | 1260 |
| aataacggag | gcaaacaagc | tttagaaaca | gtacaaagac | tattgcccgt | tctttgccaa | 1320 |
| gcgcatgggt | taactcccga | acaagtcgtt | gccattgcaa | gtaacaatgg | aggtaaacaa | 1380 |
| gctctcgaaa | cggttcaagc | acttttaccc | gttctctgtc | aagcacatgg | actcacacct | 1440 |
| gaacaagtag | ttgctatcgc | atcgaataat | ggtggaaaac | aagcactgga | aactgtacaa | 1500 |
| agactttgc | cagttttatg | tcaagcgcac | ggtcttactc | ctcaacaagt | tgtcgccatt | 1560 |
| gcctctcatg | atggtggaaa | acaagctctt | gaaactgtcc | agagacttct | gcccgttcta | 1620 |
| tgtcaggctc | atgggctaac | ccctcaacag | gttgttgcaa | tcgcatctaa | tggtggagga | 1680 |
| aaacaagctt | tagaaactgt | ccaacgacta | ctgcccgttc | tctgccaagc | acacggactt | 1740 |
| acaccacaac | aggttgtagc | tatagctagc | aatattggcg | gtaaacaggc | tttgaaaaca | 1800 |
| gtacagcggc | ttctaccagt | cttatgccaa | gcccacgggc | ttactcctca | acaagttgtc | 1860 |
| gccattgcct | ctaacggagg | tggaaaacaa | gctcttgaaa | ctgtccagag | acttctgccc | 1920 |
| gttctatgtc | aggctcatgg | gcttactcct | gaacaggttg | tcgcaatagc | ttcaaacatt | 1980 |
| ggcggaaaac | aagctcttga | aacagtgcaa | cgtctcctc | ccgtcctctg | tcaggctcac | 2040 |
| ggacttacgc | ccgaacaagt | tgttgctata | gcttcgaata | ttggtggaaa | acaagctctc | 2100 |

```
gaaaccgtcc aaaggctcct cccagtactt tgccaagcac atggattaac ccctgagcaa    2160
gtagttgcaa ttgcctcgca cgatggagga aagcaagcat tagaaactgt tcagagactt    2220
ttgcctgtcc tgtgtcaagc ccacggtctt acaccagagc aggttgtcgc tatagcttct    2280
aatatcggtg gaaagcaagc tcttgagact gtgcaacgtt tgcttccagt cctctgtcaa    2340
gcacacggac tcactccaca acaggtggtt gcaattgctt caaataatgg tggcaaacaa    2400
gcattagaga ctgtacagag actacttcct gttctttgtc aagcacaagg gctcacccct    2460
gagcaggtag tcgctatcgc ctcacacgac ggcgggaagc aggccctgga gactgttcag    2520
agactactgc ccgtcctatg tcaggctcac ggtctaacac cacaacaagt cgtcgcaatc    2580
gctagtaata ttggaggtcg acctgctcta gagtcgatag tcgcacaact atcacgacct    2640
gatcccgctc ttgcagcatt gacaaacgat catttagtcg cacttgcatg tttaggagga    2700
cgaccagcac ttgatgccgt taagaaagga ctaccgcacg cccctgcatt gattaaaaga    2760
acaaacagac gaatcccgga gagaacttca tcgtgtag ccaagcaact tgtcaaaagt    2820
gaactggagg agaagaaatc tgaacttcgt cataaattga aatatgtgcc tcatgaatat    2880
attgaattaa ttgaaattgc cagaaattcc actcaggata gaattcttga aatgaaggta    2940
atggaatttt ttatgaaagt ttatggatat agaggtaaac atttgggtgg atcaaggaaa    3000
ccggacggag caatttatac tgtcggatct cctattgatt acggtgtgat cgtggatact    3060
aaagcttata gcggaggtta taatctgcca attggccaag cagatgaaat gcaacgatat    3120
gtcgaagaaa atcaaacacg aaacaaacat atcaacccta atgaatggtg gaaagtctat    3180
ccatcttctg taacggaatt taagttttta tttgtgagtg gtcactttaa aggaaactac    3240
aaagctcagc ttacacgatt aaatcatatc actaattgta atggagctgt tcttagtgta    3300
gaagagcttt taattggtgg agaaatgatt aaagccggca cattaacctt agaggaagtg    3360
agacggaaat ttaataacgg cgagataaac ttttga                               3396
```

<210> SEQ ID NO 9
<211> LENGTH: 1131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Ala Pro Lys Lys Arg Lys Val Glu Pro Gly Ser Pro Gly Gly
1               5                   10                  15

Gln Ser Leu Met Asp Pro Ile Arg Ser Arg Thr Pro Ser Pro Ala Arg
            20                  25                  30

Glu Leu Leu Ser Gly Pro Gln Pro Asp Gly Val Gln Pro Thr Ala Asp
        35                  40                  45

Arg Gly Val Ser Pro Pro Ala Gly Gly Pro Leu Asp Gly Leu Pro Ala
    50                  55                  60

Arg Arg Thr Met Ser Arg Thr Arg Leu Pro Ser Pro Ala Pro Ser
65                  70                  75                  80

Pro Ala Phe Ser Ala Asp Ser Phe Ser Asp Leu Leu Arg Gln Phe Asp
                85                  90                  95

Pro Ser Leu Phe Asn Thr Ser Leu Phe Asp Ser Leu Pro Pro Phe Gly
            100                 105                 110

Ala His His Thr Glu Ala Ala Thr Gly Glu Trp Asp Glu Val Gln Ser
        115                 120                 125
```

-continued

```
Gly Leu Arg Ala Ala Asp Ala Pro Pro Thr Met Arg Val Ala Val
    130                 135                 140

Thr Ala Ala Arg Pro Pro Arg Ala Lys Pro Ala Pro Arg Arg Ala
145                 150                 155                 160

Ala Gln Pro Ser Asp Ala Ser Pro Ala Ala Gln Val Asp Leu Arg Thr
                165                 170                 175

Leu Gly Tyr Ser Gln Gln Gln Glu Lys Ile Lys Pro Lys Val Arg
                180                 185                 190

Ser Thr Val Ala Gln His His Glu Ala Leu Val Gly His Gly Phe Thr
        195                 200                 205

His Ala His Ile Val Ala Leu Ser Gln His Pro Ala Ala Leu Gly Thr
    210                 215                 220

Val Ala Val Lys Tyr Gln Asp Met Ile Ala Ala Leu Pro Glu Ala Thr
225                 230                 235                 240

His Glu Ala Ile Val Gly Val Gly Lys Gln Trp Ser Gly Ala Arg Ala
                245                 250                 255

Leu Glu Ala Leu Leu Thr Val Ala Gly Glu Leu Arg Gly Pro Pro Leu
                260                 265                 270

Gln Leu Asp Thr Gly Gln Leu Leu Lys Ile Ala Lys Arg Gly Gly Val
            275                 280                 285

Thr Ala Val Glu Ala Val His Ala Trp Arg Asn Ala Leu Thr Gly Ala
    290                 295                 300

Pro Leu Asn Leu Thr Pro Gln Gln Val Val Ala Ile Ala Ser Asn Gly
305                 310                 315                 320

Gly Gly Lys Gln Ala Leu Glu Thr Val Gln Arg Leu Leu Pro Val Leu
                325                 330                 335

Cys Gln Ala His Gly Leu Thr Pro Gln Gln Val Val Ala Ile Ala Ser
            340                 345                 350

Asn Ile Gly Gly Lys Gln Ala Leu Glu Thr Val Gln Arg Leu Leu Pro
        355                 360                 365

Val Leu Cys Gln Ala His Gly Leu Thr Pro Gln Gln Val Val Ala Ile
    370                 375                 380

Ala Ser Asn Ile Gly Gly Lys Gln Ala Leu Glu Thr Val Gln Arg Leu
385                 390                 395                 400

Leu Pro Val Leu Cys Gln Ala His Gly Leu Thr Pro Gln Gln Val Val
                405                 410                 415

Ala Ile Ala Ser Asn Asn Gly Gly Lys Gln Ala Leu Glu Thr Val Gln
            420                 425                 430

Arg Leu Leu Pro Val Leu Cys Gln Ala His Gly Leu Thr Pro Glu Gln
        435                 440                 445

Val Val Ala Ile Ala Ser Asn Asn Gly Gly Lys Gln Ala Leu Glu Thr
    450                 455                 460

Val Gln Ala Leu Leu Pro Val Leu Cys Gln Ala His Gly Leu Thr Pro
465                 470                 475                 480

Glu Gln Val Val Ala Ile Ala Ser Asn Asn Gly Gly Lys Gln Ala Leu
                485                 490                 495

Glu Thr Val Gln Arg Leu Leu Pro Val Leu Cys Gln Ala His Gly Leu
            500                 505                 510

Thr Pro Gln Gln Val Val Ala Ile Ala Ser His Asp Gly Gly Lys Gln
        515                 520                 525

Ala Leu Glu Thr Val Gln Arg Leu Leu Pro Val Leu Cys Gln Ala His
    530                 535                 540

Gly Leu Thr Pro Gln Gln Val Val Ala Ile Ala Ser Asn Gly Gly Gly
```

```
            545                 550                 555                 560
        Lys Gln Ala Leu Glu Thr Val Gln Arg Leu Leu Pro Val Leu Cys Gln
                        565                 570                 575

Ala His Gly Leu Thr Pro Gln Gln Val Val Ala Ile Ala Ser Asn Ile
                        580                 585                 590

Gly Gly Lys Gln Ala Leu Glu Thr Val Gln Arg Leu Leu Pro Val Leu
                        595                 600                 605

Cys Gln Ala His Gly Leu Thr Pro Gln Gln Val Val Ala Ile Ala Ser
        610                 615                 620

Asn Gly Gly Lys Gln Ala Leu Glu Thr Val Gln Arg Leu Leu Pro
        625                 630                 635                 640

Val Leu Cys Gln Ala His Gly Leu Thr Pro Glu Gln Val Val Ala Ile
                        645                 650                 655

Ala Ser Asn Ile Gly Gly Lys Gln Ala Leu Glu Thr Val Gln Arg Leu
                        660                 665                 670

Leu Pro Val Leu Cys Gln Ala His Gly Leu Thr Pro Glu Gln Val Val
                        675                 680                 685

Ala Ile Ala Ser Asn Ile Gly Gly Lys Gln Ala Leu Glu Thr Val Gln
        690                 695                 700

Arg Leu Leu Pro Val Leu Cys Gln Ala His Gly Leu Thr Pro Glu Gln
        705                 710                 715                 720

Val Val Ala Ile Ala Ser His Asp Gly Gly Lys Gln Ala Leu Glu Thr
                        725                 730                 735

Val Gln Arg Leu Leu Pro Val Leu Cys Gln Ala His Gly Leu Thr Pro
                        740                 745                 750

Glu Gln Val Val Ala Ile Ala Ser Asn Ile Gly Gly Lys Gln Ala Leu
                        755                 760                 765

Glu Thr Val Gln Arg Leu Leu Pro Val Leu Cys Gln Ala His Gly Leu
                        770                 775                 780

Thr Pro Gln Gln Val Val Ala Ile Ala Ser Asn Asn Gly Gly Lys Gln
        785                 790                 795                 800

Ala Leu Glu Thr Val Gln Arg Leu Leu Pro Val Leu Cys Gln Ala Gln
                        805                 810                 815

Gly Leu Thr Pro Glu Gln Val Val Ala Ile Ala Ser His Asp Gly Gly
                        820                 825                 830

Lys Gln Ala Leu Glu Thr Val Gln Arg Leu Leu Pro Val Leu Cys Gln
                        835                 840                 845

Ala His Gly Leu Thr Pro Gln Gln Val Val Ala Ile Ala Ser Asn Ile
                        850                 855                 860

Gly Gly Arg Pro Ala Leu Glu Ser Ile Val Ala Gln Leu Ser Arg Pro
        865                 870                 875                 880

Asp Pro Ala Leu Ala Leu Thr Asn Asp His Leu Val Ala Leu Ala
                        885                 890                 895

Cys Leu Gly Gly Arg Pro Ala Leu Asp Ala Val Lys Lys Gly Leu Pro
                        900                 905                 910

His Ala Pro Ala Leu Ile Lys Arg Thr Asn Arg Arg Ile Pro Glu Arg
                        915                 920                 925

Thr Ser His Arg Val Ala Lys Gln Leu Val Lys Ser Glu Leu Glu Glu
                        930                 935                 940

Lys Lys Ser Glu Leu Arg His Lys Leu Lys Tyr Val Pro His Glu Tyr
        945                 950                 955                 960

Ile Glu Leu Ile Glu Ile Ala Arg Asn Ser Thr Gln Asp Arg Ile Leu
                        965                 970                 975
```

```
Glu Met Lys Val Met Glu Phe Phe Met Lys Val Tyr Gly Tyr Arg Gly
            980                 985                 990

Lys His Leu Gly Gly Ser Arg Lys Pro Asp Gly Ala Ile Tyr Thr Val
        995                1000                1005

Gly Ser Pro Ile Asp Tyr Gly Val Ile Val Asp Thr Lys Ala Tyr
    1010                1015                1020

Ser Gly Gly Tyr Asn Leu Pro Ile Gly Gln Ala Asp Glu Met Gln
    1025                1030                1035

Arg Tyr Val Glu Glu Asn Gln Thr Arg Asn Lys His Ile Asn Pro
    1040                1045                1050

Asn Glu Trp Trp Lys Val Tyr Pro Ser Ser Val Thr Glu Phe Lys
    1055                1060                1065

Phe Leu Phe Val Ser Gly His Phe Lys Gly Asn Tyr Lys Ala Gln
    1070                1075                1080

Leu Thr Arg Leu Asn His Ile Thr Asn Cys Asn Gly Ala Val Leu
    1085                1090                1095

Ser Val Glu Glu Leu Leu Ile Gly Gly Glu Met Ile Lys Ala Gly
    1100                1105                1110

Thr Leu Thr Leu Glu Glu Val Arg Arg Lys Phe Asn Asn Gly Glu
    1115                1120                1125

Ile Asn Phe
    1130

<210> SEQ ID NO 10
<211> LENGTH: 1980
<212> TYPE: DNA
<213> ORGANISM: Solanum tuberosum

<400> SEQUENCE: 10
atggcggctg ctgcctcacc atctccatgt ttctccaaaa ccctacctcc atcttcctcc      60
aaatcttcca ccattcttcc tagatctacc ttccctttcc acaatcaccc tcaaaaagcc     120 tcacccttc atctcaccca cacccatcat catcgtcgtg tttcgccgt tccaatgtc       180 gtcatatcca ctaccaccca taacgacgtt tctgaacctg aaacattcgt ttcccgtttc     240
gcccctgacg aacccagaaa gggttgtgat gttcttgtgg aggcacttga aagggagggg     300
gttacggatg tatttgcgta cccaggaggt gcttctatgg agattcatca ggctttgaca     360
cgttcgaata ttattcgtaa tgtgctgcca cgtcatgagc aaggtggtgt gtttgctgca     420
gagggttacg cacgggcgac tgggttccct ggtgtttgca ttgctacctc tggtccggga     480
gctacgaatc ttgttagtgg tcttgcggat gctttgttgg atagtattcc gattgttgct     540
attacgggtc aagtgccgag gaggatgatt ggtactgatg cgtttcagga acgcctatt      600 gttgaggtaa cgagatctat tacgaagcat aattatcttg ttatggatgt agaggatatt     660 cctaggggttg ttcgtgaagc gttttttcta gcgaaatcgg gacggcctgg gccggttttg    720
attgatgtac ctaaggatat tcagcaacaa ttggtgatac ctaattggga tcagccaatg    780
aggttgcctg gttacatgtc taggttacct aaattgccta atgagatgct tttggaacaa    840
attattaggc tgatttcgga gtcgaagaag cctgttttgt atgtgggtgg tgggtgtttg    900
caatcaagtg aggagctgag acgatttgtg gagcttacgg gtattcctgt ggcgagtact    960
ttgatgggtc ttggagcttt tccaactggg gatgagcttt cccttcaaat gttgggtatg   1020
catgggactg tgtatgctaa ttatgctgtg gatggtagtg atttgttgct tgcatttggg   1080
gtgaggtttg atgatcgagt tactggtaaa ttggaagctt ttgctagccg agcgaaaatt   1140
```

-continued

```
gtccacattg atattgattc ggctgagatt ggaaagaaca agcaacctca tgtttccatt    1200
tgtgcagata tcaagttggc attacagggt ttgaattcca tattggaggg taaagaaggt    1260
aagctgaagt tggactttc tgcttggaga caggagttaa cggaacagaa ggtgaagtac     1320
ccattgagtt ttaagacttt tggtgaagcc atccctccac aatatgctat tcaggttctt    1380
gatgagttaa ctaacggaaa tgccattatt agtactggtg tggggcaaca ccagatgtgg    1440
gctgcccaat actataagta caaaaagcca caccaatggt tgacatctgg tggattagga    1500
gcaatgggat ttggtttgcc tgctgcaata ggtgcggctg ttggaagacc gggtgagatt    1560
gtggttgaca ttgatggtga cgggagtttt atcatgaatg tgcaggagtt agcaacaatt    1620
aaggtggaga atctcccagt taagattatg ttgctgaata atcaacactt gggaatggtg    1680
gttcaatggg aggatcgatt ctataaggct aacagagcac acacttactt gggtgatcct    1740
gctaatgagg aagagatctt ccctaatatg ttgaaattcg cagaggcttg tggcgtacct    1800
gctgcaagag tgtcacacag ggatgatctt agagctgcca ttcaaaagat gttagacact    1860
cctgggccat acttgttgga tgtgattgta cctcatcagg agcacgttct acctatgatt    1920
cccagtggcg tgctttcaa agatgtgatc acagagggtg atgggagacg ttcatattga     1980
```

<210> SEQ ID NO 11
<211> LENGTH: 659
<212> TYPE: PRT
<213> ORGANISM: Solanum tuberosum

<400> SEQUENCE: 11

```
Met Ala Ala Ala Ser Pro Ser Pro Cys Phe Ser Lys Thr Leu Pro
 1               5                  10                  15

Pro Ser Ser Lys Ser Ser Thr Ile Leu Pro Arg Ser Thr Phe Pro
                20                  25                  30

Phe His Asn His Pro Gln Lys Ala Ser Pro Leu His Leu Thr His Thr
                35                  40                  45

His His His Arg Arg Gly Phe Ala Val Ser Asn Val Val Ile Ser Thr
                50                  55                  60

Thr Thr His Asn Asp Val Ser Glu Pro Glu Thr Phe Val Ser Arg Phe
65                  70                  75                  80

Ala Pro Asp Glu Pro Arg Lys Gly Cys Asp Val Leu Val Glu Ala Leu
                85                  90                  95

Glu Arg Glu Gly Val Thr Asp Val Phe Ala Tyr Pro Gly Gly Ala Ser
                100                 105                 110

Met Glu Ile His Gln Ala Leu Thr Arg Ser Asn Ile Ile Arg Asn Val
                115                 120                 125

Leu Pro Arg His Glu Gln Gly Gly Val Phe Ala Ala Glu Gly Tyr Ala
                130                 135                 140

Arg Ala Thr Gly Phe Pro Gly Val Cys Ile Ala Thr Ser Gly Pro Gly
145                 150                 155                 160

Ala Thr Asn Leu Val Ser Gly Leu Ala Asp Ala Leu Leu Asp Ser Ile
                165                 170                 175

Pro Ile Val Ala Ile Thr Gly Gln Val Pro Arg Arg Met Ile Gly Thr
                180                 185                 190

Asp Ala Phe Gln Glu Thr Pro Ile Val Glu Val Thr Arg Ser Ile Thr
                195                 200                 205

Lys His Asn Tyr Leu Val Met Asp Val Glu Asp Ile Pro Arg Val Val
                210                 215                 220
```

```
Arg Glu Ala Phe Phe Leu Ala Lys Ser Gly Arg Pro Gly Pro Val Leu
225                 230                 235                 240

Ile Asp Val Pro Lys Asp Ile Gln Gln Leu Val Ile Pro Asn Trp
            245                 250                 255

Asp Gln Pro Met Arg Leu Pro Gly Tyr Met Ser Arg Leu Pro Lys Leu
            260                 265                 270

Pro Asn Glu Met Leu Leu Glu Gln Ile Ile Arg Leu Ile Ser Glu Ser
            275                 280                 285

Lys Lys Pro Val Leu Tyr Val Gly Gly Cys Leu Gln Ser Ser Glu
290                 295                 300

Glu Leu Arg Arg Phe Val Glu Leu Thr Gly Ile Pro Val Ala Ser Thr
305                 310                 315                 320

Leu Met Gly Leu Gly Ala Phe Pro Thr Gly Asp Glu Leu Ser Leu Gln
                325                 330                 335

Met Leu Gly Met His Gly Thr Val Tyr Ala Asn Tyr Ala Val Asp Gly
                340                 345                 350

Ser Asp Leu Leu Leu Ala Phe Gly Val Arg Phe Asp Asp Arg Val Thr
            355                 360                 365

Gly Lys Leu Glu Ala Phe Ala Ser Arg Ala Lys Ile Val His Ile Asp
370                 375                 380

Ile Asp Ser Ala Glu Ile Gly Lys Asn Lys Gln Pro His Val Ser Ile
385                 390                 395                 400

Cys Ala Asp Ile Lys Leu Ala Leu Gln Gly Leu Asn Ser Ile Leu Glu
                405                 410                 415

Gly Lys Glu Gly Lys Leu Lys Leu Asp Phe Ser Ala Trp Arg Gln Glu
                420                 425                 430

Leu Thr Glu Gln Lys Val Lys Tyr Pro Leu Ser Phe Lys Thr Phe Gly
            435                 440                 445

Glu Ala Ile Pro Pro Gln Tyr Ala Ile Gln Val Leu Asp Glu Leu Thr
            450                 455                 460

Asn Gly Asn Ala Ile Ile Ser Thr Gly Val Gly Gln His Gln Met Trp
465                 470                 475                 480

Ala Ala Gln Tyr Tyr Lys Tyr Lys Lys Pro His Gln Trp Leu Thr Ser
                485                 490                 495

Gly Gly Leu Gly Ala Met Gly Phe Gly Leu Pro Ala Ala Ile Gly Ala
                500                 505                 510

Ala Val Gly Arg Pro Gly Glu Ile Val Val Asp Ile Asp Gly Asp Gly
            515                 520                 525

Ser Phe Ile Met Asn Val Gln Glu Leu Ala Thr Ile Lys Val Glu Asn
530                 535                 540

Leu Pro Val Lys Ile Met Leu Leu Asn Asn Gln His Leu Gly Met Val
545                 550                 555                 560

Val Gln Trp Glu Asp Arg Phe Tyr Lys Ala Asn Arg Ala His Thr Tyr
                565                 570                 575

Leu Gly Asp Pro Ala Asn Glu Glu Glu Ile Phe Pro Asn Met Leu Lys
            580                 585                 590

Phe Ala Glu Ala Cys Gly Val Pro Ala Ala Arg Val Ser His Arg Asp
            595                 600                 605

Asp Leu Arg Ala Ala Ile Gln Lys Met Leu Asp Thr Pro Gly Pro Tyr
            610                 615                 620

Leu Leu Asp Val Ile Val Pro His Gln Glu His Val Leu Pro Met Ile
625                 630                 635                 640

Pro Ser Gly Gly Ala Phe Lys Asp Val Ile Thr Glu Gly Asp Gly Arg
```

Arg Ser Tyr

<210> SEQ ID NO 12
<211> LENGTH: 1980
<212> TYPE: DNA
<213> ORGANISM: Solanum tuberosum

<400> SEQUENCE: 12

| | | | | | |
|---|---|---|---|---|---|
| atggcggctg | ctgcctcacc | atctccatgt | ttctccaaaa | ccctacctcc | atcttcctcc | 60 |
| aaatcttcca | ccattcttcc | tagatctacc | ttcccttttcc | acaatcaccc | tcaaaaagcc | 120 |
| tcacccttc | atctcaccca | cacccatcat | catcgtcgtg | gtttcgccgt | ttccaatgtc | 180 |
| gtcatatcca | ctaccaccca | taacgacgtt | tctgaacctg | aaacattcgt | ttcccgtttc | 240 |
| gcccctgacg | aacccagaaa | gggttgtgat | gttcttgtgg | aggcacttga | aagggagggg | 300 |
| gttacggatg | tatttgcgta | cccaggaggt | gcttctatgg | agattcatca | ggctttgaca | 360 |
| cgttcgaata | ttattcgtaa | tgtgctgcca | cgtcatgagc | aaggtggtgt | gtttgctgca | 420 |
| gagggttacg | cacgggcgac | tgggttccct | ggtgtttgca | ttgctacctc | tggtccggga | 480 |
| gctacgaatc | ttgttagtgg | tcttgcggat | gctttgttgg | atagtattcc | gattgttgct | 540 |
| attacgggtc | aagtgccgag | gaggatgatt | ggtactgatg | cgtttcagga | aacgcctatt | 600 |
| gttgaggtaa | cgagatctat | tacgaagcat | aattatcttg | ttatggatgt | agaggatatt | 660 |
| cctagggttg | ttcgtgaagc | gttttttcta | gcgaaatcgg | gacggcctgg | gccggttttg | 720 |
| attgatgtac | ctaaggatat | tcagcaacaa | ttggtgatac | ctaattggga | tcagccaatg | 780 |
| aggttgcctg | gttacatgtc | tagattacct | aaattgccta | atgagatgct | tttggaacaa | 840 |
| attattaggc | tgatttcgga | gtcgaagaag | cctgttttgt | atgtgggtgg | tgggtgtttg | 900 |
| caatcaagtg | aggagctgag | acgatttgtg | gagcttacgg | gtattcctgt | ggcgagtact | 960 |
| ttgatgggtc | ttggagcttt | tccaactggg | gatgagcttt | cccttcaaat | gttgggtatg | 1020 |
| catgggactg | tgtatgctaa | ttatgctgtg | gatggtagtg | atttgttgct | tgcatttggg | 1080 |
| gtgaggtttg | atgatcgagt | tactggtaaa | ttggaagctt | tgctagccg | agcgaaaatt | 1140 |
| gtccacattg | atattgattc | ggctgagatt | ggaaagaaca | agcaacctca | tgtttccatt | 1200 |
| tgtgcagata | tcaagttggc | attacagggt | ttgaattcca | tattggaggg | taaagaaggt | 1260 |
| aagctgaagt | tggacttttc | tgcttggaga | caggagttaa | cggaacagaa | ggtgaagtac | 1320 |
| ccattgagtt | ttaagacttt | tggtgaagcc | atccctccac | aatatgctat | tcaggttctt | 1380 |
| gatgagttaa | ctaacggaaa | tgccattatt | agtactggtg | tggggcaaca | ccagatgtgg | 1440 |
| gctgcccaat | actataagta | caaaaagcca | caccaatggt | tgacatctgg | tggattagga | 1500 |
| gcaatgggat | ttggtttgcc | tgctgcaata | ggtgcggctg | ttggaagacc | gggtgagatt | 1560 |
| gtggttgaca | ttgatggtga | cgggagtttt | atcatgaatg | tgcaggagtt | agcaacaatt | 1620 |
| aaggtggaga | atctcccagt | taagattatg | ttgctgaata | tcaacacttt | gggaatggtg | 1680 |
| gttcaactgg | aggatcgatt | ctataaggct | aacagagcac | acacttactt | gggtgatcct | 1740 |
| gctaatgagg | aagagatctt | ccctaatatg | ttgaaattcg | cagaggcttg | tggcgtacct | 1800 |
| gctgcaagag | tgtcacacag | ggatgatctt | agagctgcca | ttcaaaagat | gttagacact | 1860 |
| cctgggccat | acttgttgga | tgtgattgta | cctcatcagg | agcacgttct | acctatgatt | 1920 |
| cccattggcg | gtgctttcaa | agatgtgatc | acagaggggtg | atgggagacg | ttcatattga | 1980 |

<210> SEQ ID NO 13
<211> LENGTH: 659
<212> TYPE: PRT
<213> ORGANISM: Solanum tuberosum

<400> SEQUENCE: 13

```
Met Ala Ala Ala Ser Pro Ser Pro Cys Phe Ser Lys Thr Leu Pro
1               5                   10                  15

Pro Ser Ser Ser Lys Ser Ser Thr Ile Leu Pro Arg Ser Thr Phe Pro
            20                  25                  30

Phe His Asn His Pro Gln Lys Ala Ser Pro Leu His Leu Thr His Thr
        35                  40                  45

His His His Arg Arg Gly Phe Ala Val Ser Asn Val Val Ile Ser Thr
    50                  55                  60

Thr Thr His Asn Asp Val Ser Glu Pro Glu Thr Phe Val Ser Arg Phe
65                  70                  75                  80

Ala Pro Asp Glu Pro Arg Lys Gly Cys Asp Val Leu Val Glu Ala Leu
                85                  90                  95

Glu Arg Glu Gly Val Thr Asp Val Phe Ala Tyr Pro Gly Gly Ala Ser
            100                 105                 110

Met Glu Ile His Gln Ala Leu Thr Arg Ser Asn Ile Ile Arg Asn Val
        115                 120                 125

Leu Pro Arg His Glu Gln Gly Gly Val Phe Ala Ala Glu Gly Tyr Ala
    130                 135                 140

Arg Ala Thr Gly Phe Pro Gly Val Cys Ile Ala Thr Ser Gly Pro Gly
145                 150                 155                 160

Ala Thr Asn Leu Val Ser Gly Leu Ala Asp Ala Leu Leu Asp Ser Ile
                165                 170                 175

Pro Ile Val Ala Ile Thr Gly Gln Val Pro Arg Arg Met Ile Gly Thr
            180                 185                 190

Asp Ala Phe Gln Glu Thr Pro Ile Val Glu Val Thr Arg Ser Ile Thr
        195                 200                 205

Lys His Asn Tyr Leu Val Met Asp Val Glu Asp Ile Pro Arg Val Val
    210                 215                 220

Arg Glu Ala Phe Phe Leu Ala Lys Ser Gly Arg Pro Gly Pro Val Leu
225                 230                 235                 240

Ile Asp Val Pro Lys Asp Ile Gln Gln Gln Leu Val Ile Pro Asn Trp
                245                 250                 255

Asp Gln Pro Met Arg Leu Pro Gly Tyr Met Ser Arg Leu Pro Lys Leu
            260                 265                 270

Pro Asn Glu Met Leu Leu Glu Gln Ile Ile Arg Leu Ile Ser Glu Ser
        275                 280                 285

Lys Lys Pro Val Leu Tyr Val Gly Gly Gly Cys Leu Gln Ser Ser Glu
    290                 295                 300

Glu Leu Arg Arg Phe Val Glu Leu Thr Gly Ile Pro Val Ala Ser Thr
305                 310                 315                 320

Leu Met Gly Leu Gly Ala Phe Pro Thr Gly Asp Glu Leu Ser Leu Gln
                325                 330                 335

Met Leu Gly Met His Gly Thr Val Tyr Ala Asn Tyr Ala Val Asp Gly
            340                 345                 350

Ser Asp Leu Leu Leu Ala Phe Gly Val Arg Phe Asp Asp Arg Val Thr
        355                 360                 365

Gly Lys Leu Glu Ala Phe Ala Ser Arg Ala Lys Ile Val His Ile Asp
    370                 375                 380
```

```
Ile Asp Ser Ala Glu Ile Gly Lys Asn Lys Gln Pro His Val Ser Ile
385                 390                 395                 400

Cys Ala Asp Ile Lys Leu Ala Leu Gln Gly Leu Asn Ser Ile Leu Glu
            405                 410                 415

Gly Lys Glu Gly Lys Leu Lys Leu Asp Phe Ser Ala Trp Arg Gln Glu
        420                 425                 430

Leu Thr Glu Gln Lys Val Lys Tyr Pro Leu Ser Phe Lys Thr Phe Gly
    435                 440                 445

Glu Ala Ile Pro Pro Gln Tyr Ala Ile Gln Val Leu Asp Glu Leu Thr
450                 455                 460

Asn Gly Asn Ala Ile Ile Ser Thr Gly Val Gly Gln His Gln Met Trp
465                 470                 475                 480

Ala Ala Gln Tyr Tyr Lys Tyr Lys Lys Pro His Gln Trp Leu Thr Ser
                485                 490                 495

Gly Gly Leu Gly Ala Met Gly Phe Gly Leu Pro Ala Ala Ile Gly Ala
            500                 505                 510

Ala Val Gly Arg Pro Gly Glu Ile Val Val Asp Ile Asp Gly Asp Gly
        515                 520                 525

Ser Phe Ile Met Asn Val Gln Glu Leu Ala Thr Ile Lys Val Glu Asn
530                 535                 540

Leu Pro Val Lys Ile Met Leu Leu Asn Asn Gln His Leu Gly Met Val
545                 550                 555                 560

Val Gln Leu Glu Asp Arg Phe Tyr Lys Ala Asn Arg Ala His Thr Tyr
                565                 570                 575

Leu Gly Asp Pro Ala Asn Glu Glu Glu Ile Phe Pro Asn Met Leu Lys
            580                 585                 590

Phe Ala Glu Ala Cys Gly Val Pro Ala Ala Arg Val Ser His Arg Asp
595                 600                 605

Asp Leu Arg Ala Ala Ile Gln Lys Met Leu Asp Thr Pro Gly Pro Tyr
        610                 615                 620

Leu Leu Asp Val Ile Val Pro His Gln Glu His Val Leu Pro Met Ile
625                 630                 635                 640

Pro Ile Gly Gly Ala Phe Lys Asp Val Ile Thr Glu Gly Asp Gly Arg
                645                 650                 655

Arg Ser Tyr

<210> SEQ ID NO 14
<211> LENGTH: 13057
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
tggcaggata tataccggtg taaacgaagt gtgtgtggtt gatccaaaat ctatcgtacc       60
tttagaaagt gtagctatga aggatagtct cacttatgaa gaactaccta ttgagattct     120
tgatcgtcag gtccgaaggt tgagaaaaat agaagtcgct tcagttacgg ctttgtggag     180
gagtaagggt accagttata caccctacat tctactcgag tcattatgat gatgtctcac     240
gaccaaatca aatcaaagtt aaataaatat cgaaccgaac gcccactctg tatgagtatg     300
gcaaaagatt ttgagagaat caagttgcat aaaagcctaa ttttcatgga acatacaaat     360
tgagtctcat aatagcccaa actcacagcc atgaacccaa attgggtaaa gtttgcaag      420 acgttcatca aacagttagg aaacataaaa tggcgctaga tatataataa attttttaa     480
```

```
catatggtgt gattgatagt tatatactaa agatgtttgc ttagttacgt aattttttca      540
aaaaaaaaag gtacattatc aatcatcagt cacaaaatat taaaagttac tgtttgtttt      600
ttaaattcca tgtcgaattt aattgaatga cacttaaatt gggacgaacg gtgtaatttc      660
ttttgactat tctactagta tctatccaca gcacgtgttg ttcctttctt ctttcgtttt      720
tcatttactt gacattatta ggagacttgg ccctgaactc caactattct aagctgacct      780
ttcttttcct ttaccaatta tcttcttctt tctaatttcg ttttacgcgt agtactgcct      840
gaattttctg actttcaacg tttgttattc atgcttgaaa acgaaatacc agctaacaaa      900
agatgaatta ttgtgtttac aagacttggg ccgttgactc ttactttccc ttcctcatcc      960
tcacatttag aaaaaagaaa tttaacgaaa aattaaagga gatggctgaa attcttctca     1020
cagcagtcat caataaatca atagaaatag ctggaaatgt actctttcaa gaaggtacgc     1080
gtttatattg gttgaaagag gacatcgatt ggctccagag agaaatgaga cacattcgat     1140
catatgtaga caatgcaaag gcaaggaagt tggaggcga ttcaagggtg aaaaacttat      1200
taaaagatat tcaacaactg gcaggtgatg tggaggatct attagatgag tttcttccaa     1260
aaattcaaca atccaataag ttcatttgtt gccttaagac ggtttctttt gccgatgagt     1320
ttgctatgga gattgagaag ataaaaagaa gagttgctga tattgaccgt gtaaggacaa     1380
cttacagcat cacagataca agtaacaata atgatgattg cattccattg gaccggagaa     1440
gattgttcct tcatgctgat gaaacagagg tcatcggtct ggaagatgac ttcaatacac     1500
tacaagccaa attacttgat catgatttgc cttatggagt tgtttcaata gttggcatgc     1560
ccggtttggg aaaaacaact cttgccaaga aactttatag gcatgtctgt catcaatttg     1620
agtgttcggg actggtctat gtttcacaac agccaagggc gggagaaatc ttacatgaca     1680
tagccaaaca agttggactg acggaagagg aaaggaaaga aaacttggag aacaacctac     1740
gatcactctt gaaaataaaa aggtatgtta ttctcttaga tgacatttgg gatgttgaaa     1800
tttgggatga tctaaaactt gtccttcctg aatgtgattc aaaaattggc agtaggataa     1860
ttataacctc tcgaaatagt aatgtaggca gatacatagg agggatttc tcaatccacg      1920 tgttgcaacc cctagattca gagaaaagct ttgaactctt taccaagaaa atctttaatt     1980
ttgttaatga taattgggcc aatgcttcac cagacttggt aaatattggt agatgtatag     2040
ttgagagatg tggaggtata ccgctagcaa ttgtggtgac tgcaggcatg ttaagggcaa     2100
gaggaagaac agaacatgca tggaacagag tacttgagag tatggctcat aaaattcaag     2160
atggatgtgg taaggtattg gctctgagtt acaatgattt gcccattgca ttaaggccat     2220
gtttcttgta ctttggtctt taccccgagg accatgaaat tcgtgctttt gatttgacaa     2280
atatgtggat tgctgagaag ctgatagttg taaatactgg caatgggcga gaggctgaaa     2340
gtttggcgga tgatgtccta aatgatttgg tttcaagaaa cttgattcaa gttgccaaaa     2400
ggacatatga tggaagaatt tcaagttgtc gcatacatga cttgttacat agtttgtgtg     2460
tggacttggc taaggaaagt aacttctttc acacggagca caatgcattt ggtgatccta     2520
gcaatgttgc tagggtgcga aggattacat tctactctga tgataatgcc atgaatgagt     2580
tcttccattt aaatcctaag cctatgaagc ttcgttcact tttctgtttc acaaaagacc     2640
gttgcatatt ttctcaaatg gctcatctta acttcaaatt attgcaagtg ttggttgtag     2700
tcatgtctca aaagggttat cagcatgtta ctttcccca aaaaattggg aacatgagtt      2760
gcctacgtta tgtgcgattg gagggggcaa ttagagtaaa attgccaaat agtattgtca     2820
```

```
agctcaaatg tctagagacc ctggatatat ttcatagctc tagtaaactt ccttttggtg    2880
tttgggagtc taaaatattg agacatcttt gttacacaga agaatgttac tgtgtctctt    2940
ttgcaagtcc attttgccga atcatgcctc ctaataatct acaaactttg atgtgggtgg    3000
atgataaatt ttgtgaacca agattgttgc accgattgat aaatttaaga acattgtgta    3060
taatggatgt atccggttct accattaaga tattatcagc attgagccct gtgcctagag    3120
cgttggaggt tctgaagctc agattttca agaacacgag tgagcaaata aacttgtcgt    3180
cccatccaaa tattgtcgag ttgggtttgg ttggtttctc agcaatgctc ttgaacattg    3240
aagcattccc tccaaatctt gtcaagctta atcttgtcgg cttgatggta gacggtcatc    3300
tattggcagt gcttaagaaa ttgcccaaat taaggatact tatattgctt tggtgcagac    3360
atgatgcaga aaaatggat ctctctggtg atagctttcc gcaacttgaa gttttgtata    3420
ttgaggatgc acaagggttg tctgaagtaa cgtgcatgga tgatatgagt atgcctaaat    3480
tgaaaaagct atttcttgta caaggcccaa acatttcccc aattagtctc agggtctcgg    3540
aacggcttgc aaagttgaga atatcacagg tactataaat aattatttac gtttaatatc    3600
catgattttt ttaaatttgt atttagttca tcaactaaat attccatgtc taataaattg    3660
cagggatgcc tttgaaaatg attctgtgtt ggagagaatc ttctgatgcc tgttggtatt    3720
ataatactaa taataagaga aaagtttga ttactgtttc aagttaattg cttgtgattt    3780
gtaaaaacaa attacttta tatttctctt tgttttattt tatgtttatt tatctttaat    3840
taatggagta ataaaataaa atcttattt tcaatagaaa aaagtagacc ttatttgtgg    3900
tgcatgtatg gtatcttttt gaaatttttg atatatttgc tctttgattc gaatttcttg    3960
cttatatgat gatttgcata aatataaat attatacaaa tacctatggg ttggaaaata    4020
tagaaatatg ccaatcaaat gtatacaaaa atcattaata gatagaatcg taaaagatat    4080
acaaatgaga aatgcttgac taagaagctt cgtgcaacct ctcacactga gcacaatgca    4140
tttggtgatc tcggcactat tgctgttact tgtaagacta cgttccccaa taagtctttc    4200
caaacggctt gcaaagctga gaatatgaaa atctcatagg ttagtttgct gcgttaatta    4260
tttacattta atatgctcga taaggtgatt ttaaaaaaat ttgtactagt taattcatga    4320
actaaatatt tcatttaata ctccataatt ctgaatatgg aaaataaata atatttaata    4380
acaagaataa aatgataaat tattcattga ttttataaat tggataaata ttattaaata    4440
ttcttaaata atataatgaa caagtgaaga tgaacggagg gagtatgaag cctcttttca    4500
aaggggcccc aagtgtctga gacaaccaaa actgaaagtg ggaaaccaaa ctctaagtca    4560
aagactttat atacaaaatg gtataaatat aattatttaa tttactatcg ggttatcgat    4620
taacccgtta agaaaaaact tcaaaccgtt aagaaccgat aacccgataa caaaaaaaat    4680
ctaaatcgtt atcaaaaccg ctaaactaat aacccaatat tgataaacca ataacttttt    4740
ttattcgggt tatcggtttc agttctgttt ggaacaatcc tagtgtccta attattgttt    4800
tgagaaccaa gaaaacaaaa acttacgtcg caaatatttc agtaaatact tgtatatctc    4860
agtgataatt gatttccaac atgtataatt atcatttacg taataataga tggtttccga    4920
aacttacgct tccctttttt cttttgcagt cgtatggaat aaaagttgga tatgaaggca    4980
ttcccgggcc ttcaggtgga agagacggag ctgcttcaca aggaggggt tgttgtactt    5040 gaaaatgggc atttattgtt cgcaaaccta tcatgttcct atggttgttt atttgtagtt    5100
tggtgttctt aatatcgagt gttctttagt ttgttccttt taatgaaagg ataatatctg    5160
tgcaaaaata agtaaattcg gtacataaag acattttttt ttgcattttc tgtttatgga    5220
```

```
gttgtcaaat gtgaatttat ttcatagcat gtgagtttcc tctccttttt catgtgccct   5280
tgggccttgc atgtttcttg caccgcagtg tgccagggct gtcggcagat ggacataaat   5340
ggcacaccgc tcggctcgtg aaagagtat ggtcagtttc attgataagt atttactcgt    5400
attcggtgtt tacatcaagt taatatgttc aaacacatgt gatatcatac atccattagt   5460
taagtataaa tgccaacttt ttacttgaat cgccgaataa atttacttac gtccaatatt   5520
tagttttgtg tgtcaaacat atcatgcact atttgattaa gaataaataa acgatgtgta   5580
atttgaaaac caattagaaa agaagtatga cgggattgat gttctgtgaa atcactggta   5640
aattggacgg acgatgaaat ttgatcgtcc atttaagcat agcaacatgg gtctttagtc   5700
atcatcatta tgttataatt attttcttga aacttgatac accaactttc attgggaaag   5760
tgacagcata gtataaacta taatatcaat tctggcaatt tcgaattatt ccaaatctct   5820
tttgtcattt catttcctcc cctatgtctg caagtaccaa ttatttaagt acaaaaaatc   5880
ttgattaaac aatttatttt ctcactaata atcacattta atcatcaacg gttcatacac   5940
gtctgtcact cttttttat tctctcaagc gcatgtgatc ataccaatta tttaaataca    6000
aaaaatcttg attaaacaat tcagtttctc actaataatc acatttaatc atcaacggtt   6060
catacacatc cgtcactctt tttttattct ctcaagcgca tgtgatcata ccaattattt   6120
aaatacaaaa aatcttgatt aaacaattca ttttctcact aataatcaca tttaatcatc   6180
aacggtttat acacgtccgc cactcttttt ttattctctc aagcgtatgt gatcatatct   6240
aactctcgtg caaacaagtg aaatgacgtt cactaataaa taatcttttg aatactttgt   6300
tcagtttaat ttatttaatt tgataagaat tttttttatta ttgaatttttt attgttttaa   6360 attaaaaata agttaaatat atcaaaatat cttttaattt tattttttgaa aaataacgta   6420 gttcaaacaa attaaaattg agtaactgtt tttcgaaaaa taatgattct aatagtatat   6480 tcttttcat cattagatat tttttttaag ctaagtacaa aagtcatatt tcaatcccca    6540
aaatagcctc aatcacaaga aatgcttaaa tccccaaaat accctcaatc acaagacgtg   6600
tgtaccaatc ataccatatgg tcctctcgta aattccgaca aaatcaggtc tataaagtta   6660
cccttgatat cagtattata aaactaaaaa tctcagctgt aattcaagtg caatcacact   6720
ctaccacaca ctctctagta gagagatcag ttgataacaa gcttgttaac ggatccataa   6780
ttgtaactga tttattcttg aataacaact tcaatgaaat caagcaacaa agctgatttc   6840
aacataaaaa aacagaacaa gaaaacaaaa acagagcatc atccatcaaa gtgtaatctc   6900
agcagattca atagagacta caagattttg cacttgtaca taatcatcag tgtcaccggt   6960
ataaagcatc atgatctgac catcgggtag gatggtagcg gacccagtcc agacaccgtt   7020
aatatcgtac cattgatcag gaaccatggc aaaaggcaag tagagccagt ggatcaagtc   7080
cttggatacg gcatggcccc atgtgatatt tccccaaata gctgaatctg gattgtattg   7140 ataaaaaga tgtaccatc ccttgtggta caatggacca ttaggatcgt tcatccaatt     7200
tttttgaggt tgaaaatggt aagcagttct ttgccagcta agcatagcat ggaccacgc    7260 ataagaaacg tgactagcat tgacgacatc tcgaaaagtc ttatcggaga ctccctgaga   7320
aacacctctt gacggcggcg ccggcgaacg ggagttactg tgcaagtccg gtgactggtt   7380
gttgaggatc ggaaagaagg ctacagaaag caaaaggaaa gaggagagga aaatgccgga   7440
gatgatttta agggacttcc ggtggccgga atcgggttga tccggaggat gtgtaatg    7500 ggaggcggag ttttccgggt cataactgga atggtactgc gtggccatac tcgtgcctaa   7560
```

```
aatggcgaat aagtagagta taacactaca tattctccct ctcttccctt tcttgatggg    7620
acatcggtga aataaccttc aaatgaaaaa aagaatgaag aagatatggc ttgatgaaga    7680
actctttatc cagaaatggt actctagctt ctaagcccca cgcggatgta gccttgtttg    7740
ctcttaaaca gtcatactgg tgaagcgctt ttatcttgcg acatgtttcc gtgtggaact    7800
cttccttgtt tggagccttg tggaagtaca agtagccacc aaaaatttcg tcagcacctt    7860
cccctgatat gaccatcttc actcctagtg atttaatctt acgtgacata aggaacatag    7920
gagtgctggc tcttattgtt gttacatcat acgtctcgat atgatatata acatcttcaa    7980
tagcatcaat cccgtcctga acagtaaagt gaaactcgtg gtgaacggtt cctaaaaagt    8040
cagcaacttc tttttgcagcc ttgagatctg gtgagccctc gagaacattt tgaagttttc    8100 cctccgggc acttgtactc tagcaagaac ggagggctta ggagatggta caatcccgct    8160
tggttctctg aagcaattcc ttccactcct tatgacactt tggttctgag gcgtgccttc    8220
gaaaatgctg ttatcaaacg gttgatgact gatgtcccct ttggcgttct gctctcgggg    8280
ggacttgatt cgtctttggt tgcttctgtc actactcgat acttggctgg aacaaaagct    8340
gctaagcaat ggggagcaca acttcattcc ttctgtgttg gtctcgaggg ctcaccagat    8400
ctcaaggctg caaagaagt tgctgacttt ttaggaaccg ttcaccacga gtttcacttt    8460
actgttcagg acgggattga tgctattgaa gatgttatat atcatatcga gacgtatgat    8520
gtaacaacaa taagagccag cactcctatg ttccttatgt cacgtaagat taatcacta    8580 ggagtgaaga tggtcatatc aggggaaggt gctgacgaaa tttttggtgg ctacttgtac    8640
ttccacaagg ctccaaacaa ggaagagttc cacacgaaaa catgtcgcaa gataaaagcg    8700
cttcaccagt atgactgttt aagagcaaac aaggctacat ccgcgtgggg cttagaagct    8760
agagtaccat ttctggataa agagttcttc atcaagccat atcttcttca ttcttttttt    8820
catttgaagg ttatttcacc gatgtcccat caagaaaggg aagagaggga gaatatgtag    8880
tgttatactc tacttattcg ccattttagg cacgagtatg gccacgcagt accattccag    8940
ttatgacccg gaaaactccg cctcccatta cacattcctc ccggatcaac ccgattccgg    9000
ccaccggaag tcccttaaaa tcatctccgg cattttcctc tcctctttcc ttttgctttc    9060
tgtagccttc tttccgatcc tcaacaacca gtcaccggac ttgcagagta actcccgttc    9120
gccggcgccg ccgtcaagag gtgtttctca gggagtctcc gataagactt ttcgagatgt    9180
cgtcaatgct agtcacgttt cttatgcgtg gtccaatgct atgcttagct ggcaaagaac    9240
tgcttaccat tttcaacctc aaaaaaattg gatgaacgat cctaatggtc cattgtacca    9300
caagggatgg tatcatcttt tttatcaata caatccagat tcagctattt ggggaaatat    9360
cacatggggc catgccgtat ccaaggactt gatccactgg ctctacttgc cttttgccat    9420
ggttcctgat caatggtacg atattaacgg tgtctggact gggtccgcta ccatcctacc    9480
cgatggtcag atcatgatgc tttataccgg tgacactgat gattatgtac aagtgcaaaa    9540
tcttgtagtc tctattgaat ctgctgagat tacactttga tggatgatgc tctgtttttg    9600
ttttcttgtt ctgttttttt atgttgaaat cagctttgtt gcttgatttc attgaagttg    9660
ttattcaaga ataaatcagt tacaattata ctagtcccta gacttgtcca tcttctggat    9720
tggccaactt aattaatgta tgaaataaaa ggatgcacac atagtgacat gctaatcact    9780
ataatgtggg catcaaagtt gtgtgttatg tgtaattact aattatctga ataagagaaa    9840
gagatcatcc atatttctta tcctaaatga atgtcacgtg tctttataat tctttgatga    9900
accagatgca ttttattaac caattccata tacgagctcc ctatttttt actatattat    9960
```

```
actcaaccca atgagcataa agactgtaaa atctcaaatt cctgagaagc atatttatcg    10020
atcccacaga cttgatagtt ccataatcca tacgctgcag ccaaattgct agtgtgttga    10080
acatttaaca cgtagagaac tagaaaagat ataaaactaa gattgatatc caaaatagac    10140
gagaacaata agcaaaaact cttagttttg aaataaatca acaatcccga gggttgtcac    10200
atacatcaaa aacgaaaatc catatagcaa aaaaaactct aaattaccgt tcgacaaaaa    10260
gagaaaactg ataggacatt tgctaaacat taaaatcaat atgaacgtct cccatcaccc    10320
tctgtgatca catctttgaa agcaccgcca atgggaatca taggtagaac gtgctcctga    10380
tgaggtacaa tcacatccaa caagtatggc ccaggagtgt ctaacatctt ttgaatggca    10440
gctctaagat catccctgtg tgacactctt gcagcaggta cgccacaagc ctctgcgaat    10500
ttcaacatat tagggaagat ctcttcctca ttagcaggat cacccaagta agtgtgtgct    10560
ctgttagcct tatagaatcg atcctccagt tgaaccacca ttcccaagtg ttgattattc    10620
agcaacataa tcttaactgg gagattctcc accttaattg ttgctaactc ctgcacattc    10680
atgataaaac tcccgtcacc atcaatgtca accacaatct caccccggtct tccaacagcc    10740
gcacctattg cagcaggcaa accaaatccc attgctccta atccaccaga tgtcaaccat    10800
tggtgtggct ttttgtactt atagtattgg gcagcccaca tctggtgttg ccccacacca    10860
gtactaataa tggcatttcc gttagttaac tcatcaagaa cctgaatagc atattgtgga    10920
gggatggctt caccaaaagt cttaaaactc aatgggtact tcaccttctg ttccgttaac    10980
tcctgtctcc aagcagaaaa gtccaacttc agcttacctt cttttaccctc caatatggaa    11040
ttcaaaccct gtaatgccaa cttgatatct gcacaaatgg aaacatgagg ttgcttgttc    11100
tttccaatct cagccgaatc aatatcaatg tggacaattt tcgctcggct agcaaaagct    11160
tccaatttac cagtaactcg atcatcaaac ctcaccccaa atgcaagcaa caaatcacta    11220
ccatccacag cataattagc atacacagtc ccatgcatac ccaacatttg aagggaaagc    11280
tcatccccag ttggaaaagc tccaagaccc atcaaagtac tcgccacagg aatacccgta    11340
agctccacaa atcgtctcag ctcctcactt gattgcaaac acccaccacc cacatacaaa    11400
acaggcttct tcgactccga aatcagccta ataatttgtt ccaaaagcat ctcattaggc    11460
aatttaggta atctagacat gtaaccaggc aacctcattg gctgatccca attaggtatc    11520
accaattgtt gctgaatatc cttaggtaca tcaatcaaaa ccggcccagg ccgtcccgat    11580
ttcgctagaa aaaacgcttc acgaacaacc ctaggaatat cctctacatc cataacaaga    11640
taattatgct tcgtaataga tctcgttacc tcaacaatag gcgtttcctg aaacgcatca    11700
gtaccaatca tcctcctcgg cacttgaccc gtaatagcaa caatcggaat actatccaac    11760
aaaagcatccg caagaccact aacaagattc gtagctcccg gaccagaggt agcaatgcaa    11820
acaccaggga acccagtcgc ccgtgcgtaa ccctctgcag caaacacacc accttgctca    11880
tgacgtggca gcacattacg aataatattc gaacgtgtca aagcctgatg aatctcccata    11940
gaagcacctc ctgggtacgc aaatacatcc gtaacccct cccttttcaag tgcctccaca    12000
agaacatcac aacccttttct gggttcgtca ggggcgaaac gggaaacgaa tgtttcaggt    12060
tcagaaacgt cgttatgggt ggtagtggat atgacgacat tggaaacggc gaaccacga    12120
cgatgatgat gggtgtgggt gagatgaagg ggtgaggctt tttgagggtg attgtggaaa    12180
gggaaggtag atctaggaag aatggtggaa gatttggagg aagatggagg tagggttttg    12240
gagaaacatg gagatggtga gcagcagcc gccataccctc cacgtagacg gagcaccaaa    12300
```

-continued

```
tggagggtag actccttctg gatgttgtaa tcagctagag tacgtccgtc ctccaactgc    12360
tttccggcga agataagcct ttgctgatcc gggggaattc cttccttatc ctggatctta    12420
gccttaacgt tgtcgattgt atcagaactt tccacctcta gggtgatagt ctttccggtg    12480
agagttttca caaagatctg catctgcaaa ttcataaaaa caacaatcag acaacgaaa     12540 aaaactcaaa tttagggctt ttcacactcc ctgattagct gattcgagaa ttaaaaccaa    12600
acaatctaaa acacggggaa aaaactcaaa tttagggctt tttcatcaaa acagccggag    12660
aaactcaaat ttagggcttt ttcatcaaaa cagccggaga aactcaaatt ttaggccttc    12720
agaatcaaac cgacgaaaaa acacaaattc tagggctttt tcatcaaatc aaccggaaaa    12780
actcaaattt aaggccttt tcatcaaaca aatgtaaaaa ctctaatttt aaacctttag    12840
aatcgaatcg acagaaaaaa aatctcaaac taggggcttt ttcatcaaaa caacggggaa    12900
aactccaatt gtaggccttt tccatcaaac caacgtaaaa aaactcaaat tttaggcctt    12960
ttccatcaag acaaccgaaa aaaaactcaa aattaagggc tataacagca cctgattagc    13020
taattcgaga attgacagga tatatggtac tgtaaac                             13057
```

<210> SEQ ID NO 15
<211> LENGTH: 3014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
atttagcagc attccagatt gggttcaatc aacaaggtac gagccatatc actttattca      60
aattggtatc gccaaaacca agaaggaact cccatcctca aaggtttgta aggaagaatt     120
ctcagtccaa agcctcaaca aggtcagggt acagagtctc caaaccatta gccaaaagct     180
acaggagatc aatgaagaat cttcaatcaa agtaaactac tgttccagca catgcatcat     240
ggtcagtaag tttcagaaaa agacatccac cgaagactta agttagtgg gcatctttga     300 aagtaatctt gtcaacatcg agcagctggc ttgtggggac cagacaaaaa aggaatggtg     360
cagaattgtt aggcgcacct accaaaagca tctttgcctt tattgcaaag ataaagcaga     420
ttcctctagt acaagtgggg aacaaaataa cgtggaaaag agctgtcctg acagcccact     480
cactaatgcg tatgacgaac gcagtgacga ccacaaaaga attccctcta tataagaagg     540
cattcattcc catttgaagg atcatcagat actcaaccaa tactagtatg ttaagggcta     600
taacagcacc tgattagcta attcgagaat ctaaacagac aaaaaccaaa gtccgtcctg     660
tagaaacccc aacccgtgaa atcaaaaaac tcgacggcct gtgggcattc agtctggatc     720
gcgaaaactg tggaattgat cagcgttggt gggaaagcgc gttacaagaa agccgggcaa     780
ttgctgtgcc aggcagtttt aacgatcagt tcgccgatgc agatattcgt aattatgcgg     840
gcaacgtctg gtatcagcgc gaagtcttta taccgaaagg ttgggcaggc cagcgtatcg     900
tgctgcgttt cgatgcggtc actcattacg gcaaagtgtg ggtcaataat caggaagtga     960
tggagcatca gggcggctat acgccatttg aagccgatgt cacgccgtat gttattgccg    1020
ggaaaagtgt acgtaagttt ctgcttctac ctttgatata tatataataa ttatcattaa    1080
ttagtagtaa tataatattt caaatatttt tttcaaaata aaagaatgta gtatatagca    1140
attgcttttc tgtagtttat aagtgtgtat attttaattt ataacttttc taatatatga    1200
ccaaaatttg ttgatgtgca ggtatcaccg tttgtgtgaa caacgaactg aactggcaga    1260
```

```
ctatcccgcc gggaatggtg attaccgacg aaaacggcaa gaaaaagcag tcttacttcc    1320
atgatttctt taactatgcc ggaatccatc gcagcgtaat gctctacacc acgccgaaca    1380
cctgggtgga cgatatcacc gtggtgacgc atgtcgcgca agactgtaac cacgcgtctg    1440
ttgactggca ggtggtggcc aatggtgatg tcagcgttga actgcgtgat gcggatcaac    1500
aggtggttgc aactggacaa ggcactagcg ggactttgca agtggtgaat ccgcacctct    1560
ggcaaccggg tgaaggttat ctctatgaac tgtgcgtcac agccaaaagc cagacagagt    1620
gtgatatcta cccgcttcgc gtcggcatcc ggtcagtggc agtgaagggc gaacagttcc    1680
tgattaacca caaaccgttc tactttactg gctttggtcg tcatgaagat gcggacttgc    1740
gtggcaaagg attcgataac gtgctgatgg tgcacgacca cgcattaatg gactggattg    1800
gggccaactc ctaccgtacc tcgcattacc cttacgctga agagatgctc gactgggcag    1860
atgaacatgg catcgtggtg attgatgaaa ctgctgctgt cggctttaac ctctcttttag    1920 gcattggttt cgaagcgggc aacaagccga agaactgta cagcgaagag cagtcaacg    1980 gggaaactca gcaagcgcac ttacaggcga ttaaagagct gatagcgcgt gacaaaaacc    2040
acccaagcgt ggtgatgtgg agtattgcca acgaaccgga tacccgtccg caaggtgcac    2100
gggaatattt cgcgccactg gcggaagcaa cgcgtaaact cgaccgacg cgtccgatca    2160 cctgcgtcaa tgtaatgttc tgcgacgctc acaccgatac catcagcgat ctctttgatg    2220
tgctgtgcct gaaccgttat tacgatggt atgtccaaag cggcgatttg gaaacggcag    2280
agaaggtact ggaaaagaa cttctggcct ggcaggagaa actgcatcag ccgattatca    2340
tcaccgaata cggcgtggat acgttagccg ggctgcactc aatgtacacc gacatgtgga    2400
gtgaagagta tcagtgtgca tggctggata tgtatcaccg cgtctttgat cgcgtcagcg    2460
ccgtcgtcgg tgaacaggta tggaatttcg ccgattttgc gacctcgcaa ggcatattgc    2520
gcgttggcgg taacaagaaa gggatcttca ctcgcgaccg caaaccgaag tcggcggctt    2580
ttctgctgca aaaacgctgg actggcatga acttcggtga aaaaccgcag cagggaggca    2640
aacaatgaaa gcttttgatt ttaatgttta gcaaatgtcc tatcagtttt ctcttttttgt    2700 cgaacggtaa tttagagttt tttttgctat atggatttc gtttttgatg tatgtgacaa    2760
ccctcgggat tgttgattta tttcaaaact aagagttttt gcttattgtt ctcgtctatt    2820
ttggatatca atcttagttt tatatctttt ctagttctct acgtgttaaa tgttcaacac    2880
actagcaatt tggctgcagc gtatggatta tggaactatc aagtctgtgg gatcgataaa    2940
tatgcttctc aggaatttga gatttacag tctttatgct cattgggttg agtataatat    3000
agtaaaaaaa tagg                                                      3014
```

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaggcattca ttcccatttg                                                  20

<210> SEQ ID NO 17
<211> LENGTH: 20
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 17
gacccacact tgccgtaat                                                    20

<210> SEQ ID NO 18
<211> LENGTH: 4164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atggctccta agaagaagag gaaggttgag ccaggatctc caggtggaca gtctctcatg     60
gataagaagt actccatcgg cctcgatatc ggcactaact ctgttggatg ggctgtgatc    120
actgatgagt acaaggtgcc atccaagaag ttcaaggttc tcggcaacac tgataggcac    180
tccatcaaga gaaccttat cggcgctctc ctcttcgatt ccggtgaaac tgctgaggct    240
actaggctta gaggactgc tagaaggcgt tacactaggc gtaagaacag gatctgctac    300
ctccaagaga tcttctccaa cgagatggct aaagtggatg attcattctt ccacaggctc    360
gaagagtcct tcttggtgga agaagataag aagcacgaga ggcacccaat cttcggcaac    420
attgtgatg aagtggctta ccacgagaag tacccaacta tctaccacct ccgtaagaag    480
ctcgttgatt ccactgataa ggctgatctc aggctcatct accttgctct cgctcacatg    540
atcaagttca ggggacactt cctcatcgag ggtgatctca acccagataa ctccgatgtg    600
gataagttgt tcatccagct cgtgcagact acaaccagc ttttcgaaga gaacccaatc    660
aacgcttccg gtgtggatgc taaggctatt cttttctgcta ggctctccaa gtccaggcgt    720
cttgagaatc ttattgctca gctcccaggc gagaagaaga acggactttt cggaaacttg    780
atcgctctct cccttggcct cactccaaac ttcaagtcca acttcgatct cgctgaggat    840
gcaaagctcc agctctctaa ggatacttac gatgatgatc tcgataacct cctcgctcag    900
atcggagatc agtacgctga tttgttcctc gctgctaaga acctctccga tgctatcctc    960
ctctctgata tcctccgtgt gaacactgag atcactaagg ctccactctc cgcttccatg   1020
attaagaggt acgatgagca ccaccaggat cttacacttc tcaaggctct tgtgaggcag   1080
cagcttcctg agaagtacaa agagattttc ttcgatcagt ccaagaacgg ctacgctggt   1140
tacattgatg gtgcgcttc tcaagaagag ttctacaagt tcatcaagcc aatcctcgaa   1200
aagatggatg gaactgagga actcctcgtg aagctcaaca gagaggatct ccttaggaag   1260
cagaggactt tcgataacgg ctccattcca caccagattc accttggtga gttgcacgct   1320
attctcaggc gtcaagagga tttctaccca ttcctcaagg ataaccgtga agatcgag   1380
aagattctta ctttccgtat cccttactac gtgggaccac ttgctagggg aaattctagg   1440
ttcgcttgga tgactaggaa gtccgaagag actatcactc catggaactt cgaagaggtg   1500
gtggataagg gtgctagtgc tcagtctttc atcgagagga tgactaactt cgataagaac   1560
cttccaaacg agaaggtgct cccaaagcac tctttgctct acgagtactt cactgtgtac   1620
aacgagttga ctaaggtgaa gtacgtgaca gagggcatga ggaagccagc ttttttgtct   1680
ggtgagcaga agaaggctat cgttgatctc ttgttcaaga ctaaccgtaa ggtgacagtg   1740
aagcagctca agaggatta cttcaagaaa atcgagtgct tcgattctgt tgagatctcc   1800
ggcgttgagg ataggttcaa tgcttcccctt ggcacatacc acgatttgct caagatcatt   1860
```

```
aaggataagg atttcttgga taacgaggaa aacgaggata ttcttgagga tatcgtgctt    1920
actctcactc tcttcgagga tcgtgagatg attgaggaaa ggctcaagac ttacgctcac    1980
cttttcgatg ataaggtgat gaagcagttg aagaggcgta ggtacactgg atggggaagg    2040 cttttctagga agctcatcaa cggcatcagg gataagcagt ccggtaagac tattctcgat    2100
ttcctcaagt ccgatggctt cgcaaaccgt aacttcatgc agctcatcca cgatgattcc    2160
ctcactttta aagaggatat ccagaaggct caggtttccg acaaggcga ttctcttcat    2220 gagcacattg ctaacctcgc tggctcccca gctattaaga agggaattct ccagactgtg    2280
aaagtggtgg atgagttggt gaaggtgatg ggaaggcata agccagagaa catcgtgatc    2340
gagatggcac gtgagaacca gactactcag aagggccaga agaactccag ggaaaggatg    2400
aagaggatcg aggaaggcat caaagagctt ggctcccaga tccttaaaga gcacccagtt    2460
gagaacactc agctccagaa tgagaagctc tacctctact acctccagaa cggcagggat    2520
atgtatgtgg atcaagagtt ggatatcaac aggctctccg attatgatgt tgatcacatc    2580
gtgccacagt cattcttgaa ggatgattcc atcgataaca aggtgctcac taggtccgat    2640
aagaataggg gcaagtctga taacgtgcca agtgaagagg ttgtgaagaa atgaagaac    2700 tactggcgtc agcttctcaa cgctaagctc attactcagc gtaagttcga taacttgaca    2760
aaggctgaga ggggaggcct ctctgaattg gataaggcag gattcatcaa gaggcagctc    2820
gtggaaacta ggcagatcac aaagcacgtg gcacagatcc tcgattccag gatgaacact    2880
aagtatgatg agaacgataa gttgatccgt gaggttaagg tgatcactct caagtctaag    2940
ctcgtgtccg attttaggaa ggatttccaa ttctacaagg tgagggaaat caacaactac    3000
caccacgctc acgatgctta ccttaacgct gttgtgggaa cagctcttat caagaagtat    3060
ccaaagttgg agtccgagtt cgtgtacggc gattacaagg tttacgatgt gaggaagatg    3120
atcgctaagt ccgagcaaga gatcggcaag gctactgcta agtactttt ctactccaac    3180 atcatgaatt tcttcaagac agagatcaca ctcgctaacg gcgagattag gaagaggcca    3240
ctcattgaga ctaacggtga gactggtgag atcgtgtggg ataagggaag ggatttcgct    3300
actgtgcgta aggtgctctc tatgccacag gtgaacattg tgaaaaagac agaggtgcag    3360
actggcggct tctccaaaga gtctattctc ccaaagagga actccgataa gctcattgct    3420
aggaagaagg attgggaccc aaagaagtac ggcggcttcg atagtcctac tgtggcttac    3480
tctgttcttg tggtggctaa ggttgagaag ggcaagtcaa agaagctcaa gtctgttaag    3540
gaattgctcg gcatcactat catggaaagg tcctcattcg agaagaaccc tattgatttc    3600
cttgaggcta agggctacaa agaggttaag aaggatctca tcatcaagct ccctaagtac    3660
tccttgttcg agcttgagaa cggccgtaag aggatgcttg cttctgctgg tgaactccag    3720
aagggaaacg aacttgctct cccatccaag tacgttaact ttctctacct cgcttcccac    3780
tacgagaagt tgaagggatc accagaggat aacgaacaga gcaacttttt cgttgagcag    3840
cacaagcact atctcgatga gattatcgag cagatctccg agttctccaa gcgtgtgatt    3900
ctcgctgatg caaacctcga taaggtgttg tccgcttaca caagcaccg tgataagcct    3960 attcgtgagc aggctgagaa catcatccac cttttcactc tcactaacct cggtgctcca    4020
gctgctttca gtacttcga tacaacaatc gataggaagc gttacacatc cacaaaagag    4080
gtgctcgatg ctactctcat tcaccagtcc atcactggcc tttacgagac taggatcgat    4140 cttttctcagc tcggaggcga ttga                                         4164
```

<210> SEQ ID NO 19
<211> LENGTH: 1387
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Met Ala Pro Lys Lys Arg Lys Val Glu Pro Gly Ser Pro Gly Gly
1               5                   10                  15

Gln Ser Leu Met Asp Lys Lys Tyr Ser Ile Gly Leu Asp Ile Gly Thr
                20                  25                  30

Asn Ser Val Gly Trp Ala Val Ile Thr Asp Glu Tyr Lys Val Pro Ser
            35                  40                  45

Lys Lys Phe Lys Val Leu Gly Asn Thr Asp Arg His Ser Ile Lys Lys
50                  55                  60

Asn Leu Ile Gly Ala Leu Leu Phe Asp Ser Gly Glu Thr Ala Glu Ala
65                  70                  75                  80

Thr Arg Leu Lys Arg Thr Ala Arg Arg Arg Tyr Thr Arg Arg Lys Asn
                85                  90                  95

Arg Ile Cys Tyr Leu Gln Glu Ile Phe Ser Asn Glu Met Ala Lys Val
                100                 105                 110

Asp Asp Ser Phe Phe His Arg Leu Glu Glu Ser Phe Leu Val Glu Glu
            115                 120                 125

Asp Lys Lys His Glu Arg His Pro Ile Phe Gly Asn Ile Val Asp Glu
        130                 135                 140

Val Ala Tyr His Glu Lys Tyr Pro Thr Ile Tyr His Leu Arg Lys Lys
145                 150                 155                 160

Leu Val Asp Ser Thr Asp Lys Ala Asp Leu Arg Leu Ile Tyr Leu Ala
                165                 170                 175

Leu Ala His Met Ile Lys Phe Arg Gly His Phe Leu Ile Glu Gly Asp
                180                 185                 190

Leu Asn Pro Asp Asn Ser Asp Val Asp Lys Leu Phe Ile Gln Leu Val
            195                 200                 205

Gln Thr Tyr Asn Gln Leu Phe Glu Glu Asn Pro Ile Asn Ala Ser Gly
        210                 215                 220

Val Asp Ala Lys Ala Ile Leu Ser Ala Arg Leu Ser Lys Ser Arg Arg
225                 230                 235                 240

Leu Glu Asn Leu Ile Ala Gln Leu Pro Gly Glu Lys Lys Asn Gly Leu
                245                 250                 255

Phe Gly Asn Leu Ile Ala Leu Ser Leu Gly Leu Thr Pro Asn Phe Lys
                260                 265                 270

Ser Asn Phe Asp Leu Ala Glu Asp Ala Lys Leu Gln Leu Ser Lys Asp
            275                 280                 285

Thr Tyr Asp Asp Asp Leu Asp Asn Leu Leu Ala Gln Ile Gly Asp Gln
        290                 295                 300

Tyr Ala Asp Leu Phe Leu Ala Ala Lys Asn Leu Ser Asp Ala Ile Leu
305                 310                 315                 320

Leu Ser Asp Ile Leu Arg Val Asn Thr Glu Ile Thr Lys Ala Pro Leu
                325                 330                 335

Ser Ala Ser Met Ile Lys Arg Tyr Asp Glu His His Gln Asp Leu Thr
                340                 345                 350

Leu Leu Lys Ala Leu Val Arg Gln Gln Leu Pro Glu Lys Tyr Lys Glu
            355                 360                 365
```

```
Ile Phe Phe Asp Gln Ser Lys Asn Gly Tyr Ala Gly Tyr Ile Asp Gly
    370                 375                 380

Gly Ala Ser Gln Glu Glu Phe Tyr Lys Phe Ile Lys Pro Ile Leu Glu
385                 390                 395                 400

Lys Met Asp Gly Thr Glu Glu Leu Leu Val Lys Leu Asn Arg Glu Asp
                405                 410                 415

Leu Leu Arg Lys Gln Arg Thr Phe Asp Asn Gly Ser Ile Pro His Gln
            420                 425                 430

Ile His Leu Gly Glu Leu His Ala Ile Leu Arg Arg Gln Glu Asp Phe
        435                 440                 445

Tyr Pro Phe Leu Lys Asp Asn Arg Glu Lys Ile Glu Lys Ile Leu Thr
    450                 455                 460

Phe Arg Ile Pro Tyr Tyr Val Gly Pro Leu Ala Arg Gly Asn Ser Arg
465                 470                 475                 480

Phe Ala Trp Met Thr Arg Lys Ser Glu Glu Thr Ile Thr Pro Trp Asn
                485                 490                 495

Phe Glu Glu Val Val Asp Lys Gly Ala Ser Ala Gln Ser Phe Ile Glu
            500                 505                 510

Arg Met Thr Asn Phe Asp Lys Asn Leu Pro Asn Glu Lys Val Leu Pro
        515                 520                 525

Lys His Ser Leu Leu Tyr Glu Tyr Phe Thr Val Tyr Asn Glu Leu Thr
    530                 535                 540

Lys Val Lys Tyr Val Thr Glu Gly Met Arg Lys Pro Ala Phe Leu Ser
545                 550                 555                 560

Gly Glu Gln Lys Lys Ala Ile Val Asp Leu Leu Phe Lys Thr Asn Arg
                565                 570                 575

Lys Val Thr Val Lys Gln Leu Lys Glu Asp Tyr Phe Lys Lys Ile Glu
            580                 585                 590

Cys Phe Asp Ser Val Glu Ile Ser Gly Val Glu Asp Arg Phe Asn Ala
        595                 600                 605

Ser Leu Gly Thr Tyr His Asp Leu Leu Lys Ile Ile Lys Asp Lys Asp
    610                 615                 620

Phe Leu Asp Asn Glu Glu Asn Glu Asp Ile Leu Glu Asp Ile Val Leu
625                 630                 635                 640

Thr Leu Thr Leu Phe Glu Asp Arg Glu Met Ile Glu Glu Arg Leu Lys
                645                 650                 655

Thr Tyr Ala His Leu Phe Asp Asp Lys Val Met Lys Gln Leu Lys Arg
            660                 665                 670

Arg Arg Tyr Thr Gly Trp Gly Arg Leu Ser Arg Lys Leu Ile Asn Gly
        675                 680                 685

Ile Arg Asp Lys Gln Ser Gly Lys Thr Ile Leu Asp Phe Leu Lys Ser
    690                 695                 700

Asp Gly Phe Ala Asn Arg Asn Phe Met Gln Leu Ile His Asp Asp Ser
705                 710                 715                 720

Leu Thr Phe Lys Glu Asp Ile Gln Lys Ala Gln Val Ser Gly Gln Gly
                725                 730                 735

Asp Ser Leu His Glu His Ile Ala Asn Leu Ala Gly Ser Pro Ala Ile
            740                 745                 750

Lys Lys Gly Ile Leu Gln Thr Val Lys Val Val Asp Glu Leu Val Lys
        755                 760                 765

Val Met Gly Arg His Lys Pro Glu Asn Ile Val Ile Glu Met Ala Arg
    770                 775                 780
```

-continued

```
Glu Asn Gln Thr Thr Gln Lys Gly Gln Lys Asn Ser Arg Glu Arg Met
785                 790                 795                 800

Lys Arg Ile Glu Glu Gly Ile Lys Glu Leu Gly Ser Gln Ile Leu Lys
            805                 810                 815

Glu His Pro Val Glu Asn Thr Gln Leu Gln Asn Glu Lys Leu Tyr Leu
            820                 825                 830

Tyr Tyr Leu Gln Asn Gly Arg Asp Met Tyr Val Asp Gln Glu Leu Asp
            835                 840                 845

Ile Asn Arg Leu Ser Asp Tyr Asp Val Asp His Ile Val Pro Gln Ser
850                 855                 860

Phe Leu Lys Asp Asp Ser Ile Asp Asn Lys Val Leu Thr Arg Ser Asp
865                 870                 875                 880

Lys Asn Arg Gly Lys Ser Asp Asn Val Pro Ser Glu Glu Val Val Lys
            885                 890                 895

Lys Met Lys Asn Tyr Trp Arg Gln Leu Leu Asn Ala Lys Leu Ile Thr
            900                 905                 910

Gln Arg Lys Phe Asp Asn Leu Thr Lys Ala Glu Arg Gly Gly Leu Ser
            915                 920                 925

Glu Leu Asp Lys Ala Gly Phe Ile Lys Arg Gln Leu Val Glu Thr Arg
930                 935                 940

Gln Ile Thr Lys His Val Ala Gln Ile Leu Asp Ser Arg Met Asn Thr
945                 950                 955                 960

Lys Tyr Asp Glu Asn Asp Lys Leu Ile Arg Glu Val Lys Val Ile Thr
            965                 970                 975

Leu Lys Ser Lys Leu Val Ser Asp Phe Arg Lys Asp Phe Gln Phe Tyr
            980                 985                 990

Lys Val Arg Glu Ile Asn Asn Tyr His His Ala His Asp Ala Tyr Leu
            995                 1000                1005

Asn Ala Val Val Gly Thr Ala Leu Ile Lys Lys Tyr Pro Lys Leu
    1010                1015                1020

Glu Ser Glu Phe Val Tyr Gly Asp Tyr Lys Val Tyr Asp Val Arg
    1025                1030                1035

Lys Met Ile Ala Lys Ser Glu Gln Glu Ile Gly Lys Ala Thr Ala
    1040                1045                1050

Lys Tyr Phe Phe Tyr Ser Asn Ile Met Asn Phe Phe Lys Thr Glu
    1055                1060                1065

Ile Thr Leu Ala Asn Gly Glu Ile Arg Lys Arg Pro Leu Ile Glu
    1070                1075                1080

Thr Asn Gly Glu Thr Gly Glu Ile Val Trp Asp Lys Gly Arg Asp
    1085                1090                1095

Phe Ala Thr Val Arg Lys Val Leu Ser Met Pro Gln Val Asn Ile
    1100                1105                1110

Val Lys Lys Thr Glu Val Gln Thr Gly Gly Phe Ser Lys Glu Ser
    1115                1120                1125

Ile Leu Pro Lys Arg Asn Ser Asp Lys Leu Ile Ala Arg Lys Lys
    1130                1135                1140

Asp Trp Asp Pro Lys Lys Tyr Gly Gly Phe Asp Ser Pro Thr Val
    1145                1150                1155

Ala Tyr Ser Val Leu Val Val Ala Lys Val Glu Lys Gly Lys Ser
    1160                1165                1170

Lys Lys Leu Lys Ser Val Lys Glu Leu Leu Gly Ile Thr Ile Met
    1175                1180                1185

Glu Arg Ser Ser Phe Glu Lys Asn Pro Ile Asp Phe Leu Glu Ala
```

```
                    1190                1195                1200

Lys Gly  Tyr Lys Glu Val  Lys Lys Asp Leu Ile  Ile Lys Leu Pro
        1205                1210                1215

Lys Tyr  Ser Leu Phe Glu  Leu Glu Asn Gly Arg  Lys Arg Met Leu
        1220                1225                1230

Ala Ser  Ala Gly Glu Leu  Gln Lys Gly Asn Glu  Leu Ala Leu Pro
        1235                1240                1245

Ser Lys  Tyr Val Asn Phe  Leu Tyr Leu Ala Ser  His Tyr Glu Lys
        1250                1255                1260

Leu Lys  Gly Ser Pro Glu  Asp Asn Glu Gln Lys  Gln Leu Phe Val
        1265                1270                1275

Glu Gln  His Lys His Tyr  Leu Asp Glu Ile Ile  Glu Gln Ile Ser
        1280                1285                1290

Glu Phe  Ser Lys Arg Val  Ile Leu Ala Asp Ala  Asn Leu Asp Lys
        1295                1300                1305

Val Leu  Ser Ala Tyr Asn  Lys His Arg Asp Lys  Pro Ile Arg Glu
        1310                1315                1320

Gln Ala  Glu Asn Ile Ile  His Leu Phe Thr Leu  Thr Asn Leu Gly
        1325                1330                1335

Ala Pro  Ala Ala Phe Lys  Tyr Phe Asp Thr Thr  Ile Asp Arg Lys
        1340                1345                1350

Arg Tyr  Thr Ser Thr Lys  Glu Val Leu Asp Ala  Thr Leu Ile His
        1355                1360                1365

Gln Ser  Ile Thr Gly Leu  Tyr Glu Thr Arg Ile  Asp Leu Ser Gln
        1370                1375                1380

Leu Gly  Gly Asp
        1385

<210> SEQ ID NO 20
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gattctcgaa ttagctaatc gttttagagc tagaaatagc aagttaaaat aaggctagtc    60
cgttatcaac ttgaaaaagt ggcaccgagt cggtgctttt ttt                    103

<210> SEQ ID NO 21
<211> LENGTH: 34
<212> TYPE: PRT
<213> ORGANISM: Unknown
<220> FEATURE:
<223> OTHER INFORMATION: Description of Unknown: Central repeat domain
      polypeptide

<400> SEQUENCE: 21

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 22
<211> LENGTH: 1018
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 22

```
gtttacagta ccatatatcc tgtcaattct cgaattagct aatcaggtgc tgttatagcc      60
cttaattttg agtttttttt cggttgtctt gatggaaaag gcctaaaatt tgagtttttt     120
tacgttggtt tgatggaaaa ggcctacaat tggagttttc cccgttgttt tgatgaaaaa     180
gccccctagtt tgagatttttt tttctgtcga ttcgattcta aaggtttaaa attagagttt   240
ttacatttgt ttgatgaaaa aggccttaaa tttgagtttt tccggttgat ttgatgaaaa     300
agccctagaa tttgtgtttt ttcgtcggtt tgattctgaa ggcctaaaat ttgagtttct     360
ccggctgttt tgatgaaaaa gccctaaatt tgagtttctc cggctgtttt gatgaaaaag    420
ccctaaattt gagttttttc cccgtgtttt agattgtttg gttttaattc tcgaatcagc     480
taatcaggga gtgtgaaaag ccctaaattt gagtttttt cgttgttctg attgttgttt      540
ttatgaattt gcagatgcag atctttgtga aaactctcac cggaaagact atcaccctag     600
aggtggaaag ttctgataca atcgacaacg ttaaggctaa gatccaggat aaggaaggaa     660
ttcccccgga tcagcaaagg cttatcttcg ccggaaagca gttggaggac ggacgtactc     720
tagctgatta caacatccag aaggagtcta ccctccattt ggtgctccgt ctacgtggag     780
gtatggcggc tgctgcctca ccatctccat gtttctccaa aaccctacct ccatcttcct     840
ccaaatcttc caccattctt cctagatcta ccttcccttt ccacaatcac cctcaaaaag     900
cctcacccct tcatctcacc cacacccatc atcatcgtcg tggtttcgcc gtttccaatg     960
tcgtcatatc cactaccacc cataacgacg tttctgaacc tgaaacattc gtttcccg      1018
```

<210> SEQ ID NO 23
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23

```
atgttaaggg ctataacagc acctgattag ctaattcgag aatctaaaca gacaaaaacc      60
aaagtc                                                                 66
```

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24

```
tttggttttt gtctgtttag attctcgaat tagctaatca ggtgctgtta tagcccttaa      60
```

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25

-continued tttggttttt gtctgtttag attctcgaat tagctaatca ggtgctgtta tagcccttaa     60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tttggttttt gtctgtttag attctcgaat tagttaatca ggtgctgtta tagcccttaa     60

<210> SEQ ID NO 27
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tttggttttt gtctgtttag attctcgaat aatcaggtgc tgttatagcc cttaa          55

<210> SEQ ID NO 28
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tttggttttt gtctgtttag attctcgaaa tcaggtgctg ttatagccct taa             53

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tttggttttt gtctgtttag attctcgaac tgttatagcc cttaa                      45

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tttggttttt gtctgtttag attctcgaat caggtgctgt tatagccctt aa              52

<210> SEQ ID NO 31
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tttggttttt gtctgtttag attctcgaat taatcaggtg ctgttatagc ccttaa      56

<210> SEQ ID NO 32
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tttggttttt gtctgcttag attctcgaat taggtgctgt tatagccctt aa          52

<210> SEQ ID NO 33
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tttggttttt gtctgtttag attctcgaat tcaggtgctg ttatagccct taa         53

<210> SEQ ID NO 34
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tttggttttt gtctgtttag attctcgaat tatcaggtgc tgttatagcc cttaa       55

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tttggttttt gtctgtttag attctcgaat taatcaggtg ctgttatagc ccttaa      56

<210> SEQ ID NO 36
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tttggttttt gtctgtttag attctcgaat tataatcagg tgctgttata gcccttaa    58

<210> SEQ ID NO 37
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tttggttttt gtctgtttag attctcgaat tagcctaatc aggtgctgtt atagccctta  60

| a | 61 |

<210> SEQ ID NO 38
<211> LENGTH: 1450
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

| ctgatttcta ttataatttc tattaattgc cttcaaattt ctctttcaag gttagaaatc | 60 |
| ttctctatt tttggttttt gtctgtttag attctcgaat tagctaatca ggtgctgtta | 120 |
| aagccctaaa atttgagttt tttttccgtc gaattgatgc taaaggctta aaattagagt | 180 |
| ttttttcgtcg gtttgactct gaaggcctaa aatttggggt tttccgggtg atttgatgat | 240 |
| aaagccctag aatttgagtt tttttatttg tcggtttgat gaaaaaggcc ttaaatttaa | 300 |
| ttttttttccc ggttgatttg atgaaaaagc cctagaattt gtgtttttc gtcggtttga | 360 |
| ttctaaaggc ctaaaatttg agttttttccg gttgttttga tgaaaaagcc ctaaatttg | 420 |
| agttttttcc ccgtgtttta gattgtttgg ttttaattct tgaatcagat aatcagggag | 480 |
| tgtgaaaagc cctaaaattt gagtttttttt cgttgttctg attgttgttt ttatgaattt | 540 |
| gattctcgaa ttagctaatc aggtgctgtt atagccctta attttgagtt ttttttcggt | 600 |
| tgtcttgatg gaaaggcct aaaatttgag tttttttacg ttggtttgat ggaaaaggcc | 660 |
| tacaattgga gttttccccg ttgttttgat gaaaaagccc ctagtttgag attttttttc | 720 |
| tgtcgattcg attctaaagg tttaaaatta gagtttttac atttgtttga tgaaaaaggc | 780 |
| cttaaatttg agttttttccg gttgatttga tgaaaaagcc ctagaatttg tgtttttccgt | 840 |
| cggtttgatt ctgaaggttt gattctgaag gcctaaaatt tgagtttctc cggctgtttt | 900 |
| gatgaaaaag ccctaaattt gagttttctcc ggctgttttg atgaaaaagc cctaaatttg | 960 |
| agttttttcc ccgtgtttta gattgtttgg ttttaattct cgaatcagct aatcagggag | 1020 |
| tgtgaaaagc cctaaattttg agttttttttc gttgttctga ttgttgttttt tatgaatttg | 1080 |
| cagatgcaga tctttgtgaa aactctcacc ggaaagacta tcaccctaga ggtggaaagt | 1140 |
| tctgatacaa tcgacaacgt taaggctaag atccaggata aggaaggaat tcccccggat | 1200 |
| cagcaaaggc ttatcttcgc cggaaagcag ttggaggacg gacgtactct agctgattac | 1260 |
| aacatccaga aggagtctac cctccatttg gtgctccgtc tacgtggagg tatggcggct | 1320 |
| gctgcctcac catctccatg tttctccaaa accctacctc catcttcctc caaatcttcc | 1380 |
| accattcttc ctagatctac cttcccttt cacaatcacc ctcaaaaagc ctcaccccctt | 1440 |
| catctcaccc | 1450 |

<210> SEQ ID NO 39
<211> LENGTH: 891
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

| ttttcatctt ctatctgatt tctattataa tttctattaa ttgccttcaa atttctcttt | 60 |
| caaggttaga aatcttctct attttttggt ttttgtctgt ttagattctc gaattagcta | 120 |

```
atcaggtgct gttaaagccc taaaatttga gtttttttc cgccgaattg atgctaaagg    180
cttaaaatta gggttttttc gtcggtttga ctctgaaggc ctaaaatttg gggttttccg    240
ggtgatttga tgataaagcc ctagaatttg agttttttta tttgtcggtt tgatgaaaaa    300
ggccttaaat ttaattttt tcccggttga tttgatgaaa aagccctaga atttgtgttt    360
tttcgtcggt ttgattctaa aggcctaaaa tttgagtttt tccggttgtt ttgatgaaaa    420
agccctaaaa tttgagtttt ttccccgtgt tttagattgt ttggttttaa ttcttgaatc    480
agataatcag ggagtgtgaa aagccctaaa tttgagtttt tttcgttgtt ctgattgttg    540
tttttatgaa tttgcagatg cagatctttg tgaaaactct caccggaaag actatcaccc    600
tagaggtgga aacaatcgac aacgttaagg ctaagatcca ggataaggaa ggaattcccc    660
cggatcagca aaggcttatc ttcgccggaa agcagttgga ggacggacgt actctagctg    720
attacaacat ccagaaggag tctaccctcc atttggtgct ccgtctacgt ggaggtatgg    780
cggctgctgc ctcaccatct ccatgcttct ccaaaaccct acctccatct tcctccaaat    840
cttccaccat tcttcctaga tctaccttcc ctttccacaa tcaccctcaa a            891
```

<210> SEQ ID NO 40
<211> LENGTH: 900
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 40

```
ttttcatctt ctatctgatt tctattataa tttctattaa ttgccttcaa atttctcttt     60
caaggttaga aatcttctct attttttggt ttttgtctgt ttagattctc gaattagcta    120
atcaggtgct gttaaagccc taaaatttga gtttttttc cgccgaattg atgctaaagg    180
cttaaaatta gggttttttc gtcggtttga ctctgaaggc ctaaaatttg gggttttccg    240
ggtgatttga tgataaagcc ctagaatttg agttttttta tttgtcggtt tgatgaaaaa    300
ggccttaaat ttaattttt tcccggttga tttgatgaaa aagccctaga atttgtgttt    360
tttcgtcggt ttgattctaa aggcctaaaa tttgagtttt tccggttgtt ttgatgaaaa    420
agccctaaaa tttgagtttt ttccccgtgt tttagattgt ttggttttaa ttcttgaatc    480
agataatcag ggagtgtgaa aagccctaaa tttgagtttt tttcgttgtt ctgattgttg    540
tttttatgaa tttgcagatg cagatctttg tgaaaactct caccggaaag actatcaccc    600
tagaggtgga aagttctgat acaatcgaca acgttaaggc taagatccag gataaggaag    660
gaattccccc ggatcagcaa aggcttatct tcgccggaaa gcagttggag gacggacgta    720
ctctagctga ttacaacatc cagaaggagt ctaccctcca tttggtgctc cgtctacgtg    780
gaggtatggc ggctgctgcc tcaccatctc catgcttctc caaaaccccta cctccatctt    840 cctccaaatc ttccaccatt cttcctagat ctaccttccc tttccacaat caccctcaaa    900
```

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 41

```
gattctcgaa ttagctaatc gttttagag                                       29
```

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
caccgagtcg gtgctttttt t                                              21

<210> SEQ ID NO 43
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ttaagggcta taacagcacc tgattagcta attcgagaat ctaaacagac aaaaaccaaa    60

<210> SEQ ID NO 44
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ttaagggcta taacagcacc tgattaattc gagaatctaa acagacaaaa accaaa        56

<210> SEQ ID NO 45
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttaagggcta taacagcacc tgataattcg agaatctaaa cagacaaaaa ccaaa         55

<210> SEQ ID NO 46
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttaagggcta taacagcacc tgatttcgag aatctaaaca gacaaaaacc aaa           53

<210> SEQ ID NO 47
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttaaggggca taacagcacc tgattcgaga atctaaacag acaaaaacca aa            52

```
<210> SEQ ID NO 48
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttaagggcta taacagcacc tgattcgaga atctaaacag acaaaaacca aa            52

<210> SEQ ID NO 49
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttaagggcta taacagcatc gagaatctaa acagacaaaa accaaa                  46

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ttaagggcta taacagcacc tgattagata attcgagaat ctaaacagac aaaaaccaaa   60

<210> SEQ ID NO 51
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttaagggaaa gaacagcaca gcactagata attcgagaat ctaaacagac aaaaaccaaa   60
```